(12) United States Patent
Koide

(10) Patent No.: US 7,598,352 B2
(45) Date of Patent: Oct. 6, 2009

(54) METHOD OF IDENTIFYING POLYPEPTIDE MONOBODIES WHICH BIND TO TARGET PROTEINS AND USE THEREOF

(75) Inventor: Shohei Koide, Rochester, NY (US)

(73) Assignee: University of Rochester, Rochester, NY (US)

( * ) Notice: Subject to any disclaimer, the term of this patent is extended or adjusted under 35 U.S.C. 154(b) by 1079 days.

(21) Appl. No.: 10/006,760

(22) Filed: Nov. 19, 2001

(65) Prior Publication Data

US 2003/0186385 A1 Oct. 2, 2003

Related U.S. Application Data

(60) Provisional application No. 60/249,756, filed on Nov. 17, 2000.

(51) Int. Cl.
C12P 21/08 (2006.01)
A61K 36/16 (2006.01)
A61K 38/00 (2006.01)
C07K 14/00 (2006.01)
G01N 33/566 (2006.01)

(52) U.S. Cl. .................. 530/388.9; 530/380; 530/387.1; 530/381; 530/350; 435/7.1; 435/7.8; 436/501

(58) Field of Classification Search ................ 530/380, 530/387.1, 381, 350
See application file for complete search history.

(56) References Cited

U.S. PATENT DOCUMENTS 5,922,676 A * 7/1999 Pasqualini et al. ............ 514/12
6,673,901 B2 * 1/2004 Koide .......................... 530/380
6,818,418 B1 * 11/2004 Lipovsek et al. ........... 435/69.1

FOREIGN PATENT DOCUMENTS

WO WO 98/56915 12/1998

OTHER PUBLICATIONS

Garcia-Pardo A et al. Primary structure of human plasma fibronectin. Characterization of a 31,000-dalton fragment from the COOH-terminal region containing a free sulfhydryl group and a fibrin-binding site. J Biol Chem. Aug. 25, 1985;260(18):10320-5.*
Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Karatan et al. 2004. Chemistry and Biology 11:835-844.*
Wells JA. 1990 Biochemistry 29:29:8509-8517.*
Ngo et al. 1994 in The protein Folding Problem and Tertiary Structure Prediction pp. 491-495.*
Koide et al. 1998. J Mol Biol 284:1141-1151.*
Bowie et al 1990. Science 247:1306-1310.*

Koide et al., "The Fibronectin Type III Domain as a Scaffold for Novel Binding Proteins," *J. Mol. Biol.* 284:1141-1151 (1998).
Koide et al., "Stabilization of a Fibronectin Type III Domain by the Removal of Unfavorable Electrostatic Interactions on the Protein Surface," *Biochemistry* 40:10326-10333 (2001).
Koide et al., "Probing Protein Conformational Changes Inside the Cell Using Designer Binding Proteins: Application to Nuclear Receptors," *Protein Science* 10(2):142 (2001).
Richardson et al., "Phenotypic Knockout of the High-Affinity Human Interleukin 2 Receptor by Intracellular Single-Chain Antibodies Against the α Subunit of the Receptor," *Proc. Natl. Acad. Sci. USA* 92:3137-3141 (1995).
Abedi, et al., "Green Fluorescent Protein as a Scaffold for Intracellular Presentation of Peptides," *Nucleic Acids Research* 26(2):623-630 (1998).
Beste et al., "Small Antibody-like Proteins with Prescribed Ligand Specificities Derived from the Lipocalin Fold," *Proc. Natl. Acad. Sci. USA* 96:1898-1903 (1999).
Paige et al., "Estrogen Receptor (ER) Modulators Each Induce Distinct Conformational Changes in ER α and ER β," *Proc. Natl. Acad. Sci. USA* 96:3999-4004 (1999).
Smith, "Patch Engineering: a General Approach for Creating Proteins That have New Binding Activities," *TIBS* 23:457-460 (1998).
Taliana et al., "In Vivo Selection of Single-Chain Antibodies Using a Yeast Two-Hybrid System," *Journal of Immunological Methods* 238:161-172 (2000).
Norris et al., "Peptide Antagonists of the Human Estrogen Receptor," *Science* 285:744-746 (1999).
Chen et al., "Transcriptional Activation of the Human Estrogen Receptor by DDT Isomers and Metabolites in Yeast and MCF-7 Cells," *Biochemical Pharmacology* 53:1161-1172 (1997).
Colas et al., "The Impact of Two-Hybrid and Related Methods on Biotechnology," *TIBTech* 16:355-363 (1998).

(Continued)

*Primary Examiner*—Manjunath N Rao
*Assistant Examiner*—Shulamith H Shafer
(74) *Attorney, Agent, or Firm*—Nixon Peabody LLP

(57) ABSTRACT

A method of identifying a polypeptide monobody having target protein binding activity, said method comprising: providing a host cell comprising (i) a reporter gene under control of a 5' regulatory region operable in the host cell, (ii) a first chimeric gene which encodes a first fusion polypeptide comprising a target protein, or fragment thereof, fused to a C-terminus of a DNA-binding domain which binds to the 5' regulatory region of the reporter gene, and (iii) a second chimeric gene which encodes a second fusion polypeptide comprising a polypeptide monobody fused to a transcriptional activation domain; and detecting expression of the reporter gene, which indicates binding of the polypeptide monobody of the second fusion polypeptide to the target protein such that the transcriptional activation domain of the second fusion polypeptide is in sufficient proximity to the DNA-binding domain of the first fusion polypeptide to allow expression of the reporter gene.

20 Claims, 26 Drawing Sheets

OTHER PUBLICATIONS

Fields et al., "A Novel Genetic System to Detect Protein-Protein Interactions," *Nature* 340:245-246 (1989).

Mendelsohn et al., "Applications of Interaction Traps/Two-Hybrid Systems to Biotechnology Research," *Biotechnology* 5:482-486 (1994).

Uetz et al., "Systematic and Large-Scale Two-Hybrid Screens," *Current Opinion in Microbiology* 3:303-308 (2000).

Akiko Koide, "Selection of Monobodies that Recognize the Human Estrogen Receptor," University of Rochester Cancer Center 5th Annual Scientific Symposium, Oct. 3, 2000, Abstract only.

* cited by examiner

NdeI
CATATGCAGGTTTCTGATGTTCCGCGTGACCTGGAAGTTGTTGCTGCGACCCCGACTAGC
　　MetGlnValSerAspValProArgAspLeuGluValValAlaAlaThrProThrSer
　　-2 -1  1                                              10

BclI PvuII        PstI                                          BsiWI
CTGCTGATCAGCTGGATGCTCCTGCAGTTACCGTGCGTTATTACCGTATCACGTACGGT
LeuLeuIleSerTrpAspAlaProAlaValThrValArgTyrTyrArgIleThrTyrGly
                    20                           30

EcoRI
GAAACCGGTGGTAACTCCCCGGTTCAGGAATTCACTGTACCTGGTTCCAAGTCTACTGCT
GluThrGlyGlyAsnSerProValGlnGluPheThrValProGlySerLysSerThrAla
              40                            50

SalI                 Bst1107I
ACCATCAGCGGCCTGAAACCGGGTGTCGACTATACCATCACTGTATACGCTGTTACTGGC
ThrIleSerGlyLeuLysProGlyValAspTyrThrIleThrValTyrAlaValThrGly
              60                            70

SacI
XhoI
CGTGGTGACAGCCCAGCGAGCTCCAAGCCAATCTCGATTAACTACCGTACCTAGTAACTC
ArgGlyAspSerProAlaSerSerLysProIleSerIleAsnTyrArgThr
              80                            90

BamHI
GAGGATCC

*FIG. 2*

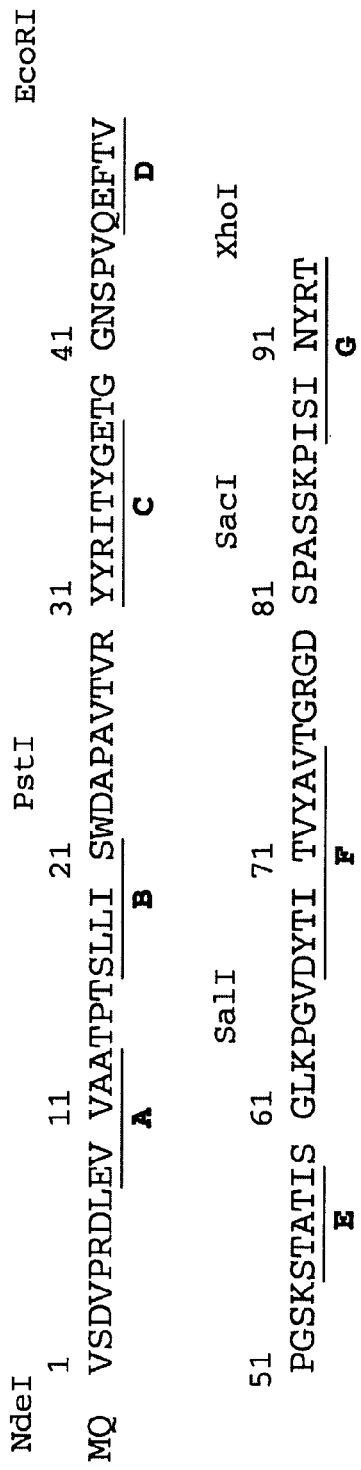
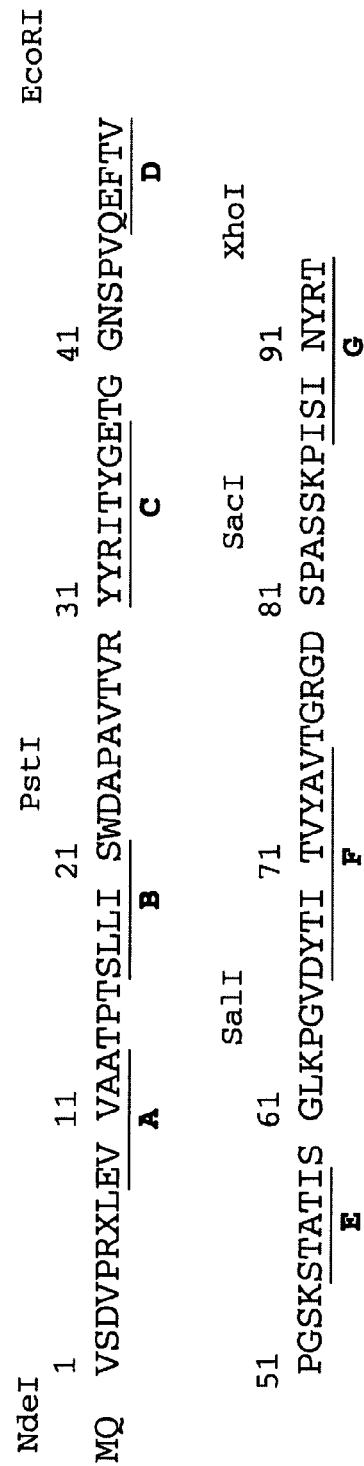
FIG. 3A
FIG. 3B

ATGGACTACAAGGACGACGATGACAAGGGTATGCAGGTTTCTGATGTTCCGACCGACCTG
MetAspTyrLysAspAspAspAspLysGly<u>MetGlnValSerAspValProThrAspLeu</u>

```
                                     PvuII
GAAGTTGTTGCTGCGACCCCGACTAGCCTGCTGATCAGCTGGGATGCTCCTNNKNNKNNK
```
<u>GluValValAlaAlaThrProThrSerLeuLeuIleSerTrpAspAlaPro</u>XaaXaaXaa

```
                                                          EcoRI
NNKNNKNNKTATTACCGTATCACGTACGGTGAAACCGGTGGTAACTCCCCGGTTCAGGAATTC
```
XaaXaa<u>TyrTyrArgIleThrTyrGlyGluThrGlyGlyAsnSerProValGlnGluPhe</u>

```
                                                    SalI
ACTGTACCTGGTTCCAAGTCTACTGCTACCATCAGCGGCCTGAAACCGGGTGTCGACTAT
```
<u>ThrValProGlySerLysSerThrAlaThrIleSerGlyLeuLysProGlyValAspTyr</u>

ACCATCACTGTATACGCTGTTACTGGCNNKNNKNNKNNKNNKNNKNNKTCCAAGCCAATC
<u>ThrIleThrValTyrAlaValThrGly</u>XaaXaaXaaXaaXaaXaaXaaSerLysProIle

```
            KpnI
TCGATTAACTACCGTACCAGTGGTACCGGTGGTTCCCCTCCAAAAAAGAAGAGAAAGGTA
```
<u>SerIleAsnTyrArgThr</u>SerGlyThrGlyGlySerProProLysLysLysArgLysVal

GCTGGTATCAATAAAGATATCGAGGAGTGCAATGCCATCATTGAGCAGTTTATCGACTAC
AlaGlyIleAsnLysAspIleGluGluCysAsnAlaIleIleGluGlnPheIleAspTyr

CTGCGCACCGGACAGGAGATGCCGATGGAAATGGCGGATCAGGCGATTAACGTGGTGCCG
LeuArgThrGlyGlnGluMetProMetGluMetAlaAspGlnAlaIleAsnValValPro

GGCATGACGCCGAAAACCATTCTTCACGCCGGGCCGCCGATCCAGCCTGACTGGCTGAAA
GlyMetThrProLysThrIleLeuHisAlaGlyProProIleGlnProAspTrpLeuLys

TCGAATGGTTTTCATGAAATTGAAGCGGATGTTAACGATACCAGCCTCTTGCTGAGTGGA
SerAsnGlyPheHisGluIleGluAlaAspValAsnAspThrSerLeuLeuLeuSerGly

```
    XhoI  SphI
GATTAACTCGAGGCATGC
Asp•••
```

FIG. 5

```
ATGGGTAAGCCTATCCCTAACCCTCTCCTCGGTCTCGATTCTACACAAGCTATGGGTGCT
MetGlyLysProIleProAsnProLeuLeuGlyLeuAspSerThrGlnAlaMetGlyAla

CCTCCAAAAAAGAAGAGAAAGGTAGCTGGTATCAATAAAGATATCGAGGAGTGCAATGCC
ProProLysLysLysArgLysValAlaGlyIleAsnLysAspIleGluGluCysAsnAla

ATCATTGAGCAGTTTATCGACTACCTGCGCACCGGACAGGAGATGCCGATGGAAATGGCG
IleIleGluGlnPheIleAspTyrLeuArgThrGlyGlnGluMetProMetGluMetAla

GATCAGGCGATTAACGTGGTGCCGGGCATGACGCCGAAAACCATTCTTCACGCCGGGCCG
AspGlnAlaIleAsnValValProGlyMetThrProLysThrIleLeuHisAlaGlyPro

CCGATCCAGCCTGACTGGCTGAAATCGAATGGTTTTCATGAAATTGAAGCGGATGTTAAC
ProIleGlnProAspTrpLeuLysSerAsnGlyPheHisGluIleGluAlaAspValAsn
                                                         KpnI
                                    HindIII      SacI
GATACCAGCCTCTTGCTGAGTGGAGATGCCTCCAAGCTTGGTACCGAGCTCGGATCTATG
AspThrSerLeuLeuLeuSerGlyAspAlaSerLysLeuGlyThrGluLeuGlySerMet CAGGTTTCTGATGTTCCGACCGACCTGGAAGTTGTTGCTGCGACCCCGNNSNNSNNSNNS
GlnValSerAspValProThrAspLeuGluValValAlaAlaThrProXaaXaaXaaXaa PvuII         PstI
NNSNNSNNSACTAGCCTGCTGATCAGCTGGGATGCTCCTGCAGTTACCGTGCGTTATTAC
XaaXaaXaaThrSerLeuLeuIleSerTrpAspAlaProAlaValThrValArgTyrTyr EcoRI
CGTATCACGTACGGTGAAACCGGTGGTAACTCCCCGGTTCAGGAATTCACTGTACCTGGT
ArgIleThrTyrGlyGluThrGlyGlyAsnSerProValGlnGluPheThrValProGly SalI
TCCAAGTCTACTGCTACCATCAGCGGCCTGAAACCGGGTGTCGACTATACCATCACTGTA
SerLysSerThrAlaThrIleSerGlyLeuLysProGlyValAspTyrThrIleThrVal SacI
TACGCTGTTACTGGCCGTGGTGACAGCCCAGCGAGCTCCAAGCCAATCTCGATTAACTAC
TyrAlaValThrGlyArgGlyAspSerProAlaSerSerLysProIleSerIleAsnTyr XhoI  SphI
CGTACCTAGTAACTCGAGGCATGC
ArgThr••••••
```

FIG. 6

ATGGGTAAGCCTATCCCTAACCCTCTCCTCGGTCTCGATTCTACACAAGCTATGGGTGCT
MetGlyLysProIleProAsnProLeuLeuGlyLeuAspSerThrGlnAlaMetGlyAla

CCTCCAAAAAAGAAGAGAAAGGTAGCTGGTATCAATAAAGATATCGAGGAGTGCAATGCC
ProProLysLysLysArgLysValAlaGlyIleAsnLysAspIleGluGluCysAsnAla

ATCATTGAGCAGTTTATCGACTACCTGCGCACCGGACAGGAGATGCCGATGGAAATGGCG
IleIleGluGlnPheIleAspTyrLeuArgThrGlyGlnGluMetProMetGluMetAla

GATCAGGCGATTAACGTGGTGCCGGGCATGACGCCGAAAACCATTCTTCACGCCGGGCCG
AspGlnAlaIleAsnValValProGlyMetThrProLysThrIleLeuHisAlaGlyPro

CCGATCCAGCCTGACTGGCTGAAATCGAATGGTTTTCATGAAATTGAAGCGGATGTTAAC
ProIleGlnProAspTrpLeuLysSerAsnGlyPheHisGluIleGluAlaAspValAsn
                                                         KpnI
                              HindIII        SacI
GATACCAGCCTCTTGCTGAGTGGAGATGCCTCCAAGCTTGGTACCGAGCTCGGATCTATG
AspThrSerLeuLeuLeuSerGlyAspAlaSerLysLeuGlyThrGluLeuGlySerMet CAGGTTTCTGATGTTCCGACCGACCTGGAAGTTGTTGCTGCGACCCCGACTAGCCTGCTG
GlnValSerAspValProThrAspLeuGluValValAlaAlaThrProThrSerLeuLeu PvuII
ATCAGCTGGGATGCTCCTNNKNNKNNKNNKNNKTATTACCGTATCACGTACGGTGAAACC
IleSerTrpAspAlaProXaaXaaXaaXaaXaaTyrTyrArgIleThrTyrGlyGluThr EcoRI
GGTGGTAACTCCCCGGTTCAGGAATTCACTGTACCTGGTTCCAAGTCTACTGCTACCATC
GlyGlyAsnSerProValGlnGluPheThrValProGlySerLysSerThrAlaThrIle SalI
AGCGGCCTGAAACCGGGTGTCGACTATACCATCACTGTATACGCTGTTACTGGCNNKNNK
SerGlyLeuLysProGlyValAspTyrThrIleThrValTyrAlaValThrGlyXaaXaa XhoI  SphI
NNKNNKNNKNNKNNKNNKTCCAAGCCAATCTCGATTAACTACCGTACCTAGTAACTCGAGGCA
XaaXaaXaaXaaXaaSerLysProIleSerIleAsnTyrArgThr••••••

TGCATCTAGAGGGCCGCATCATGTAATTAGTTATGTCACGCTTA

*FIG. 7*

```
ATGGGTAAGCCTATCCCTAACCCTCTCCTCGGTCTCGATTCTACACAAGCTATGGGTGCT
MetGlyLysProIleProAsnProLeuLeuGlyLeuAspSerThrGlnAlaMetGlyAla

CCTCCAAAAAAGAAGAGAAAGGTAGCTGGTATCAATAAAGATATCGAGGAGTGCAATGCC
ProProLysLysLysArgLysValAlaGlyIleAsnLysAspIleGluGluCysAsnAla

ATCATTGAGCAGTTTATCGACTACCTGCGCACCGGACAGGAGATGCCGATGGAAATGGCG
IleIleGluGlnPheIleAspTyrLeuArgThrGlyGlnGluMetProMetGluMetAla

GATCAGGCGATTAACGTGGTGCCGGGCATGACGCCGAAAACCATTCTTCACGCCGGGCCG
AspGlnAlaIleAsnValValProGlyMetThrProLysThrIleLeuHisAlaGlyPro

CCGATCCAGCCTGACTGGCTGAAATCGAATGGTTTTCATGAAATTGAAGCGGATGTTAAC
ProIleGlnProAspTrpLeuLysSerAsnGlyPheHisGluIleGluAlaAspValAsn
                                                KpnI
                               HindIII       SacI
GATACCAGCCTCTTGCTGAGTGGAGATGCCTCCAAGCTTGGTACCGAGCTCGGATCTATG
AspThrSerLeuLeuLeuSerGlyAspAlaSerLysLeuGlyThrGluLeuGlySerMet CGTGTTTCTGATGTTCCGCGTGACCTGGAAGTTGTTGCTGCGACCCCGACTAGCCTGCTG
ArgValSerAspValProArgAspLeuGluValValAlaAlaThrProThrSerLeuLeu PvuII
ATCAGCTGGGATGCTCCTGCAGTTACCGTGCGTTATTACCGTATCACGTACGGTGAAACC
IleSerTrpAspAlaProAlaValThrValArgTyrTyrArgIleThrTyrGlyGluThr EcoRI
GGTGGTAACTCCCCGGTTCAGGAATTCACTGTACCTGGTTCCAAGTCTACTGCTACCATC
GlyGlyAsnSerProValGlnGluPheThrValProGlySerLysSerThrAlaThrIle SalI
AGCGGCCTGAAACCGGGTGTCGACTATACCATCACTGTATACGCTGTTACTGGCNNKNNK
SerGlyLeuLysProGlyValAspTyrThrIleThrValTyrAlaValThrGlyXaaXaa NNKNNKNNKNNKNNKNNKNNKNNKNNKNNKNNKNNKNNKAAGCCAATCTCGATTAAC
XaaXaaXaaXaaXaaXaaXaaXaaXaaXaaXaaXaaXaaLysProIleSerIleAsn XhoI   SphI
TACCGTACCTAGTAACTCGAGGCATGC
TyrArgThr······
```

*FIG. 8*

```
ATGGGTAAGCCTATCCCTAACCCTCTCCTCGGTCTCGATTCTACACAAGCTATGGGTGCT
MetGlyLysProIleProAsnProLeuLeuGlyLeuAspSerThrGlnAlaMetGlyAla

CCTCCAAAAAAGAAGAGAAAGGTAGCTGGTATCAATAAAGATATCGAGGAGTGCAATGCC
ProProLysLysLysArgLysValAlaGlyIleAsnLysAspIleGluGluCysAsnAla

ATCATTGAGCAGTTTATCGACTACCTGCGCACCGGACAGGAGATGCCGATGGAAATGGCG
IleIleGluGlnPheIleAspTyrLeuArgThrGlyGlnGluMetProMetGluMetAla

GATCAGGCGATTAACGTGGTGCCGGGCATGACGCCGAAAACCATTCTTCACGCCGGGCCG
AspGlnAlaIleAsnValValProGlyMetThrProLysThrIleLeuHisAlaGlyPro

CCGATCCAGCCTGACTGGCTGAAATCGAATGGTTTTCATGAAATTGAAGCGGATGTTAAC
ProIleGlnProAspTrpLeuLysSerAsnGlyPheHisGluIleGluAlaAspValAsn

HindIII/KpnI/SacI
GATACCAGCCTCTTGCTGAGTGGAGATGCCTCCAAGCTTGGTACCGAGCTCGGATCTATG
AspThrSerLeuLeuLeuSerGlyAspAlaSerLysLeuGlyThrGluLeuGlySerMet CAGGTTTCTGATGTTCCGACCGACCTGGAAGTTGTTGCTGCGACCCCGACTAGCCTGCTG
GlnValSerAspValProThrAspLeuGluValValAlaAlaThrProThrSerLeuLeu PvuII         PstI
ATCAGCTGGGATGCTCCTGCAGTTACCGTGCGTTATTACCGTATCACGTACGGTGAAACC
IleSerTrpAspAlaProAlaValThrValArgTyrTyrArgIleThrTyrGlyGluThr EcoRI
GGTGGTAACTCCCCGGTTCAGGAATTCACTGTACCTGGTTCCAAGTCTACTGCTACCATC
GlyGlyAsnSerProValGlnGluPheThrValProGlySerLysSerThrAlaThrIle SalI
AGCGGCCTGAAACCGGGTGTCGACTATACCATCACTGTATACGCTGTTACTGGCCGTGGT
SerGlyLeuLysProGlyValAspTyrThrIleThrValTyrAlaValThrGlyArgGly SacI                                       XhoI   SphI
GACAGCCCAGCGAGCTCCAAGCCAATCTCGATTAACTACCGTACCTAGTAACTCGAGGCA
AspSerProAlaSerSerLysProIleSerIleAsnTyrArgThr******

TGC
```

FIG. 10

ATGAAAGCGTTAACGGCCAGGCAACAAGAGGTGTTTGATCTCATCCGTGATCACATCAGC
MetLysAlaLeuThrAlaArgGlnGlnGluValPheAspLeuIleArgAspHisIleSer

CAGACAGGTATGCCGCCGACGCGTGCGGAAATCGCGCAGCGTTTGGGGTTCCGTTCCCCA
GlnThrGlyMetProProThrArgAlaGluIleAlaGlnArgLeuGlyPheArgSerPro

AACGCGGCTGAAGAACATCTGAAGGCGCTGGCACGCAAAGGCGTTATTGAAATTGTTTCC
AsnAlaAlaGluGluHisLeuLysAlaLeuAlaArgLysGlyValIleGluIleValSer

GGCGCATCACGCGGGATTCGTCTGTTGCAGGAAGAGGAAGAAGGGTTGCCGCTGGTAGGT
GlyAlaSerArgGlyIleArgLeuLeuGlnGluGluGluGluGlyLeuProLeuValGly cgtgtggctgccggtgaaccacttctggcgcaacagcatattgaaggtcattatcaggtc
ArgValAlaAlaGlyGluProLeuLeuAlaGlnGlnHisIleGluGlyHisTyrGlnVal GATCCTTCCTTATTCAAGCCGAATGCTGATTTCCTGCTGCGCGTCAGCGGGATGTCGATG
AspProSerLeuPheLysProAsnAlaAspPheLeuLeuArgValSerGlyMetSerMet AAAGATATCGGCATTATGGATGGTGACTTGCTGGCAGTGCATAAAACTCAGGATGTACGT
LysAspIleGlyIleMetAspGlyAspLeuLeuAlaValHisLysThrGlnAspValArg AACGGTCAGGTCGTTGTCGCACGTATTGATGACGAAGTTACCGTTAAGCGCCTGAAAAAA
AsnGlyGlnValValValAlaArgIleAspAspGluValThrValLysArgLeuLysLys CAGGGCAATAAAGTCGAACTGTTGCCAGAAAATAGCGAGTTTAAACCAATTGTCGTAGAT
GlnGlyAsnLysValGluLeuLeuProGluAsnSerGluPheLysProIleValValAsp CTTCGTCAGCAGAGCTTCACCATTGAAGGGCTGGCGGTTGGGGTTATTCGCAACGGCGAC
LeuArgGlnGlnSerPheThrIleGluGlyLeuAlaValGlyValIleArgAsnGlyAsp
                SacI
    EcoRI HindIII
TGGCTGGAATTCAAGCTTGAGCTCGGCGGCAGCGGTATGATCAAACGCTCTAAGAAGAAC
TrpLeuGluPheLysLeuGluLeuGlyGlySerGlyMetIleLysArgSerLysLysAsn AGCCTGGCCTTGTCCCTGACGGCCGACCAGATGGTCAGTGCCTTGTTGGATGCTGAGCCC
SerLeuAlaLeuSerLeuThrAlaAspGlnMetValSerAlaLeuLeuAspAlaGluPro HindIII
CCCATACTCTATTCCGAGTATGATCCTACCAGACCCTTCAGTGAAGCTTCGATGATGGGC
ProIleLeuTyrSerGluTyrAspProThrArgProPheSerGluAlaSerMetMetGly

*FIG. 12A*

```
TTACTGACCAACCTGGCAGACAGGGAGCTGGTTCACATGATCAACTGGGCGAAGAGGGTG
LeuLeuThrAsnLeuAlaAspArgGluLeuValHisMetIleAsnTrpAlaLysArgVal

XbaI
CCAGGCTTTGTGGATTTGACCCTCCATGATCAGGTCCACCTTCTAGAATGTGCCTGGCTA
ProGlyPheValAspLeuThrLeuHisAspGlnValHisLeuLeuGluCysAlaTrpLeu

GAGATCCTGATGATTGGTCTCGTCTGGCGCTCCATGGAGCACCCAGTGAAGCTACTGTTT
GluIleLeuMetIleGlyLeuValTrpArgSerMetGluHisProValLysLeuLeuPhe

GCTCCTAACTTGCTCTTGGACAGGAACCAGGGAAAATGTGTAGAGGGCATGGTGGAGATC
AlaProAsnLeuLeuLeuAspArgAsnGlnGlyLysCysValGluGlyMetValGluIle

PstI
TTCGACATGCTGCTGGCTACATCATCTCGGTTCCGCATGATGAATCTGCAGGGAGAGGAG
PheAspMetLeuLeuAlaThrSerSerArgPheArgMetMetAsnLeuGlnGlyGluGlu

TTTGTGTGCCTCAAATCTATTATTTTGCTTAATTCTGGAGTGTACACATTTCTGTCCAGC
PheValCysLeuLysSerIleIleLeuLeuAsnSerGlyValTyrThrPheLeuSerSer

ACCCTGAAGTCTCTGGAAGAGAAGGACCATATCCACCGAGTCCTGGACAAGATCACAGAC
ThrLeuLysSerLeuGluGluLysAspHisIleHisArgValLeuAspLysIleThrAsp

PstI
ACTTTGATCCACCTGATGGCCAAGGCAGGCCTGACCCTGCAGCAGCAGCACCAGCGGCTG
ThrLeuIleHisLeuMetAlaLysAlaGlyLeuThrLeuGlnGlnGlnHisGlnArgLeu

GCCCAGCTCCTCCTCATCCTCTCCCACATCAGGCACATGAGTAACAAAGGCATGGAGCAT
AlaGlnLeuLeuLeuIleLeuSerHisIleArgHisMetSerAsnLysGlyMetGluHis

CTGTACAGCATGAAGTGCAAGAACGTGGTGCCCCTCTATGACCTGCTGCTGGAGATGCTG
LeuTyrSerMetLysCysLysAsnValValProLeuTyrAspLeuLeuLeuGluMetLeu

GACGCCCACCGCCTACATGCGCCCACTAGCCGTGGAGGGGCATCCGTGGAGGAGACGGAC
AspAlaHisArgLeuHisAlaProThrSerArgGlyGlyAlaSerValGluGluThrAsp

CAAAGCCACTTGGCCACTGCGGGCTCTACTTCATCGCATTCCTTGCAAAAGTATTACATC
GlnSerHisLeuAlaThrAlaGlySerThrSerSerHisSerLeuGlnLysTyrTyrIle

XhoI
ACGGGGGAGGCAGAGGGTTTCCCTGCCACAGTCTGACtcgag
ThrGlyGluAlaGluGlyPheProAlaThrVal•••
```

*FIG. 12B*

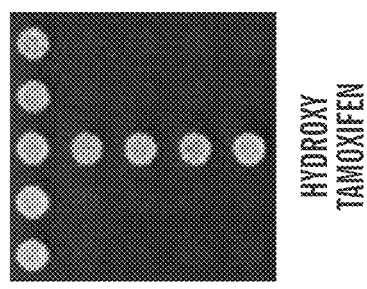
FIG. 17D HYDROXY TAMOXIFEN
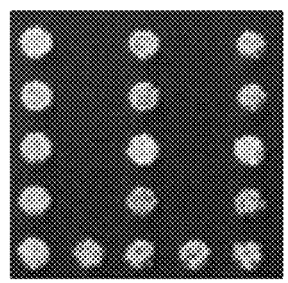
FIG. 17C ESTRADIOL
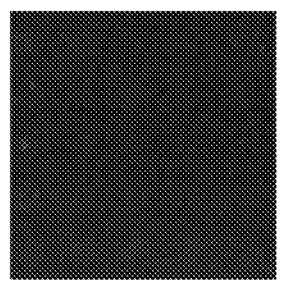
FIG. 17B NO LIGAND
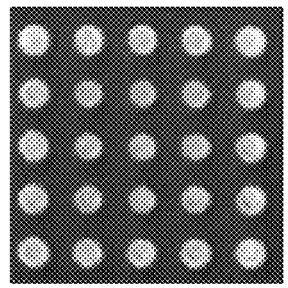
FIG. 17A NO SELECTION (MASTER PLATE)

METHOD OF IDENTIFYING POLYPEPTIDE MONOBODIES WHICH BIND TO TARGET PROTEINS AND USE THEREOF

This application claims the benefit of U.S. Provisional Patent Application Ser. No. 60/249,756, filed Nov. 17, 2000, which is hereby incorporated by reference in its entirety.

This invention was made with government support under R29-GM55042 awarded by the National Institutes of Health and DMAD17-97-1-7295 awarded by the U.S. Army. The government has certain rights in the invention.

FIELD OF THE INVENTION

The present invention relates generally to polypeptide monobodies, more particularly polypeptide monobodies derived from the tenth fibronectin type III domain from human fibronectin ("FNfn10"), as well as methods of identifying such monobodies having target protein binding activity, and the use thereof for modulating target activity.

BACKGROUND OF THE INVENTION

Many biological processes are regulated by proteins. Regulatory proteins undergo conformational changes to alter their interactions with partners and/or alter their catalytic efficiency. Thus, it is essential to detect conformational changes of proteins in order to understand the molecular mechanism underlying their functions. Although a large body of in vitro studies has revealed conformational changes of proteins, there are no established techniques to monitor protein conformational changes in the cellular environment. Biophysical measurements, such as X-ray crystallography, nuclear magnetic resonance, and other spectroscopies, typically require purified samples and conditions that are drastically different from those inside the cells. It is generally accepted that the "molecular crowding" within the cellular environment can significantly affect ligand binding, catalysis, stability and folding of macromolecules (Minton, 2000). For example, the structures and the relative populations of "active" and "inactive" conformations of a protein may be quite different from those determined using in vitro biophysical methods. Therefore, it would be of great value to establish a strategy to probe conformations of proteins in living cells.

An alternative approach to direct structure determination is the use of conformation-specific probes. Anfinsen and others used conformation-specific antibodies to demonstrate reversible unfolding of ribonuclease in in vitro experiments (Sachs et al., 1972). Thus, it is conceivable that one can introduce conformation-specific probes, such as antibodies, inside cells and determine their respective binding affinity to a target to probe conformational changes of the target. To implement this strategy, one must first obtain conformation-specific probes and establish detection methods for probe binding. However, antibodies and their fragments usually require the formation of disulfide bonds for proper folding and, thus, they do not always function in the reducing environment inside cells. Also, no general methods are available to generate conformation-specific antibodies. Short peptides may also be used, but they tend to be rapidly degraded in cells due to their low resistance to proteolysis.

Antibody-mimics, termed "monobodies", formed using a small β-sheet protein scaffold such as the tenth fibronectin type m domain from human fibronectin (FNfn10) have been previously described (Koide et al., 1998). It was shown that monobodies with a novel binding function can be engineered by screening phage-display libraries of FNfn10 in which loop regions are diversified. FNfn10 does not contain disulfide bonds or metal binding sites, is highly stable and undergoes reversible unfolding (Koide et al., 1998; Main et al., 1992; Plaxco et al., 1996). While the stability of monobodies makes them well suited for intracellular studies, there has been no use of monobodies to probe conformations of proteins in living cells.

A number of disease states are dependent upon nuclear receptor activity and conformation. For example, human estrogen receptor α (ERα) normally regulates the growth and differentiation of the female reproductive system and those of skeletal, neural, and cardiovascular tissues in both males and females (Korach, 1994). Yet ERα is a therapeutic target of, and a clinical marker for, estrogen-responsive breast tumor (Jordan et al., 1992). A diverse group of ligands, including antiestrogens that are in clinical use, exist which modulate ER transcriptional activation and the physiological response of the hormone 17β-estradiol (E2) (Anstead et al., 1997). Because the conformation of ERα as it is involved in disease state is unknown, it would be desirable to identify an approach to rapidly classify ERα conformation as well as develop a preliminary screening tool for estrogen- and antiestrogen-like molecules. Any approach which would function to classify ERα conformation and screen estrogen- and antiestrogen-like molecules should also be able to be operable with other nuclear receptors: classifying their conformations and screening their agonists and antagonists.

In addition to screening, another important feature in drug discovery is target validation. The majority of target validation methods are based on nucleic acid techniques. These include gene knockout (the gene coding for the protein of interest is eliminated from the genome of the organism) and antisense DNA (DNA that hybridize to the messenger RNA of the protein of interest is produced in the cell to inhibit the expression of the protein). These techniques are limited in that some genes are essential for the growth of the organism and cannot be deleted, and the effect of deleting a protein may be different from inhibiting its function (sometimes only partially) with drugs.

Recently, however, a few methods based on protein technologies have been reported (Mhashilkar et al., 1995; Richardson et al., 1995; Colas et al., 1996; Cochet et al., 1998; Colas & Brent, 1998; Fabbrizio et al., 1999; Norris et al., 1999). Proteins or peptides that bind to the protein of interest ("peptide aptamers") are first isolated (typically using combinatorial library screening). Then the peptide aptamer is introduced into the organism of interest (typically using an expression vector), and the effect(s) of the aptamer is analyzed. For peptide aptamers, constrained peptides that are displayed on a protein (Colas et al., 1996; Fabbrizio et al., 1999), linear peptides (Norris et al., 1999), and antibody fragments (Mhashilkar et al., 1995) have been reported. Though these approaches have been at least in some sense successful, they have their limitations. The first two methods use only one contiguous segment of peptides for binding, and thus the binding interface achieved by these methods is limited. Antibody fragments (e.g, single-chain Fv and Fab) contain disulfide bonds, and these disulfide bonds are important for the stability of antibody fragments. The cytoplasm of the cell is generally a reducing environment, making it difficult to maintain the active conformation of antibody fragments. Thus, antibody fragments expressed in the cytoplasm are not always functional (Cochet et al., 1998).

The present invention overcomes these and other deficiencies in the art.

SUMMARY OF THE INVENTION

A first aspect of the present invention relates to a fibronectin type III (Fn3) polypeptide monobody including: at least two Fn3 β-strand domain sequences with a loop region sequence linked between adjacent β-strand domain sequences; and optionally, an N-terminal tail of at least about 2 amino acids, a C-terminal tail of at least about 2 amino acids, or both; wherein at least one loop region sequence, the N-terminal tail, or the C-terminal tail comprises an amino acid sequence which varies by deletion, insertion, or replacement of at least two amino acids from a corresponding loop region, N-terminal tail, or C-terminal tail in a wild-type Fn3 domain of fibronectin, and wherein the polypeptide monobody exhibits nuclear receptor binding activity.

A second aspect of the present invention relates to a fusion protein which includes a first portion including a polypeptide monobody of the present invention and a second portion fused to the first portion.

A third aspect of the present invention relates to a DNA molecule encoding a polypeptide monobody of the present invention, as well as expression vectors and host cells which contain such DNA molecules.

A fourth aspect of the present invention relates to a combinatorial library including: a plurality of fusion polypeptides each including a transcriptional activation domain fused to a distinct fibronectin type III (Fn3) polypeptide monobody, the polypeptide monobody including (i) at least two Fn3 β-strand domain sequences, (ii) a loop region sequence linked between adjacent β-strand domain sequences, and (iii) optionally, an N-terminal tail of at least about 2 amino acids, a C-terminal tail of at least about 2 amino acids, or both, wherein at least one loop region sequence, the N-terminal tail, or the C-terminal tail includes a combinatorial amino acid sequence which varies by deletion, insertion, or replacement of at least two amino acids from a corresponding loop region, N-terminal tail, or C-terminal tail in a wild-type Fn3 domain of fibronectin.

A fifth aspect of the present invention relates to an in vivo composition including: a fusion polypeptide of the combinatorial library of the present invention; a reporter gene under control of a 5' regulatory region; and a chimeric gene which encodes a second fusion polypeptide including a target protein, or fragment thereof, fused to the C-terminus of a DNA-binding domain which binds to the 5' regulatory region of the reporter gene, wherein binding of the polypeptide monobody of the fusion polypeptide to the target protein, or fragment thereof, of the second fusion polypeptide brings the transcriptional activation domain of the fusion polypeptide in sufficient proximity to the DNA-binding domain of the second fusion polypeptide to induce expression of the reporter gene.

A sixth aspect of the present invention relates to a method of identifying a polypeptide monobody having target protein binding activity, which method includes: providing a host cell including (i) a reporter gene under control of a 5' regulatory region operable in the host cell, (ii) a first chimeric gene which encodes a first fusion polypeptide including a target protein, or fragment thereof, fused to a C-terminus of a DNA-binding domain which binds to the 5' regulatory region of the reporter gene, and (iii) a second chimeric gene which encodes a second fusion polypeptide including a polypeptide monobody fused to a transcriptional activation domain; and detecting expression of the reporter gene, which indicates binding of the polypeptide monobody of the second fusion polypeptide to the target protein such that the transcriptional activation domain of the second fusion polypeptide is in sufficient proximity to the DNA-binding domain of the first fusion polypeptide to allow expression of the reporter gene.

A seventh aspect of the present invention relates to a method of screening a candidate drug for nuclear receptor agonist or antagonist activity, which method includes: providing a host cell including (i) a reporter gene under control of a 5' regulatory region, (ii) a first chimeric gene which encodes a first fusion polypeptide including a nuclear receptor, or fragment thereof including a ligand-binding domain, fused to a C-terminus of a DNA-binding domain which binds to the 5' regulatory region of the reporter gene, and (iii) a second chimeric gene which encodes a second fusion polypeptide including a polypeptide sequence fused to a transcriptional activation domain, the polypeptide sequence binding to the nuclear receptor, or fragment thereof, in the absence of both an agonist and an antagonist of the nuclear receptor, presence of an agonist of the nuclear receptor, presence of an antagonist of the nuclear receptor, or presence of both an agonist and an antagonist of the nuclear receptor; growing the host cell in a growth medium comprising a candidate drug; and detecting expression of the reporter gene, which indicates binding of the polypeptide sequence of the second fusion polypeptide to the nuclear receptor, or fragment thereof, such that the transcriptional activation domain of the second fusion polypeptide is in sufficient proximity to the DNA-binding domain of the first fusion polypeptide to allow expression of the reporter gene, wherein modulation of reporter gene expression indicates that the candidate drug is either an agonist or an antagonist, or has mixed activity.

An eighth aspect of the present invention relates to a kit including: a culture system which includes a culture medium on which has been placed at least one type of transformed host cell, each of the at least one type of transformed host cell comprising (i) a reporter gene under control of a 5' regulatory region, (ii) a first chimeric gene which encodes a first fusion polypeptide comprising a nuclear receptor, or fragment thereof including a ligand-binding domain, fused to a C-terminus of a DNA-binding domain which binds to the 5' regulatory region of the reporter gene, and (iii) a second chimeric gene which encodes a second fusion polypeptide comprising a polypeptide sequence fused to a transcriptional activation domain, the polypeptide sequence binding to the nuclear receptor, or fragment thereof, in the absence of both an agonist and an antagonist of the nuclear receptor, presence of an agonist of the nuclear receptor, presence of an antagonist of the nuclear receptor, or presence of both an agonist and an antagonist of the nuclear receptor.

A ninth aspect of the present invention relates to a kit including: a plurality of host cells, each including a reporter gene under control of a 5' regulatory region and a heterologous DNA molecule encoding a first fusion polypeptide including a nuclear receptor, or fragment thereof which includes a ligand-binding domain, fused to a C-terminus of a DNA-binding domain which binds to the 5' regulatory region of the reporter gene; and a vector including a DNA molecule encoding a second fusion polypeptide including a transcriptional activation domain fused to a polypeptide monobody; wherein upon mutation of the DNA molecule to encode a mutant polypeptide antibody and wherein upon introduction of the vector into at least a portion of said plurality of host cells, expression of the reporter gene is induced upon binding of the polypeptide monobody of the second fusion polypeptide to the nuclear receptor, or fragment thereof, of the first fusion polypeptide such that the transcriptional activation domain of the second fusion polypeptide is in sufficient proximity to the DNA-binding domain of the first fusion polypeptide.

A tenth aspect of the present invention relates to a method of validating target protein activity which includes: exposing a target protein to a polypeptide monobody which binds to the target protein and determining whether binding of the target protein by the polypeptide monobody modifies target protein activity.

An eleventh aspect of the present invention relates to a method of measuring polypeptide monobody binding affinity for a target protein, which method includes: exposing a target protein to an interaction partner which binds the target protein and a polypeptide monobody which binds the target protein; and measuring the degree to which the polypeptide monobody competes with the interaction partner.

A twelfth aspect of the present invention relates to a method of modulating target protein activity which includes: exposing a target protein to a polypeptide monobody which binds the target protein under conditions effective to modify target protein activity.

The two-hybrid system is particularly suitable for the purpose of identifying polypeptide monobodies which have activity in binding a target protein such as a nuclear receptor. In addition, the two-hybrid system can also be used during validation of polypeptide monobody affinity for a target protein and its measuring its ability to modulate activity of the target protein. By identifying polypeptides that can detect conformational changes on target proteins such as nuclear receptors, the present invention allows for drug screening to determine whether candidate drug or potentially toxic agents are likely to have the capability to modify nuclear receptor activity, either as an agonist, an antagonist, or simply an inactive inhibitor of the nuclear receptor. Thus, the polypeptide monobodies which bind to the different conformations of the nuclear receptor can be used immediately in assays described herein. Moreover, polypeptide monobodies which have activity in modifying nuclear receptor activity can be used for therapeutic uses in the treatment of nuclear receptor-related diseases or conditions.

BRIEF DESCRIPTION OF THE DRAWINGS

FIG. 2 illustrates a nucleotide sequence (SEQ ID No: 1) encoding the amino acid sequence (SEQ ID No: 2) of the wild-type FNfn10. The amino acid numbering is according to Main et al. (1992). The BC loop region and the FG loop region are shown in boxes.

FIGS. 3A-B illustrate the amino acid sequence of the wild-type FNfn10 (SEQ ID No: 2, FIG. 3A) as well as a mutant FNfn10 (SEQ ID No: 3, FIG. 3B) which has the Asp-7 residue replaced with a non-negatively charged amino acid residue (X), which is preferably either Asn or Lys. As reported in Koide et al. (2001), both of these mutations have the effect of promoting greater stability of the mutant FNfn40 at neutral pH as compared to the wild-type FNfn10.

FIG. 5 illustrates the nucleotide sequence (SEQ ID No: 4) for the coding region of an exemplary prey fusion protein. The FNfn10-B42 fusion protein (SEQ ID No: 5) was prepared in the library designated pFNB42B5F7. The nucleotide sequence that was diversified in this library is shown in bold. The amino acid sequence of the combinatorial FNfn10 (underlined, SEQ ID No: 6) is shown fused N-terminal to the B42 activation domain. This is opposite to the orientation shown in FIG. 5, although either orientation can be utilized. N denotes a mixture of A, T, G, and C; K denotes a mixture of G and T; and Xaa denotes any amino acid residue.

FIG. 6 illustrates the nucleotide sequence (SEQ ID No: 7) for the coding region of another exemplary prey fusion protein. The FNfn10-B42 fusion protein (SEQ ID No: 8) was prepared in the library designated pYT45AB7N. The nucleotide sequence region that was diversified in this library is shown in bold. This library was constructed by inserting seven diversified residues between Pro15 and Thr16 in the AB loop (residue numbering according to Koide et al., 1998). The amino acid sequence of the combinatorial FNfn10 (underlined, SEQ ID No: 9) is shown fused C-terminal to the B42 activation domain. N denotes a mixture of A, T, G, and C; S denotes a mixture of G and C; and Xaa denotes any amino acid residue.

FIG. 7 illustrates the nucleotide sequence (SEQ ID No: 10) for the coding region of another exemplary prey fusion protein. The FNfn10-B42 fusion protein (SEQ ID No: 11) was prepared in the library designated pYT45B3F7. The nucleotide sequence region that was diversified in this library is shown in bold. The amino acid sequence of the combinatorial FNfn10 (underlined, SEQ ID No: 12) is shown fused C-terminal to the B42 activation domain. N denotes a mixture of A, T, G, and C; K denotes a mixture of G and T; and Xaa denotes any amino acid residue.

FIG. 8 illustrates the nucleotide sequence (SEQ ID No: 13) for the coding region of another exemplary prey fusion protein. The FNfn10-B42 fusion protein (SEQ ID No: 14) was prepared in the library designated pYT47F16. The nucleotide sequence region that was diversified in this library is shown in bold. The amino acid sequence of the combinatorial FNfn10 (underlined, SEQ ID No: 15) is shown fused C-terminal to the B42 activation domain. N denotes a mixture of A, T, G, and C; K denotes a mixture of G and T; and Xaa denotes any amino acid residue.

FIG. 10 illustrates the nucleotide sequence (SEQ ID No: 16) of the B42-FNfn10 fusion protein in the plasmid pYT45 shown in FIG. 9. The amino acid sequence (SEQ ID No: 17) for FNfn10 is underlined.

FIGS. 12A-B illustrate the nucleotide sequence (SEQ ID No: 18) of the LexA-ERα fusion protein in plasmid pEGERα295-595 illustrated in FIG. 11. The amino acid sequence (SEQ ID No: 19) for ERα domains E and F is underlined.

FIG. 13A illustrates schematically the nuclear receptor domain structure: AF-1, ligand-independent activation function; DBD, DNA-binding domain; and AF-2, ligand-dependent activation function. FIGS. 13B-D are schematic drawings of the crystal structures of ERα-LBD illustrating ligand-induced conformational changes. FIGS. 13B-C are from Shiau et al., (1988); and FIG. 13D is from Tanenbaum et al., (1998). Helix 12 is highlighted in black. In FIG. 13B, an LXXLL (SEQ ID No: 20) peptide is bound to the coactivator-binding site, but the peptide is omitted in the figure for clarity. In FIG. 13D, an aberrant intermolecular disulfide bond forces Helix 12 to an extended conformation.

In FIGS. 14A-G, binding specificity toward agonist, antagonist, and selective estrogen receptor modulators ("SERM's") are shown. In FIG. 14H, Western blotting shows that the amount of LexA-ERα-EF was similar in the presence of different ligands.

Abbreviations: ICI, ICI182,780; RAL, raloxifene; PROG, progesterone; and EtOH, no added ligand.

FIGS. 15A-D illustrate in vivo binding specificity of monobodies to different ERα-EF/agonist complexes. Abbreviations: E3, estriol; DES, diethylstilbestrol; GEN, genistein; EtOH, no added ligand.

Figure 16A:
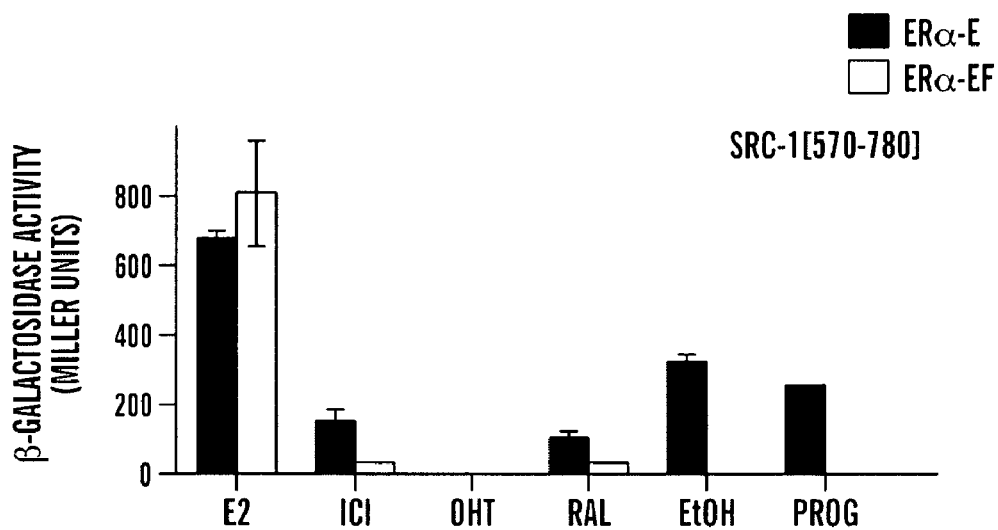
Figure 16B:
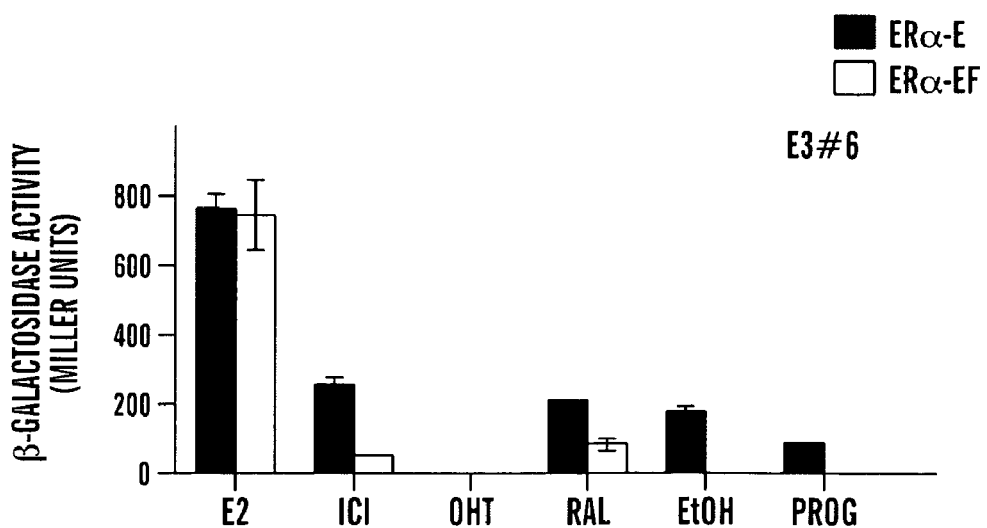
Figure 16C:
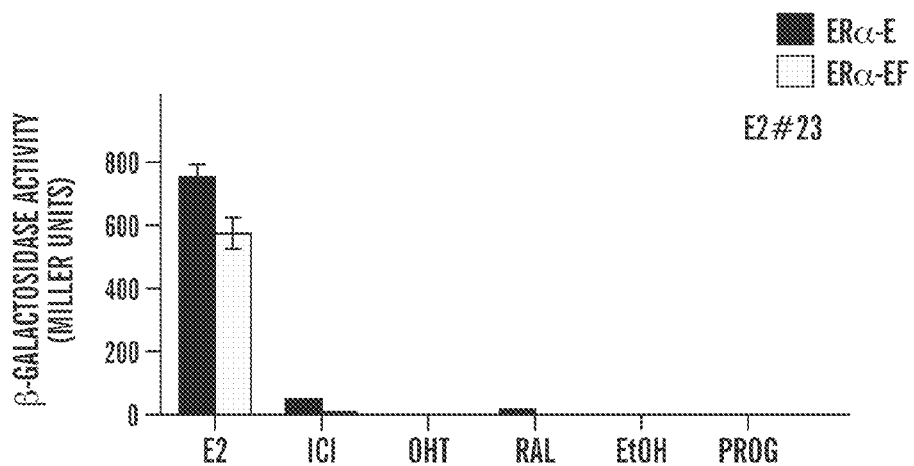
Figure 16D:
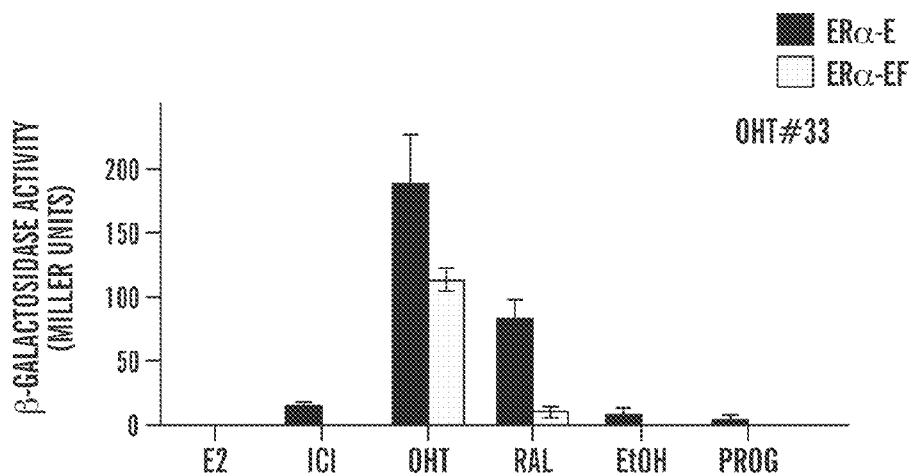
Figure 16E:
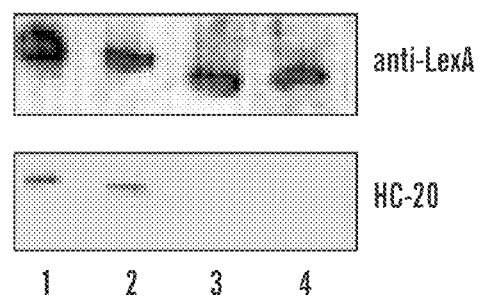

FIGS. 16A-D shows the effects of the F domain on the binding of ERα to SRC-1 and monobodies. Quantitative β-galactosidase assays were performed for yeast two-hybrid strains containing a monobody (or SRC-1)-activation domain fusion and either the ERα-EF or E domain-DNA binding domain fusion proteins. Experiments were performed in the same manner as in FIG. 14. FIG. 16E is a Western blot of yeast cells containing LexA-ERα-EF (lanes 1 and 2) or LexA-ERα-E (lanes 3 and 4) probed with an anti-LexA antibody (top) or anti-ERα-F domain antibody (bottom). Yeast cells were grown in the presence (lanes 1 and 3) and absence (lanes 2 and 4) of E2. Note that these proteins a re expressed at a similar level and lanes 1 and 2 do not contain degradation products similar to LexA-ERα-E (lanes 2 and 4). Abbreviations: ICI ICI182,780; RAL, raloxifene; PROG, progesterone; and EtOH, no added ligand.

FIGS. 17A-D demonstrate the use of a monobody collection as a chemical sensor. Yeast cells containing E2-, OHT-, and (E2 or OHT)-dependent monobodies were strategically placed on 5x5 grids ("No selection"). These cells were stamped on growth selection plates (-leu) containing E2, OHT, or no ligand. White circles are yeast cells grown on a media plate.

FIGS. 18A-D illustrate the in vivo binding specificity of monobody clones, pYT47AB7N-A1 and -B1, as tested using semi-quantitative β-galactosidase assays. Binding specificity toward ER complexed with agonist, antagonist and SERMs, respectively, are shown. The top two panels show results with ERα-EF, while the bottom two show results with ERβ-EF. Abbreviations used in this figure are: ICI, ICI182,780; RAL, raloxifene; PROG, progesterone; EtOH, no added ligand.

DETAILED DESCRIPTION OF THE INVENTION

As used herein, "polypeptide monobody" is intended to mean a polypeptide which includes a β-strand domain lacking in disulfide bonds and containing a plurality of β-strands, two or more loop regions each connecting one β-strand to another β-strand, and optionally an N-terminal tail, a C-terminal tail, or both, wherein at least one of the two or more loop regions, the N-terminal tail, or the C-terminal tail is characterized by activity in binding a target protein or molecule. More specifically, such polypeptide monobodies of the present invention can include three or more loop regions or, even more specifically, four or more loop regions. The size of such polypeptide monobodies is preferably less than about 30 kDa, more preferably less than about 20 kDa.

Scaffolds for formation of a polypeptide monobody should be highly soluble and stable. It is small enough for structural analysis, yet large enough to accommodate multiple binding domains so as to achieve tight binding and/or high specificity for its target. One class of polypeptide monobodies of the present invention are characterized by specificity for binding to a nuclear receptor. One subclass of polypeptide monobodies of the present invention is characterized by their ability to bind to a nuclear receptor which has been previously bound by an agonist thereof. Another subclass of polypeptide monobodies of the present invention is characterized by their ability to bind to a nuclear receptor which has been previously bound by an antagonist thereof. To achieve the specificity in binding to a nuclear receptor (either with or without prior binding by an agonist or antagonist), the amino acid sequence of the polypeptide monobody has been modified relative to the scaffold used for its construction.

An exemplary scaffold for formation of a polypeptide monobody is the fibronectin type III domain (Fn3). Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily (Fn3 family or s-type Ig family) of the immunoglobulin superfamily. The Fn3 family includes cell adhesion molecules, cell surface hormone and cytokine receptors, chaperoning, and carbohydrate-binding domains (for reviews, see Bork & Doolittle, 1992; Jones, 1993; Bork et al., 1994; Campbell & Spitzfaden, 1994; Harpez & Chothia, 1994).

Crystallographic studies have revealed that the structure of the DNA binding domains of the transcription factor NF-kB is also closely related to the Fn3 fold (Ghosh et al., 1995; Müller et al., 1995). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a β-sandwich similar to that of antibody VH domain except that Fn3 has seven β-strands (FIGS. 1A-B) instead of nine. There are three loops on each end of Fn3; the positions of the BC, DE, and FG loops approximately correspond to those of CDR 1, 2 and 3 of the VH domain.

Fn3 is small (~94 residues, FIG. 2), monomeric, soluble, and stable. It is one of few members of IgSF that do not have disulfide bonds and, therefore, is stable under reducing conditions. Fn3 has been expressed in E. coli (Aukhil et al., 1993). In addition, 17 Fn3 domains are present just in human fibronectin, providing important information on conserved residues which are often important for the stability and folding (see Main et al., 1992; Dickinson et al., 1994). From sequence analysis, large variations are seen in the BC and FG loops, suggesting that the loops are not crucial to stability. NMR studies have revealed that the FG loop is highly flexible; the flexibility has been implicated for the specific binding of the 10th Fn3 to $\alpha_5\beta_1$ integrin through the Arg-Gly-Asp (RGD) motif. In the crystal structure of human growth hormone-receptor complex (de Vos et al., 1992), the second Fn3 domain of the receptor interacts with growth hormone via the FG and BC loops, suggesting it is feasible to build a binding site using the two loops.

Figure 1A:
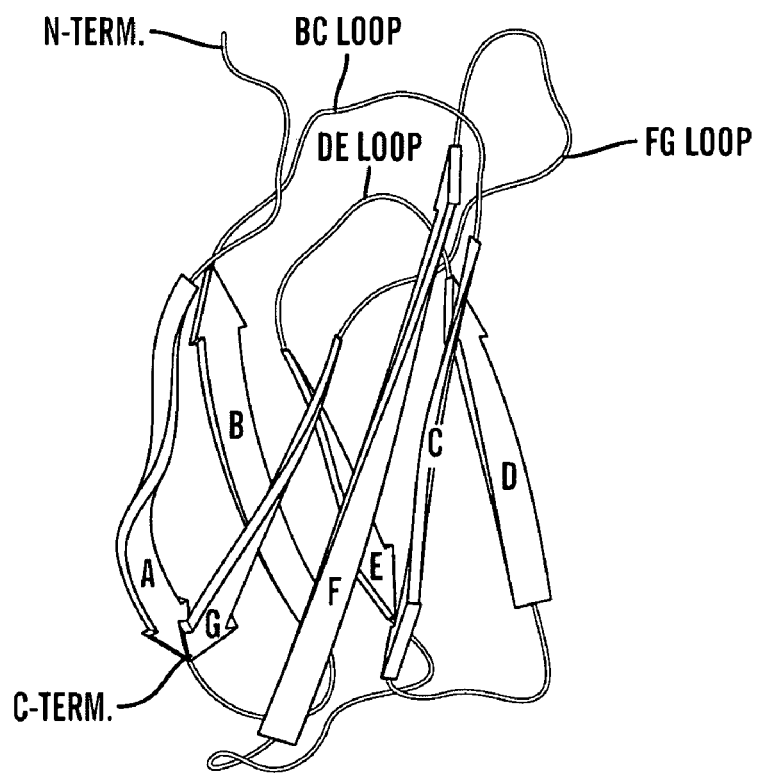
FIGS. 1A-B are schematic drawings of the structure of the tenth Fn3 domain of human fibronectin (FNfn10). β-Strands are labeled as A-G, and the loop regions that are used for target binding in monobodies are also labeled.
Figure 1B:
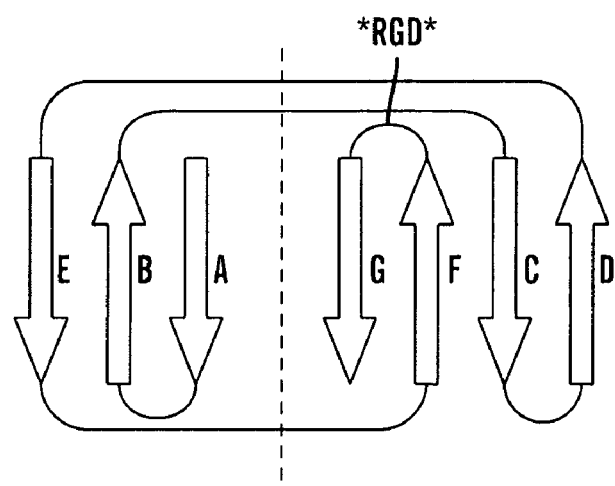

The tenth type III module of fibronectin has a fold similar to that of immunoglobulin domains, with seven β strands forming two antiparallel β sheets, which pack against each other (FIGS. 1A-B; Main et al., 1992). The structure of the type H module includes seven β strands, which form a sandwich of two antiparallel sheets, one containing three strands (ABE) and the other four strands (C'CFG) (Williams et al., 1988). The triple-stranded β sheet contains residues Glu-9-Thr-14 (A), Ser-17-Asp-23 (B), and Thr-56-Ser-60 (E). The majority of the conserved residues contribute to the hydrophobic core, with the invariant hydrophobic residues Trp-22 and Try-68 lying toward the N-terminal and C-terminal ends of the core, respectively. The β strands are much less flexible and appear to provide a rigid framework upon which functional, flexible loops can be built. The topology is similar to that of immunoglobulin C domains.

Preferred polypeptide monobodies of the present invention are fibronectin type III (Fn3)-derived polypeptide monobodies. Fn3 monobodies include at least two Fn3 β-strand domain sequences with a loop region sequence linked between adjacent β-strand domain sequences and optionally, an N-terminal tail of at least about 2 amino acids, a C-terminal tail of at least about 2 amino acids, or both. The at least one loop region sequence, the N-terminal tail, or the C-terminal tail, or combinations thereof include an amino acid sequence which has binding specificity for a nuclear receptor. To render a loop region sequence, N-terminal tail, or C-terminal tail capable of binding to a nuclear receptor, either the loop region sequence, the N-terminal tail, the C-terminal tail, or a combination thereof varies by deletion, insertion, or replacement of at least two amino acids from a corresponding loop region, N-terminal tail, or C-terminal tail in a wild-type or mutant Fn3 scaffold.

One preferred wild-type Fn3 scaffold is the tenth Fn3 domain of human fibronectin (FNfn10), which has an amino acid sequence according to SEQ ID No: 2 (FIG. 3A). One preferred mutant Fn3 scaffold is the tenth Fn3 domain of human fibronectin which has a modified Asp7, which is replaced by a non-negatively charged amino acid residue (i.e., Asn, Lys, etc.) as shown in FIG. 3B (SEQ ID No: 3). As reported in Koide et al. (2001), both of these mutations have the effect of promoting greater stability of the mutant FNfn10 at neutral pH as compared to the wild-type FNfn10.

Both the mutant and wild-type FNfn10 are characterized by the same structure, namely seven β-strand domain sequences (designated A through and six loop regions (AB loop, BC loop, CD loop, DE loop, EF loop, and FG loop) which connect the seven β-strand domain sequences. In SEQ ID Nos: 2 and 3, the AB loop corresponds to residues 15-16, the BC loop corresponds to residues 22-30, the CD loop corresponds to residues 39-45, the DE loop corresponds to residues 51-55, the EF loop corresponds to residues 60-66, and the FG loop corresponds to residues 76-87. As shown in FIGS. 1A-B, the BC loop, DE loop, and FG loop are all located at the same end of the polypeptide monobody.

The nuclear receptor which is bound by a polypeptide monobody of the present invention can be a steroid receptor, a thyroid receptor, a retinoid receptor, a vitamin D receptor, or orphan nuclear receptor. The polypeptide monobody of the present invention which binds to a nuclear receptor can be specific for the nuclear receptor which has been bound by a particular agonist or class of agonists, specific for the nuclear receptor which has been bound by a particular antagonist or class of antagonists, or specific for the nuclear receptor which been bound by neither an agonist nor an antagonist. Alternatively, the polypeptide monobody can bind to the nuclear receptor regardless of its conformation.

Exemplary steroid receptors include estrogen receptors (ER-α or ER-β), androgen receptors, progestin receptors, glucocorticoid receptors, and mineralocorticoid receptors. One class of preferred estrogen receptor-specific polypeptide monobodies exhibit estrogen receptor binding activity in the presence of an estrogen receptor agonist (e.g., estradiol, estriol, diethylstilbestrol, or genistein). Another class of preferred estrogen receptor-specific polypeptide monobodies exhibit estrogen receptor binding activity in the presence of an estrogen receptor antagonist (e.g., hydroxy tamoxifen, ICI182780, or raloxifene). Because of their tissue-specific functions, chemicals such as hydroxy tamoxifen and raloxifene are classified as selective estrogen receptor modulators (SERMs) (Jordan, 1998).

The polypeptide monobodies of the present invention can be prepared by recombinant techniques, thereby affording the deletion, insertion, or replacement of at least two amino acids from a corresponding loop region, N-terminal tail, or C-terminal tail in a wild-type or mutant Fn3 scaffold. Deletions can be a deletion of at least two amino acid residues up to substantially all but one amino acid residue appearing in a particular loop region or tail. Insertions can be an insertion of at least two amino acid residues up to about 25 amino acid residues, preferably at least two up to about 15 amino acid residues. Replacements can be replacements of at least two up to substantially all amino acid residues appearing in a particular loop region or tail. According to one embodiment of the polypeptide monobodies, such polypeptide monobodies possess an amino acid sequence which is at least 50% homologous to a β-strand domain of the FNfn10.

The deletions, insertions, and replacements (relative to wild-type or previously known mutant) on Fn3 scaffolds can be achieved using recombinant techniques beginning with a known nucleotide sequence. A synthetic gene for the tenth Fn3 of human fibronectin (FIG. 2) was designed which includes convenient restriction sites for ease of mutagenesis and uses specific codons for high-level protein expression (Gribskov et al., 1984). This gene is substantially identical to the gene disclosed in co-pending U.S. patent application Ser. No. 09/096,749 to Koide filed Jun. 12, 1998, which is hereby incorporated by reference in its entirety.

The gene was assembled as follows: first the gene sequence was divided into five parts with boundaries at designed restriction sites (FIG. 2); for each part, a pair of oligonucleotides that code opposite strands and have complementary overlaps of about 15 bases was synthesized; the two oligonucleotides were annealed and single strand regions were filled in using the Klenow fragment of DNA polyrnerase; the double-stranded oligonucleotide was cloned into the pET3a vector (Novagen) using restriction enzyme sites at the termini of the fragment and its sequence was confirmed by an Applied Biosystems DNA sequencer using the dideoxy termination protocol provided by the manufacturer; and these steps were repeated for each of the five parts to obtain the whole gene. Although this approach takes more time to assemble a gene than the one-step polymerase chain reaction (PCR) method (Sandhu et al., 1992), no mutations occurred in the gene. Mutations would likely have been introduced by the low fidelity replication by Taq polymerase and would have required time-consuming gene-editing. Recombinant DNA manipulations were performed according to Molecular Cloning (Sambrook et al., 1989), unless otherwise stated.

Mutations can be introduced to the Fn3 gene using either cassette mutagenesis, oligonucleotide site-directed mutagenesis techniques (Deng & Nickoloff, 1992), or Kunkel mutagenesis (Kunkel et al., 1987).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the monobody nucleotide sequence, sequencing can be performed to confirm that the designed mutations (and no other mutations) were introduced by mutagenesis reactions.

In contrast, Kunkel mutagenesis can be utilized to randomly produce a plurality of mutated monobody coding sequences which can be used to prepare a combinatorial library of polypeptide monobodies for screening. Basically, targeted loop regions (or C-terminal or N-terminal tail regions) can be randomized using the NNK codon (N denoting a mixture of A, T, G, C, and K denoting a mixture of G and T) (Kunkel et al., 1987).

Regardless of the approach used to prepare the nucleic acid molecules encoding the polypeptide monobody, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences.

U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant molecules can be introduced into cells via transformation, particularly transduction, conjugation, mobilization, or electroporation. The DNA sequences are cloned into the vector using standard cloning procedures in the art, as described by Sambrook et al. (1989).

A variety of host-vector systems may be utilized to express the polypeptide monobody or fusion protein which includes a polypeptide monobody. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; and mammalian cell systems infected with virus (e.g., vaccinia virus, adenovirus, etc.). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (MRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters may not be recognized in or may not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the MRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts & Lauer (1979).

Once the DNA molecule encoding the polypeptide monobody has been cloned into an expression system, it is ready to be incorporated into a host cell. Such incorporation can be carried out by the various forms of transformation noted above, depending upon the vector/host cell system. Suitable host cells include, but are not limited to, bacteria, yeast cells, mammalian cells, etc.

Polypeptide monobodies of the present invention are particularly well suited for expression as fusion proteins in combinatorial libraries to be screened, i.e., using a yeast or mammalian two-hybrid system. Thus, another aspect of the present invention relates to a combinatorial library which includes a plurality of fusion polypeptides. Each of the fusion polypeptides within the combinatorial library includes a transcriptional activation domain fused to a fibronectin type III (Fn3) polypeptide monobody as described above, with at least one loop region sequence, the N-terminal tail, or the C-terminal tail including a combinatorial amino acid sequence which varies by deletion, insertion, or replacement of at least two amino acids from a corresponding loop region, N-terminal tail, or C-terminal tail in a wild-type Fn3 domain of fibronectin.

The size of the combinatorial library will necessarily vary depending on the size of the combinatorial sequence introduced into the monobody coding sequence (i.e., the number of mutations introduced into a particular loop or tail coding sequence). For purposes of screening, however, the combinatorial library is preferably at least about $10^3$ in size, affording at least about $10^5$ transformed cells. Therefore, while some redundancy may exist for each individual combinatorial amino acid sequence, considering the total number of transformants, the combinatorial sequence in each individual transformant differs from substantially all other combinatorial sequences present in the combinatorial array of transformants.

The combinatorial sequence in each polypeptide monobody can be the result of deletions, insertions, or replacements of the type described above. In certain aspects of the present invention, the combinatorial amino acid sequence is at least about 5 amino acids in length, including one or more deletions, insertions, or replacements. In other aspects of the present invention, the combinatorial amino acid sequence is at least about 10 amino acids in length, including one or more deletions, insertions, or replacements.

Yeast and mammalian two-hybrid systems have been established as standard methods to identify and characterize protein interactions in the nucleus of yeast cells (Fields & Song, 1989; Uetz & Hughes, 2000). These approaches have previously been adapted for combinatorial library screening of specific peptide libraries (Colas & Brent, 1998; Mendelsohn & Brent, 1994).

One version of the yeast-two hybrid system has been described (Chien et al., 1991) and is commercially available from Clontech (Palo Alto, Calif.).

Figure 4A:
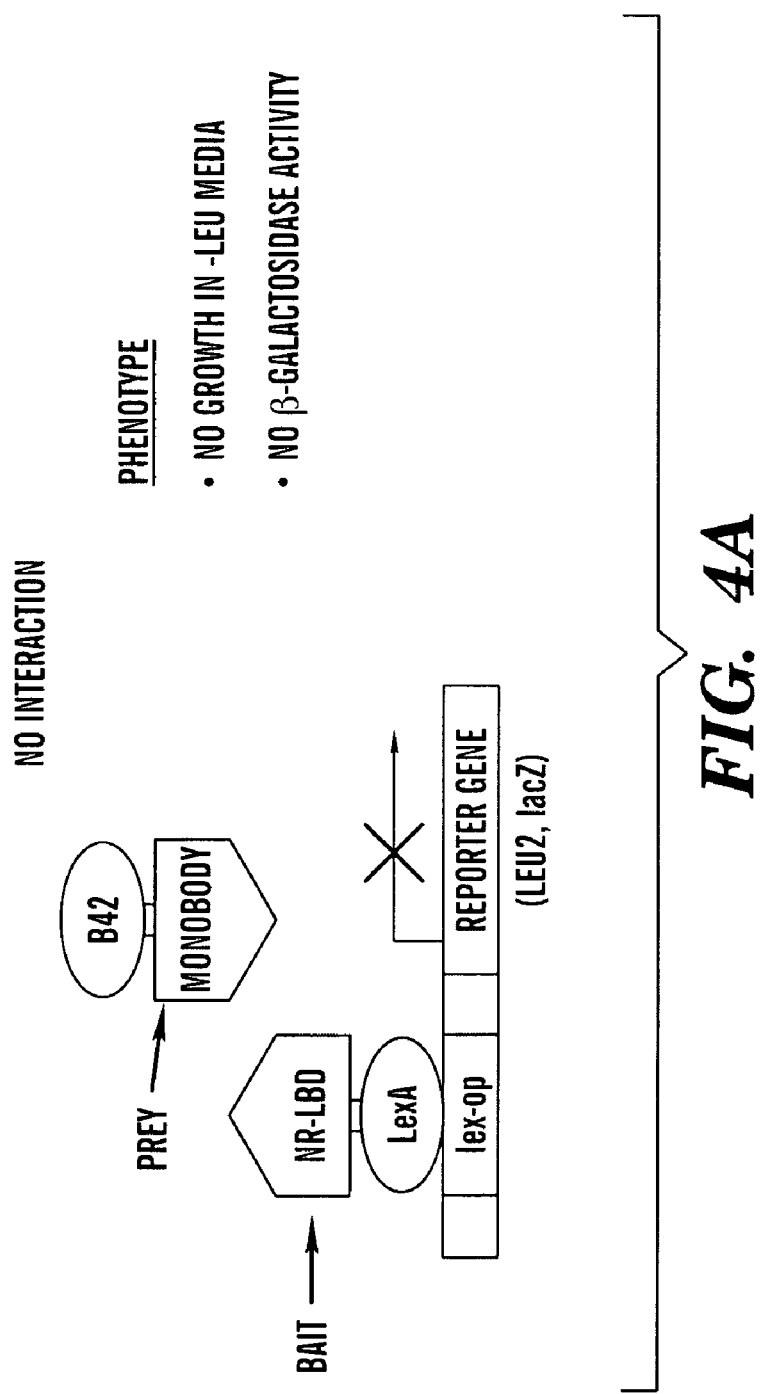
FIGS. 4A-B schematically illustrate a two-hybrid system. Two possibilities exist for interaction between the two fusion proteins: no interaction as shown in FIG. 4A or interaction as shown in FIG. 4B.
Figure 4B:
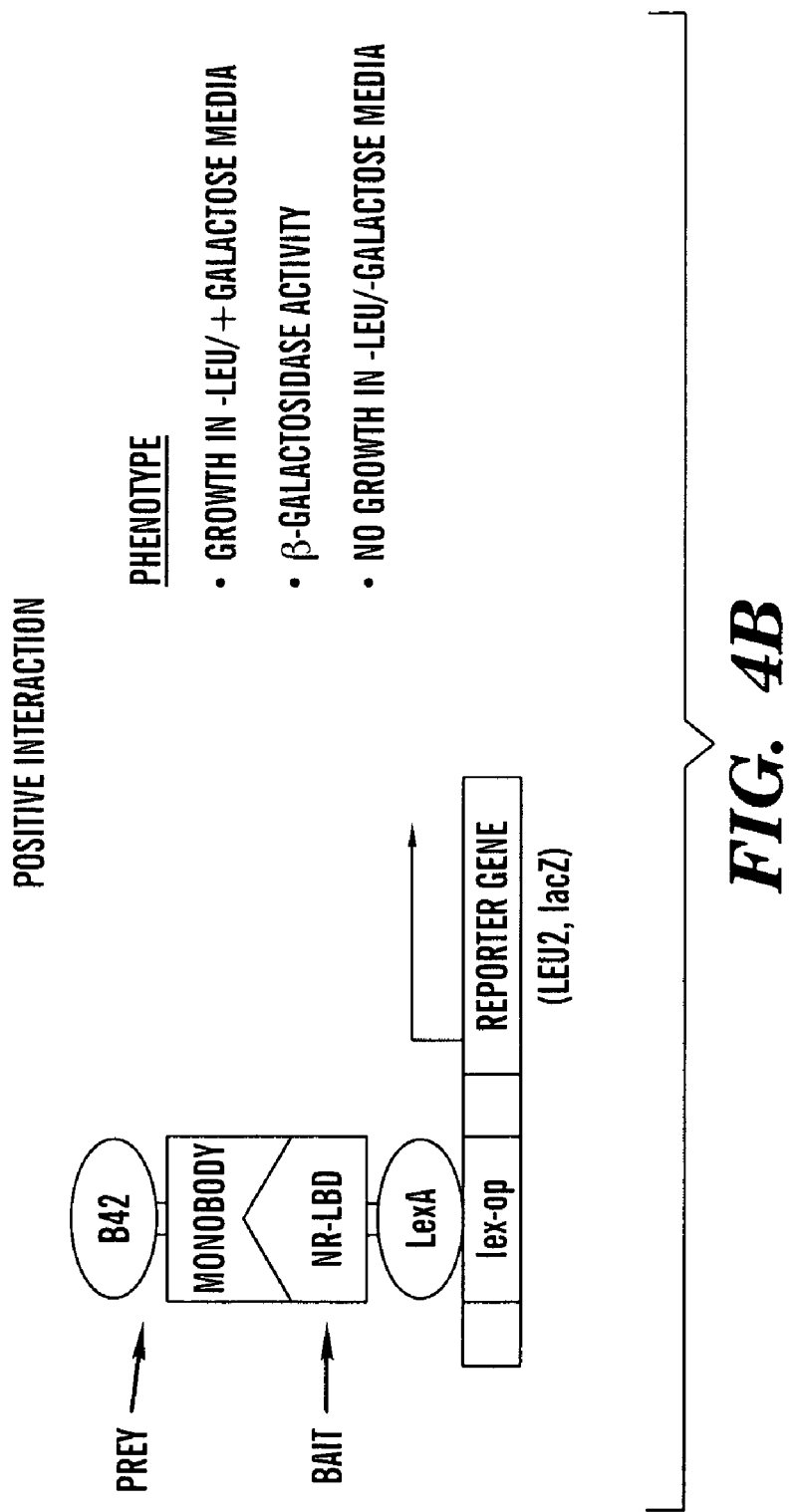

Briefly, utilizing such a system, plasmids are constructed that encode two fusion proteins, the interaction of which is shown schematically in FIGS. 4A-B. The first fusion protein (also known as "bait") contains the DNA-binding domain (e.g., LexA) fused to a known protein, in this case a nuclear receptor or fragment thereof which includes a functional ligand binding domain (NR-LBD). Any of the above-identified nuclear receptors (or fragments thereof which include a functional ligand binding domain) can be used as the bait protein or polypeptide. The second fusion protein (also known as "prey") includes an activation domain (e.g., B42) fused to an unknown protein, in this case a polypeptide monobody, that is encoded by a cDNA which has been recombined into a plasmid as part of a combinatorial cDNA library. Both plasmids include a promoter which is operable in yeast cells and which has been ligated upstream of the fusion protein coding regions. The plasmids are subsequently transformed into a strain of the yeast *Saccharomyces cerevisiae* that contains a reporter gene (e.g., LEU2, lacZ, GFP, etc.) whose expression is regulated by the transcription factor's binding site. Neither fusion protein alone can activate transcription of the reporter gene. The DNA-binding domain fusion protein cannot activate transcription, because it does not provide the activation domain function. The activation domain fusion protein cannot activate transcription, because it lacks the domain required for binding to its target site (e.g., it cannot localize to the transcription activator protein's binding site). If the monobody of the prey is not capable of binding to the nuclear receptor ligand binding domain of the bait (FIG. 4A), then no reporter gene product is observed. For example, there is no growth of the host yeast observed on (−)leu media and no β-galactosidase activity can be observed. In contrast, where interaction between the monobody of the prey and the nuclear receptor ligand binding domain of the bait occurs (FIG. 4B), a functional transcription factor is reconstituted, resulting in expression of the reporter gene which can be detected by an assay for the reporter gene product. For example, there is growth of the host yeast on (−)leu/(+)galactose media and β-galactosidase activity can be observed.

Thus, the two-hybrid system or related methodology can be used to screen activation domain libraries for polypeptide monobodies that interact with a known "bait" protein or polypeptide.

A number of suitable techniques can be utilizes to prepare DNA molecules encoding the "bait" and "prey" fusion proteins. Basically, coding sequences for the DNA binding domain and the nuclear receptor (or fragments thereof which include a functional receptor binding domain) or the activation domain and polypeptide monobody are ligated together to afford a single DNA molecule encoding a translationally fused "bait" or "prey", respectively. This can be carried out prior to insertion of the particular fusion protein coding sequence into an expression vector (containing the appropriate regulatory sequences) or simultaneously therewith.

Suitable yeast two-hybrid vectors can be derived from any number of known vectors. Exemplary bait plasmids include pEG202, pGilda, and pNLexA (Origine), and pHybLex/Zeo (Invitrogen). Exemplary prey plasmids include pYESTrp, pYESTrp2 (Invitrogen), and pJG4-5 (Origine). Suitable yeast-expressible promoters for driving expression of the fusion constructs, and the selection genes, if applicable, on the bait and prey library vectors, include but are not limited to, GAL1, ADH, and CUP.

As noted above, a cDNA library encoding polypeptide monobodies can be made using methods routinely practiced in the art. Accordingly, the library is generated by inserting those cDNA fragments (encoding the monobodies) into a vector such that they are translationally fused to the activation domain of B42 or Gal4. This library can be co-transformed along with the bait gene fusion plasmid into a yeast strain which contains, e.g., a lacZ gene, a nutrient marker gene, or a green fluorescent protein gene, whose expression is controlled by a promoter which contains a lexA or Gal4 activation sequence.

FIGS. 5-8 illustrate the coding sequence of different prey fusion protein constructs prepared in accordance with the present invention. The FNfn10-B42 fusion protein shown in FIG. 5 (SEQ ID No: 5) was prepared in the library designated pFNB42B5F7 (see Example 1 infra). This library was constructed by randomizing residues 26-30 in the BC loop and randomizing residues 78-84 in the FG loop (residue numbering according to Koide et al., 1998). The FNfn10-B42 fusion protein shown in FIG. 6 (SEQ ID No: 8) was prepared in the library designated pYT45AB7N (see Example 1 infra). This library was constructed by inserting seven diversified residues between Pro-15 and Thr-16 in the AB loop (residue numbering according to Koide et al., 1998). The FNfn10-B42 fusion protein shown in FIG. 7 (SEQ ID No: 11) was prepared in the library designated pYT45B3F7 (see Example 1 infra). This library was constructed by randomizing residues 26-30 in the BC loop and randomizing residues 78-84 in the FG loop (residue numbering according to Koide et al., 1998). The FNfn10-B42 fusion protein shown in FIG. 8 (SEQ ID No: 14) was prepared in the library designated pYT47F16 (see Example 1 infra). This library was constructed by randomizing residues 78-85 and inserting an additional eight randomized residues in the FG loop (residue numbering according to Koide et al., 1998).

Following co-transformation, the resulting transformants are screened for those that express the reporter gene. If a particular polypeptide monobody contains a polypeptide sequence which has activity binding to the nuclear receptor ligand binding domain, then the two fusion proteins will be brought together by the monobody binding to the nuclear receptor ligand binding domain. As a consequence, the B42 or Gal4 activation sequence is brought into sufficient proximity to the LexA or Gal4 binding domain, such that an active transcription factor is formed, thereby driving expression of the reporter gene (e.g., lacZ, nutrient marker, GFP, etc.). Yeast colonies which express lacZ can be detected by their blue color in the presence of X-gal, whereas yeast colonies expressing a nutrient marker can be identified by survival on nutrient selection media, and yeast colonies expressing a GFP can be detected by their fluorescence following exposure to an excitatory light source (e.g., of suitable wavelength). cDNA containing expressed reporter proteins can then be purified and used to produce and isolate the bait gene product interacting protein using techniques routinely practiced in the art.

Colonies expressing the reporter gene can be purified and the (library) plasmids responsible for reporter gene expression can be isolated. The inserts in the plasmids can also be sequenced to identify the proteins encoded by the cDNA or genomic DNA.

In addition, Finley et al. (1994) or Bendixen et al. (1994) have described two-hybrid systems including a step of mating yeast cell colonies by replicaplating diploids, that is to say by mating colonies of yeast cells.

U.S. Pat. No. 6,114,111 to Luo et al. describes one example of a mammalian two-hybrid system. Basically, this system includes the same components as described for the yeast two-hybrid system, except the various vectors used for transformation of mammalian host cells include viral origin of replication components that require the presence of a viral replication protein to effect replication. The reporter vector used in the mammalian two-hybrid system includes both a reporter gene and a viral replication protein. Upon binding of the two fusion proteins ("prey" and "bait"), the operator controlling expression of the reporter protein and viral replication protein is activated, affording increased transcription of the reporter gene and the viral replication protein gene. The viral replication protein can then bind to the viral origin of replication on the bait and test vectors to permit replication of the vector, ensuring survival of the cell due to the selection gene. The reporter gene then serves as the basis of a sorting or screening system to isolate cells which have a protein-protein interaction, and the test protein may be identified and characterized as desired.

Suitable mammalian two-hybrid vectors can be derived from any number of known vectors, including but not limited to, pCEP4 (Invitrogen), pCI-NEO (Promega), and pBI-EGFP (Clontech). Suitable promoters for driving expression of the fusion constructs, and the selection genes, if applicable, on the bait and test vectors, include but are not limited to, CMV promoters, SV40, SR-α (Takebe et al., 1988), respiratory synsitial viral promoters, thymine kinase promoter, β-globin promoter, etc.

Based on the in vivo selection of combinatorial libraries containing polypeptide monobodies, via yeast or mammalian two-hybrid protocols, a further aspect of the present invention relates to an in vivo composition which includes: a combinatorial library of the present invention, a reporter gene under control of a 5' regulatory region; and a chimeric gene which encodes a second fusion polypeptide comprising a target protein, or fragment thereof, fused to the C-terminus of a DNA-binding domain which binds to the 5' regulatory region of the reporter gene. Upon binding of the polypeptide monobody of the fusion polypeptide to the target protein, or fragment thereof, of the second fusion polypeptide, the transcriptional activation domain of the fusion polypeptide is brought into sufficient proximity to the DNA-binding domain of the second fusion polypeptide to induce expression of the reporter gene.

The two hybrid system is not limited to nuclear receptors. Virtually any target protein that does not self-activate the reporter gene can be used. The two hybrid system is not suitable for membrane-bound targets. For such targets, the split ubiquitin (Johnsson & Varshavsky, 1994) or dihydrofolate reductase reconstitution can be used (Pelletier et al., 1998).

A further aspect of the present invention relates to a method of identifying a polypeptide monobody having target protein binding activity. This method is carried out by providing a host cell which includes (i) a reporter gene under control of a 5' regulatory region operable in the host cell, (ii) a first chimeric gene which encodes a first fusion polypeptide including a target protein, or fragment thereof, fused to a C-terminus of a DNA-binding domain which binds to the 5' regulatory region of the reporter gene, and (iii) a second chimeric gene which encodes a second fusion polypeptide comprising an polypeptide monobody fused to a transcriptional activation domain; and detecting expression of the reporter gene. Reporter gene expression indicates binding of the polypeptide monobody of the second fusion polypeptide to the target protein (such that the transcriptional activation domain of the second fusion polypeptide is in sufficient proximity to the DNA-binding domain of the first fusion polypeptide to allow expression of the reporter gene).

The target protein can be any protein or polypeptide. A preferred target protein is a nuclear receptor of the type described above.

The polypeptide monobody can be any polypeptide monobody as described above, but preferably one which is derived from the tenth Fn3 domain of human fibronectin, as described above.

Providing the host cell which expresses the reporter gene and the first and second chimeric genes can be achieved through recombinant techniques known in the art or otherwise described above. Basically, this includes transforming host cells and/or mating recombinant host cells to achieve the recited host cell. For example, a cell expressing the reporter gene can be transformed upon introduction of first and second vectors (e.g., plasmids) which contain, respectively, the first and second chimeric genes. The host cell can be either a yeast cell or a mammalian cell.

The method of carrying out detection of the reporter protein depends on the type of reporter protein which is expressed. For example, with the lacZ reporter, detection can be carried out by exposing host cells to X-gal and identifying host cell colonies exhibiting β-galactosidase activity (presence of blue color); with a nutrient marker, detection can be carried out by exposing host cells to a nutrient-deficient media and identifying yeast colonies that grow on the nutrient-deficient media; or with GFP reporters, detection can be carried out by exposing the host cells to an excitatory light source (of appropriate wavelength) and identifying host cells that emit light at a particular wavelength (i.e., which is particular for a given GFP).

In addition, this aspect of the present invention also contemplates recovering the second chimeric gene from host cells exhibiting reporter protein expression (identified as described above), modifying the amino acid sequence of the encoded polypeptide monobody, and then repeating the steps of providing and detecting (as described above) under more stringent conditions using a modified second chimeric gene (which encodes the modified polypeptide monobody). The purpose of this procedure is to identify polypeptide monobodies which have greater affinity (lower dissociation constant) for the target protein. In modifying the second chimeric gene, mutations can be introduced into the polypeptide monobody coding sequence to modify any of the loop regions, either in addition to a loop region which was originally modified or into a different loop region. For polypeptide monobodies derived from the tenth Fn3 domain of human fibronectin, mutations can be introduced into one or more of the plurality of loop sequences, the N-terminal tail, or the C-terminal tail.

According to another aspect of the present invention, the two-hybrid system can be used to screen candidate drugs for agonist or antagonist activity against nuclear receptors. This method is carried out by first providing a host cell including (i) a reporter gene under control of a 5' regulatory region, (ii) a first chimeric gene which encodes a first fusion polypeptide including a nuclear receptor, or fragment thereof including a ligand-binding domain, fused to a C-terminus of a DNA-binding domain which binds to the 5' regulatory region of the reporter gene, and (iii) a second chimeric gene which encodes a second fusion polypeptide including a polypeptide sequence fused to a transcriptional activation domain. The polypeptide sequence can bind to the nuclear receptor, or fragment thereof, either in the absence of both an agonist and an antagonist of the nuclear receptor, in the presence of an agonist of the nuclear receptor, in the presence of an antagonist of the nuclear receptor, or in the presence of both an agonist and an antagonist of the nuclear receptor. The host cell is grown in a growth medium which includes the candidate drug and expression of the reporter gene is detected. Reporter gene expression indicates binding of the polypeptide sequence of the second fusion polypeptide to the nuclear receptor, or fragment thereof, such that the transcriptional activation domain of the second fusion polypeptide is in sufficient proximity to the DNA-binding domain of the first fusion polypeptide to allow expression of the reporter gene. Depending upon the nature of the polypeptide sequence and its binding activity in the presence or absence of agonists or antagonists of the nuclear receptor, modulation of reporter gene expression can indicate whether the candidate drug is an agonist or an antagonist of the nuclear receptor, or whether the candidate drug has mixed activity.

For example, polypeptide sequences which bind the nuclear receptor only in the presence of nuclear receptor agonists will be capable of indicating that the candidate drug has nuclear receptor agonist activity, whereas polypeptide sequences which bind the nuclear receptor only in the presence of nuclear receptor antagonists will be capable of indicating that the candidate drug has nuclear receptor antagonist activity. Similarly, polypeptide sequences which bind the nuclear receptor only in the presence of both nuclear receptor agonists and nuclear receptor antagonists will be capable of indicating that the candidate drug has mixed activity. Finally, polypeptide sequences which bind the nuclear receptor only in the absence of both nuclear receptor agonists and nuclear receptor antagonists will be capable of confirming that a candidate drug has no nuclear receptor binding activity.

The polypeptide sequence which is used to perform the candidate drug screening can be any polypeptide sequence which has nuclear receptor binding activity under the various conditions. Preferably, candidate drugs are screened in up to four different types of host cells, each of the four types expressing a different second fusion polypeptide which includes a polypeptide sequence specific for binding under the four recited conditions (i.e., presence of nuclear receptor agonist, presence of nuclear receptor antagonist, absence of both nuclear receptor agonist and antagonist, and presence of both nuclear receptor agonist and antagonist). Thus, candidate drugs can be screened in each of the environments which can define the nature of its nuclear receptor binding activity.

According to another embodiment for screening candidate drugs for nuclear receptor binding, the polypeptide sequence of the second fusion polypeptide is a polypeptide monobody. The polypeptide monobody can be any monobody as described herein, but preferably a polypeptide monobody derived from the tenth Fn3 domain of human fibronectin.

As used above, candidate drugs can also refer to potentially toxic agents. Regardless of whether the candidate drug is a potentially therapeutic agent or one which can cause or contribute to development of a disease state (i.e., an endocrine disrupter), the same assay can be performed to determine whether the drug or agent being screened binds to a particular nuclear receptor and causes the nuclear receptor to adopt a particular conformation.

As described above, the transformed host cells expressing a two-hybrid system can be used as sensors for detecting conformationally-dependent nuclear receptor binding activity of candidate drugs. Therefore, a related aspect of the present invention relates to a kit for practicing this method of the invention. The kit includes: a culture system which includes a culture medium on which has been (or can be) placed at least one transformed host cell, each of the at least one transformed host cell including (i) a reporter gene under control of a 5' regulatory region, (ii) a first chimeric gene which encodes a first fusion polypeptide comprising a nuclear receptor, or fragment thereof including a ligand-binding domain, fused to a C-terminus of a DNA-binding domain which binds to the 5' regulatory region of the reporter gene, and (iii) a second chimeric gene which encodes a second fusion polypeptide including a polypeptide sequence fused to a transcriptional activation domain. The polypeptide sequence can bind to the nuclear receptor, or fragment thereof, either in the absence of both an agonist and an antagonist of the nuclear receptor, in the presence of an agonist of the nuclear receptor, in the presence of an antagonist of the nuclear receptor, or in the presence of both an agonist and an antagonist of the nuclear receptor.

Another kit of the present invention enables a user the flexibility to mutate the polypeptide monobody as desired prior to transformation of host cells in a two-hybrid system. This kit of the present invention includes: a plurality of host cells, each including a reporter gene under control of a 5' regulatory region and a heterologous DNA molecule encoding a first fusion polypeptide including a nuclear receptor, or fragment thereof which includes a ligand-binding domain, fused to a C-terminus of a DNA-binding domain which binds to the 5' regulatory region of the reporter gene; and a vector including a DNA molecule encoding a second fusion polypeptide including a transcriptional activation domain fused to a polypeptide monobody. The vector including the DNA molecule encoding the second fusion polypeptide can be present in a host cell. Upon mutation of the DNA molecule to encode a mutant polypeptide antibody and introduction of the vector into at least a portion of the plurality of host cells, expression of the reporter gene is induced upon binding of the polypeptide monobody of the second fusion polypeptide to the nuclear receptor, or fragment thereof, of the first fusion polypeptide such that the transcriptional activation domain of the second fusion polypeptide is in sufficient proximity to the DNA-binding domain of the first fusion polypeptide.

Having identified (i.e., using a two-hybrid system) individual polypeptide monobodies which have activity in binding to a target protein, the identified monobodies can also be used to validate the target. Thus, another aspect of the present invention relates to a method of target validation. Basically, this aspect of the present invention is used to demonstrate that inhibiting target protein function produces the desired effect. The desired effect can be therapeutic, overcoming a disease state, or prophylactic.

In addition to nuclear receptors of the type described above, a number of targets can be identified and validated, including other signal transducing proteins such as G proteins, cell surface receptors (e.g., interleukin 2 receptors, growth hormone receptors, BI receptors, integrins, G protein-coupled receptors, etc.), and plant signaling proteins (e.g., CLV1/CLV2 receptor kinase complex); cell cycle regulatory proteins such as protein kinases (e.g., human CDK2) and protein phosphatase (e.g., human CDC25); infectious agent proteins such as virus proteins (e.g., HIV TAT, HIV reverse transcriptase, Vpr, Vpu, Nef, etc.), bacterial proteins (e.g., dihydropholate reductase, thymidine synthase, etc.), and fungal proteins (e.g., CPG-1); apoptosis-related proteins (e.g., B1c-2, IGF-2, p53); and transmembrane proteins (e.g., MDR-1, MRP, etc.).

Basically, the target-binding activity of a particular polypeptide monobody can be determined by performing a two-hybrid system screening for binding activity. Once polypeptide monobodies having the requisite binding activity have been identified, target protein validation can be conducted.

According to one embodiment, the method of validating target protein activity can be carried out by exposing a target protein to a polypeptide monobody which binds to the target protein and then determining whether binding of the target protein by the polypeptide monobody modifies target protein activity.

The exposing is preferably carried out in vivo using a host cell (e.g., a bacteria, mammalian cell, or yeast cell). The exposure can be carried out under a number of conditions depending upon the type of target protein which is being evaluated with a particular polypeptide monobody.

According to one approach, exposing can be carried out according to a two-hybrid assay with competition. The exposing is performed by co-expressing in a single cell including a reporter gene under control of a 5' regulatory region: (i) a first fusion polypeptide including a transcriptional activation domain fused to a target protein co-activator which binds the target protein, (ii) a second fusion polypeptide including a target protein fused to a C-terminus of a DNA-binding domain which binds to the 5' regulatory region of the reporter gene, and (iii) a polypeptide monobody which binds the target protein. In this embodiment, absence of reporter gene expression indicates that the polypeptide monobody effectively inhibits the activity of the target protein and the target protein co-activator.

Several other approaches can be utilized depending upon the nature of the target protein activity and whether a target protein has a known activity.

When activity of the target protein is unknown, mRNA or protein expression levels before and after exposure to the polypeptide monobody can be detected and then compared to identify proteins which are downstream of a metabolic pathway in which the target protein is involved. Modified expression levels indicate modified target protein activity.

When a target protein is known to be required for cell growth or survival, determining whether target protein activity has been modified can be achieved by measuring cell growth or survival after exposure to the polypeptide monobody, wherein reduced cell growth or survival indicates inhibition of target protein activity.

When a target protein is a pathogen protein involved in host-pathogen interaction, the exposing is carried out in a host cell that includes the polypeptide monobody. The host cell is preferably one which is normally susceptible to pathogen infiltration and the host cell is exposed to the pathogen (e.g., virus, bacteria, fungus, etc.) under conditions which would normally be sufficient to allow for pathogen infiltration. To determine whether the polypeptide monobody can modify target protein activity, the extent of pathogen-induced disease progression is measured in the host cell.

Yet another aspect of the present invention relates to measuring the binding affinity of a polypeptide monobody for a target protein. This aspect of the present invention is carried out by exposing a target protein to an interaction partner which binds the target protein and a polypeptide monobody which binds the target protein and measuring the degree to which the polypeptide monobody competes with the interaction partner.

According to one approach, this is a competitive assay which can be carried out in vitro. Typically, the target protein is bound to a substrate and the polypeptide monobody includes a label (e.g., alkaline phosphatase tag or a $His_{(6)}$ tag), which allows the degree of monobody binding both in the absence of the interaction partner and in the presence of the interaction partner. By measuring the difference between the degree of binding under such conditions, it is possible to estimate the binding affinity for the polypeptide monobody if the binding affinity of the interaction partner is known.

According to another approach, this assay which can be carried out in vivo according to a two-hybrid assay with competition. The exposing is performed by co-expressing in a cell including a reporter gene under control of a 5' regulatory region: (i) a first fusion polypeptide including a transcriptional activation domain fused to a target protein co-activator which binds the target protein, (ii) a second fusion polypeptide including the target protein fused to a C-terminus of a DNA-binding domain which binds to the 5' regulatory region of the reporter gene, and (iii) a polypeptide monobody which binds the target protein. Where no substantial reduction in reporter gene is detected (relative to a control when the polypeptide monobody is not present), then the binding affinity of the polypeptide monobody is less than that of the co-activator. In contrast, where a substantial reduction in reporter gene expression is detected relative to the control, then the binding affinity of the polypeptide monobody is similar to or greater than that of the co-activator, indicating that the polypeptide monobody effectively competes with the interaction partner for binding to the target protein.

Having validated a polypeptide monobody's activity in binding a target protein and modifying its activity, the tested polypeptide monobodies can therefore be used to modulate target protein activity. Thus, a further aspect of the present invention relates to a method of modulating target protein activity which includes: exposing a target protein to a polypeptide monobody which binds the target protein under conditions effective to modify target protein activity. Modification of target protein activity is particularly suited for provided therapeutic or prophylactic benefit and, therefore, exposure of the polypeptide monobody to the target protein is preferably carried out in vivo (e.g., in a yeast cell, bacterial cell, or mammalian cell).

Having identified and validated that certain polypeptide monobodies bind to a target protein (whether it assumes a particular conformation or not), the polypeptide monobodies can also be used for therapeutic administration to modify the activity of the target protein in vivo.

For purposes of therapeutic usage, it is preferred that the polypeptide monobodies be prepared in substantially pure form. This can be performed according to standard procedures. Typically, this involves recombinant expression of the desired polypeptide monobody by a host cell, propagation of the host cells, lysing the host cells, and recovery of supernatant by centrifugation to remove host cell debris. The supernatant can be subjected to sequential ammonium sulfate precipitation. The fraction containing the polypeptide monobody of the present invention is subjected to gel filtration in an appropriately sized dextran or polyacrylamide column to separate the polypeptide monobodies. If necessary, the protein fraction may be further purified by HPLC. The isolation and purification of polypeptide monobodies, in particular, has previously been reported by Koide et al. (1998).

According to one embodiment, polypeptide monobodies which bind to the estrogen receptor and function as antagonist can be used in treating or preventing breast cancer. Exemplary antagonist monobodies are those which inhibit SRC-1 (infra). Current breast cancer treatments include the use of antiestrogens such as tamoxifen and raloxifene as chemotherapeutics. Thus, polypeptide monobodies with antagonist behavior would also be expected to be useful as a cancer therapeutic.

A number of known delivery techniques can be utilized for the delivery, into cells, of either the polypeptide monobodies themselves or nucleic acid molecules which encode them.

Regardless of the particular method of the present invention which is practiced, when it is desirable to contact a cell (i.e., to be treated) with a polypeptide monobody or its encoding nucleic acid, it is preferred the contacting be carried out by delivery of the polypeptide monobody or its encoding nucleic acid into the cell.

One approach for delivering polypeptide monobody or its encoding RNA into cells involves the use of liposomes. Basically, this involves providing the polypeptide monobody or its encoding RNA to be delivered, and then contacting the target cell with the liposome under conditions effective for delivery of the polypeptide monobody or RNA into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (Wang & Huang, 1987). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al. (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., as well as any other approach demonstrated in the art.

An alternative approach for delivery of polypeptide monobodies involves the conjugation of the desired polypeptide monobody to a polymer that is stabilized to avoid enzymatic degradation of the conjugated monobody. Conjugated proteins or polypeptides of this type are described in U.S. Pat. No. 5,681,811 to Ekwuribe.

Yet another approach for delivery of polypeptide monobodies involves preparation of chimeric proteins according to U.S. Pat. No. 5,817,789 to Heartlein et al. The chimeric protein can include a ligand domain and, e.g., a polypeptide monobody which has activity to bind a cellular target (e.g., a nuclear receptor or other cellular protein). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein. An exemplary approach is the HIV Tat protein.

When it is desirable to achieve heterologous expression of a desirable polypeptide monobody in a target cell, DNA molecules encoding the polypeptide monobody can be delivered into the cell. Basically, this includes providing a nucleic acid molecule encoding the polypeptide monobody and then introducing the nucleic acid molecule into the cell under conditions effective to express the polypeptide monobody in the cell. Preferably, this is achieved by inserting the nucleic acid molecule into an expression vector before it is introduced into the cell.

When transforming mammalian cells for heterologous expression of a polypeptide monobody, an adenovirus vector can be employed. Adenovirus gene delivery vehicles can be readily prepared and utilized given the disclosure provided in Berkner (1988) and Rosenfeld et al. (1991). Adeno-associated viral gene delivery vehicles can be constructed and used to deliver a gene to cells. The use of adeno-associated viral gene delivery vehicles in vivo is described in Flotte et al. (1993) and Kaplitt et al. (1994). Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel.

Retroviral vectors which have been modified to form infective transformation systems can also be used to deliver nucleic acid encoding a desired polypeptide monobody into a target cell. One such type of retroviral vector is disclosed in U.S. Pat. No. 5,849,586 to Kriegler et al.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired polypeptide monobody, allowing the polypeptide monobody to modify the activity of its target protein.

According to one embodiment, the polypeptide monobody (or fusion protein which includes the polypeptide monobody) can also include a localization signal for retention of the monobody in the endoplasmic reticulum. An exemplary localization signal is a KDEL amino acid sequence (SEQ ID No: 21) secured via peptide bond to the C-terminal end of the polypeptide monobody.

Whether the polypeptide monobodies or nucleic acids are administered alone or in combination with pharmaceutically or physiologically acceptable carriers, excipients, or stabilizers, or in solid or liquid form such as, tablets, capsules, powders, solutions, suspensions, or emulsions, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. For most therapeutic purposes, the polypeptide monobodies or nucleic acids can be administered intravenously.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the polypeptide monobodies or nucleic acids in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Dosages to be administered can be determined according to known procedures, including those which balance both drug efficacy and degree of side effects.

EXAMPLES

The following examples are provided to illustrate embodiments of the present invention but are by no means intended to limit its scope.

Materials and Methods

17 β-estradiol (E2) and 4-hydroxy tamoxifen (OHT) were purchased from Sigma; diethylstilbestrol, estriol, progesterone were obtained from Steraloids;

ICI182,780 was purchased from Tocris, and raloxifene is a product of Eli Lilly. An anti-ERα (F domain) antibody, HC-20, was purchased from Santa Cruz Biotech, and anti-LexA antibody was kindly provided by Dr. E. Golemis (Fox Chase Cancer Center). Secondary antibodies were purchased from Pierce. An estrogen receptor α (ERα) cDNA clone was kindly provided by the late Dr. A. Notides (University of Rochester Medical Center). The cDNA clone for steroid receptor coactivator-1 (SRC-1) was a generous gift from Dr. B. W. O'Malley (Baylor College of Medicine) (Onate et al., 1995).

Yeast strains EGY48, MATα his3 trp1 ura3 leu2::6Lex-Aop-LEU2, and RFY206, MATα his3Δ200 leu2-3 lys2Δ201 trp1Δ::hisG ura3-52, have been described (Gyuris et al., 1993; Finley & Brent, 1994) and were purchased from Origene. Yeast was grown in YPD media or YC dropout media following instructions from Origene and Invitrogen.

Example 1

Construction of Yeast Two-Hybrid Vectors and Monobody Library

Figure 9:
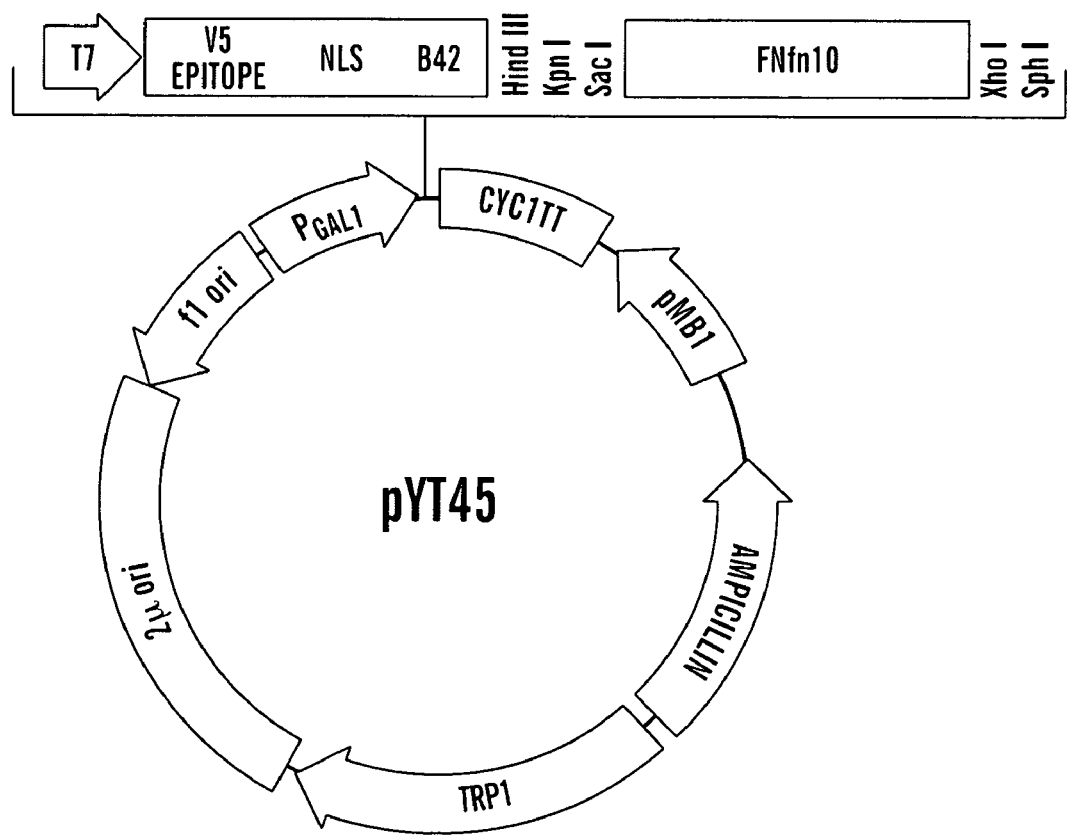
FIG. 9 is a map of plasmid of pYT45, which is derived from plasmid pYESTrp2 (Invitrogen, Calif.) by the introduction of FNfn10 (Koide et al., 1998) so that FNfn10 was fused C-terminal to the B42 activation domain. pYESTrp2 and, thus, pYT45 includes a T7 promoter sequence upstream of regions coding for (from 5' to 3') a V5 epitope, a nuclear localization signal, the B42-FNfn10 fusion.

The method of Brent and others were followed in the construction of vectors (Colas & Brent, 1998; Mendelsohn & Brent, 1994; Golemis & Serebriiskii, 1997). The synthetic gene for FNfn10 (Koide et al., 1998) was subcloned in the plasmid pYESTrp2 (Invitrogen, Calif.) so that FNfn10 was fused C-terminal to the B42 activation domain (pYT45). A map of pYT45 is shown at FIG. 9. This plasmid includes a T7 promoter sequence upstream of regions coding for (from 5' to 3') a V5 epitope, a nuclear localization signal, a B42 activation domain, and a combinatorial polypeptide monobody derived from FNfn10. The nucleotide (SEQ ID No: 16) and amino acid sequences (SEQ ID No: 17) for the B42-FNfn10 fusion are shown in FIG. 10.

Figure 11:
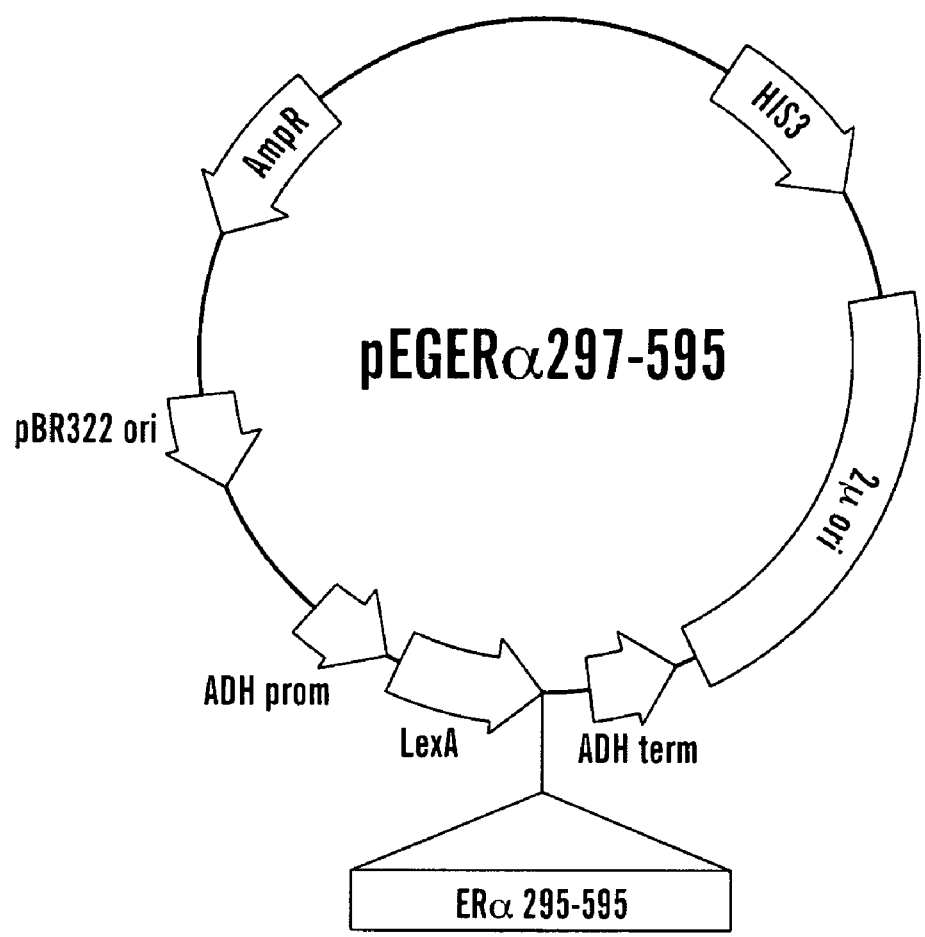
FIG. 11 is a map of plasmid pEGERα295-595, which is derived from pEG202 (Origine). pEGERα295-595 includes the E and F domains (residues 295-595) of estrogen receptor α. Insertion of the coding sequence for the EF domains affords a lexA-ERαEF fusion construct.

The following plasmids encoding LexA-fusion proteins were constructed by subcloning an appropriate PCR fragment in the plasmid pEG202 (Origene): pEGERα297-595, ERα-EF (residues 297-595, the E and F domains of Estrogen Receptor α) (FIG. 11); pEGERα297-554, ERα-E (residues 297-554, the E domain of Estrogen Receptor α); pEGSRC1, residues 570-780 of SRC-1 (Onate et al., 1995). FIGS. 12A-B illustrate the nucleotide (SEQ ID No: 18) and amino acid (SEQ ID No: 19) of the LexA-ERα fusion protein in plasmid pEGERα295-595. The F domain is about 45-residues long, and it is believed to be highly flexible. Potential roles of this domain in the ligand-dependent transcription activation have been reported (Nichols et al., 1997; Montano et al., 1995). None of the published crystal structures of ER-ligand binding domain includes the F domain. The F domain was included in one of the constructs so that the bait protein is closer to the full-length ER, rather than just the ligand binding domain.

A number of monobody libraries were constructed by diversifying residues in several loop regions. Libraries pFNB42B5F7 (FIG. 5) and pYT45B3F7 (FIG. 7) were prepared by diversifying residues 26-30 in the BC loop and randomizing residues 78-84 in the FG loop (residue numbering according to Koide et al., 1998). Library pYT45AB7N was prepared by inserting seven diversified residues between Pro-15 and Thr-16 in the AB loop (residue numbering according to Koide et al., 1998). Library pYT47F16 was prepared by randomizing residues 78-85 and inserting an additional eight randomized residues in the FG loop (residue numbering according to Koide et al., 1998). In each instance, the above-noted residues were randomized using the NNK codon (N denotes a mixture of A, T, G, C; K denotes a mixture of G and T) or NNS codon (S denotes a mixture of G and C) by Kunkel mutagenesis (Kunkel et al., 1987). The yeast strain EGY48 was transformed with this plasmid to produce a library containing approximately 2×10$^6$ independent clones. To facilitate fusion protein construction, NcoI and BamHI sites were introduced at the 5' and 3' ends of monobody genes, respectively, using PCR.

A yeast expression vector for a glutathione-S-transferase (GST)-monobody fusion protein was constructed as follows. The XbaI-KpnI fragment of the modified pYEX4T-1 vector that encodes Pcup promotor and GST gene, kindly provided by Dr. E. Phizicky (Martzen et al., 1999), was cloned between the XbaI and KpnI sites of YEplac181 (Gietz & Sugino, 1988) to make pGSTleu. Then the gene for a monobody (i.e., from the constructed library) was cloned between the NcoI and BamHI sites of pGSTleu.

Example 2

Screening of Monobody Library for Estrogen Receptor-α EF Domain Specificity in the Presence of a Ligand The yeast strain RFY206 harboring pEGERα297-595 and a LacZ reporter plasmid, pSH18-34 (Origene), was mated with EGY48 containing the monobody library (Finley & Brent, 1994). Diploid cells that contain an ERα-binding monobody were selected using the LEU$^+$ phenotype on minimal dropout media (Gal Raf-leu-his-ura-trp). (Although ERα itself has a weak transcriptional activation function in yeast (Chen et al., 1997), these constructs did not activate the LEU2 reporter gene to an extent that confers LEU$^+$ phenotype in the yeast EGY48.)

A series of library screening was performed in the presence of different ERα ligands (E2, estriol, and OHT). The ligand concentration used was 1 μM. Colonies grown after three days of incubation were further tested for galactose-dependence of the LEU+ phenotype and β-galactosidase activity. The plasmids coding for a monobody were recovered from yeast clones following instructions supplied by Origene, and the amino acid sequences of monobodies were deduced by DNA sequencing.

Quantitative assays were performed as follows. The yeast strain RFY206 was (1) first transformed with pEGERα297-595 (or pEGERα297-554) and pSH18-34 and (2) subsequently with a derivative of the pYT45 plasmid encoding a particular monobody. Yeast cells were grown overnight at 30° C. in YC Glc-his-ura-trp media. The culture was then spun down, the media were discarded, and the cells were resuspended in YC Gal Raf-his-ura-trp media containing a ligand at a final cell density of 0.2 $OD_{660\,nm}$ in a total volume of 175 μl in the wells of a deep 96-well plate. Ligands used were E2, ICI182,780, OHT, raloxifene, progesterone, estriol, diethylstilbestrol, and genistein. The ligand concentration was 1 μM except for genistein (10 μM). After incubating for six hours at 30° C. with shaking, 175 μl of β--galactosidase assay buffer (60 mM $Na_2HPO_4$, 40 mM $NaH_2PO_4$, 10 mM KCl, 1 mM $MgSO_4$, 0.27% β-mercaptoethanol, 0.004% SDS, 4 mg/ml 2-nitrophenyl-β-D-galactosidase, 50% Y-PER (Pierce)) was added to the culture, incubated at 30° C., then the reaction was stopped by adding 150 μl of 1M $Na_2CO_3$. After centrifugation, $OD_{420}$ was measured and the β-galactosidase activity was calculated.

Western blotting was used to examine the amounts of the LexA fusion and monobody proteins in yeast cells used for β-galactosidase assays. Yeast cells were grown in the same manner as for the β-galactosidase assays described above. Yeast cells were spun down to discard media and weighed. The cells were suspended in 5 μl Y-PER (Pierce) per mg cell, then 1 mM PMSF and 540 μg/ml Leupeptine were added, and the samples were incubated at room temperature for 20 min with gentle agitation. The suspension was spun down, supernatant was recovered, and the pellet was resuspended in 5 mM Tris-Cl (pH 8.0). The supernatant and suspension were examined by Western blotting.

Multiple positive clones were obtained from each screening and their amino acid sequences were determined, as shown in Table 1-4 below.

Figure 13D:
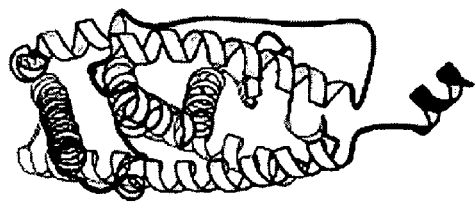
FIGS. 13A-D illustrate the structure of estrogen receptor α.
Figure 13A:
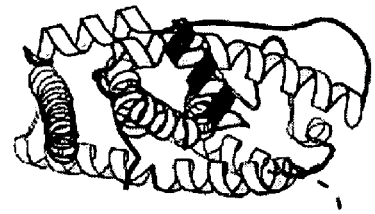
Figure 13C:
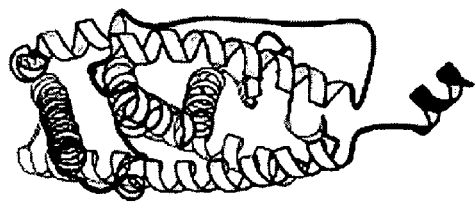

Monobodies that have been selected in the presence of an agonist (E2 and E3) contain motifs similar to LXXLL (SEQ ID No: 20, where X is any amino acid) that is the consensus of the NR boxes of coactivators (Heery et al., 1997). Interestingly, a significant number of LXXML (SEQ ID No: 32, where X is any amino acid) sequences were present among these clones. Because of the degeneracy of the codons, Leu is expected to appear three times as often as Met at a given position that was diversified in the library, suggesting that Met in the LXXML (SEQ ID No: 32) sequence is preferred over Leu. In addition, many of the clones contain an amino acid with a carboxyl or amino side chain at the third position of the LXXLL (SEQ ID No: 20)-like motifs. These motifs bear striking resemblance to the LLEML (SEQ ID No: 33) sequence within helix12 of ERα and β. In the ERα/OHT crystal structure, the LLEML (SEQ ID No: 33) segment of helix12 occupies the coactivator binding site (FIG. 13C) (Shiau et al., 1998). The sequence similarity of the isolated monobodies to the coactivator motif strongly suggests that these monobodies directly bind to ERα. In contrast, monobodies identified from screening in the presence of OHT contain an amino acid sequence that is distinctly different from the LXXLL (SEQ ID No: 20) motif. These sequences do not show obvious homology to those of linear peptides selected for binding to the ERα/OHT complex by Norris et al. (1999).

TABLE 2

Estrogen Receptor-Binding Clones Obtained from the pYT45AB7N Library

| Clone Name | Amino Acid Sequence in the AB Loop |
|---|---|
| | $P_{15}$-------$T_{16}$ (wildtype) |
| | PXXXXXXXT (library) |
| A1 | WTWVLRE (SEQ ID No: 34) |
| B1 | WVLITRS (SEQ ID No: 35) |

Note: Library denotes residues 17-25 in SEQ ID No: 9.

TABLE 1

Estrogen Receptor-Binding Clones Obtained from the pFNB42B5F7 Library

| Initial Screen | Clone Name | Amino Acid Sequence | | Binding Specificity* | |
|---|---|---|---|---|---|
| | | BC loop | FG loop | E2 | ICI |
| E2 | B1 | AVTVR (wild type) | GILEMLQ (SEQ ID No: 25) | + | ND |
| E2 | C2 | WYQGR (SEQ ID No: 22) | RLRAQLV (SEQ ID No: 26) | + | ND |
| E2 | D1 | AVTVR (wild type) | PVRVLLR (SEQ ID No: 27) | + | ND |
| E2 | E1 | PRTKQ (SEQ ID No: 23) | RLRDLLQ (SEQ ID No: 28) | + | ND |
| ICI | A4 (=E1) | PRTKQ (SEQ ID No: 23) | RLRDLLQ (SEQ ID No: 28) | + | ND |
| IGI | A6 | AVTVR (wild type) | GLVSLLR (SEQ ID No: 29) | + | ND |
| ICI | B3 | AVTVR (wild type) | RKVVWTG (SEQ ID No: 30) | − | WEAK |
| ICI | C3 | VRRPP (SEQ ID No: 24) | TAAIMVK (SEQ ID No: 31) | − | WEAK |

*Binding specificity of the obtained clones were determined using survival assay.
Note: wild-type refers to residues 26-30 of SEQ ID No: 2.

TABLE 3

Estrogen Receptor-Binding Clones Obtained from the pYT45B3F7 Library

| Initial Screen | Clone Name | Amino Acids Sequence in IFG Loop | Binding Specificity* | | | | | |
|---|---|---|---|---|---|---|---|---|
| | | | E2 | DES | Gen | ICI | OHT | No Ligand |
| E2 | 23,31,E31,3,4,5 | LRLMLAG (SEQ ID No: 36) | + | + | + | + | – | – |
| E2 | F2-2#3 | ALVEMLR (SEQ ID No: 37) | + | + | + | – | – | – |
| E2 | F2-2#4 | RLLWNSL (SEQ ID No: 38) | + | + | + | – | – | – |
| E2 | F2-2#5, Gen1 H4 | RVLMTLL (SEQ ID No: 39) | + | + | + | ? | – | – |
| E2 | F2-2#7,#12 | GLRRLLR (SEQ ID No: 40) | + | + | + | ? | – | – |
| E2 | F2-2#8 | GLRQMLG (SEQ ID No: 41) | + | + | + | + | – | – |
| E2 | F2-2#9 | RVLHSLL (SEQ ID No: 42) | + | ND | ND | + | – | – |
| E2 | F2-2#10 | RVRDLLM (SEQ ID No: 43) | + | ND | ND | weak+ | – | – |
| E2 | F2-2#11 | RVMDMLL (SEQ ID No: 44) | + | ND | ND | + | – | – |
| E3 | 2 | GIAELLR (SEQ ID No: 45) | + | + | + | + | – | – |
| E3 | 6,7 | RILLNMLT (SEQ ID No: 46) | + | + | + | + | + | + |
| OHT | 31 | GGWLWCVT (SEQ ID No: 47) | – | – | – | + | + | – |
| OHT | 32 | TWVVRRV (SEQ ID No: 48) | – | – | – | + | + | – |
| OHT | 33 | TWVRPNQ (SEQ ID No: 49) | – | – | – | + | + | – |
| ICI | 16-3A | RRVPIWC (SEQ ID No: 50) | + | + | + | + | – | – |
| Genistein D1 | | RRVYDFL (SEQ ID No: 51) | + | | + | | | – |
| Genistein E1 | | LRQMLAD (SEQ ID No: 52) | + | | + | | | – |
| Genistein E4,D6 | | GLRMLLR (SEQ ID No: 53) | + | | + | | | – |

All the clones obtained from these screening trials contained the wild-type sequence in the BC loop.
*Binding specificity of the obtained clones were determined using survival assay.
Abbreviations for ligands are: E2, 17β-estradiol; E3, estriol; DES, diethyistilbestrol; Gen, Genistein; ICI, ICI182,780; OHT, 4-hydroxy tamoxifen.

TABLE 4

Estrogen Receptor-Binding Clones Obtained From the pYT47F16 Library

| Initial Screen | Clone Name | Amino Acids Sequence in FG Loop | Binding Specificity* | | | | | |
|---|---|---|---|---|---|---|---|---|
| | | | E2 | DES | Gen. | ICI | OHT | No Ligand |
| E2 | 45 | SRRLVEHLAGVEVQAL (SEQ ID No: 54) | + | + | + | + | – | – |
| E2 | 27 | LVARMLDWSDGEEASP (SEQ ID No: 55) | + | + | + | + | – | – |
| E2 | 48 | QGKGRRRGLVLYLLGS (SEQ ID No: 56) | + | + | + | + | – | – |
| E2 | B | RLRELLAEAAQASDGE (SEQ ID No: 57) | + | + | + | + | – | – |
| E2 | 2 | LLLRVGCGCRLVGSVL (SEQ ID No: 58) | + | + | + | + | – | – |
| E2 | 6 | RLSIVPCPAWARLTVL (SEQ ID No: 59) | + | + | + | + | + | – |
| E2 | 11 | LLVGLLLLRGARSGST (SEQ ID No: 60) | + | + | ? | + | – | – |
| E3 | 12 | LIYGLLSQPEERDEWR (SEQ ID No: 61) | + | + | ? | + | – | – |
| E3 | 13 | RSDGVLLRLLAGQRNA (SEQ ID No: 62) | + | + | + | + | – | – |
| E3 | 14 | WFDHERHGMLWQLLLR (SEQ ID No: 63) | + | + | + | + | – | – |

TABLE 4-continued

Estrogen Receptor-Binding Clones Obtained From the pYT47F16 Library

| Initial Screen | Clone Name | Amino Acids Sequence in FG Loop | Binding Specificity* | | | | | |
|---|---|---|---|---|---|---|---|---|
| | | | E2 | DES | Gen. | ICI | OHT | No Ligand |
| E3 | 15 | RLWCLLQRKGRNPIDM (SEQ ID No: 64) | + | + | + | + | − | − |
| OHT | 13,14,20 | RVFFGIGCRGGTGGGN (SEQ ID No: 65) | − | − | − | − | + | − |
| OHT | 21 | RVRFRCGGRDAASGDQ (SEQ ID No: 66) | − | − | − | − | + | − |
| OHT | 1,5 | LVRFRVVNSSLCMWAR (SEQ ID No: 67) | − | − | − | − | + | − |
| OHT | 2 | LVRLGVAGHMDAGAGR (SEQ ID No: 68) | − | − | − | − | + | − |
| OHT | 4,22 | PADGSEVLRLVKIHYV (SEQ ID No: 69) | − | − | − | − | + | − |
| OHT | 24 | RLEYGDVIGAVWWGRV (SEQ ID No: 70) | − | ND | ND | − | + | − |
| OHT | 3 | QGAAVRTLVAGGGVAS (SEQ ID No: 71) | + | + | + | + | + | − |
| OHT | 6 | LEVRVAAGCIAGGGRR (SEQ ID No: 72) | + | + | + | + | + | − |
| ICI | 16-4B | RLWRMLSGEPARVDHE (SEQ ID No: 73) | + | + | + | + | + | + |

*Binding specificity of the obtained clones were determined using survival assay.
Abbreviations for ligands are: E2, 17β-estradiol; E3, estriol; DES, diethylstilbestrol; Gen., Genistein; ICI, ICI 182, 780; OHT, 4-hydroxy tamoxifen.

EXAMPLE 3

Discrimination of Estrogen Receptor-α Conformations in Living Cells Using Conformation-Specific Monobodies The binding specificity of the monobodies toward different ERα-EF/ligand complexes was examined using quantitative β-galactosidase assays. It has been shown that the β-galactosidase activity correlates well with the interaction affinity between the bait and prey of the yeast two-hybrid system (Estojak et al., 1995), allowing an in vivo discrimination of interaction affinity. To minimize the effect of different ligands on the expression level and degradation of the LexA-ER fusion protein, β-galactosidase activity was determined after a short incubation period (6 hours) following the addition of a ligand and the initiation of monobody production. It was confirmed that yeast samples prepared in the presence and absence of ligands contained similar levels of ERα-EF protein (FIG. 14H). In addition, it was found that these ligands have little effect on the expression level of monobodies.

Figure 14A:
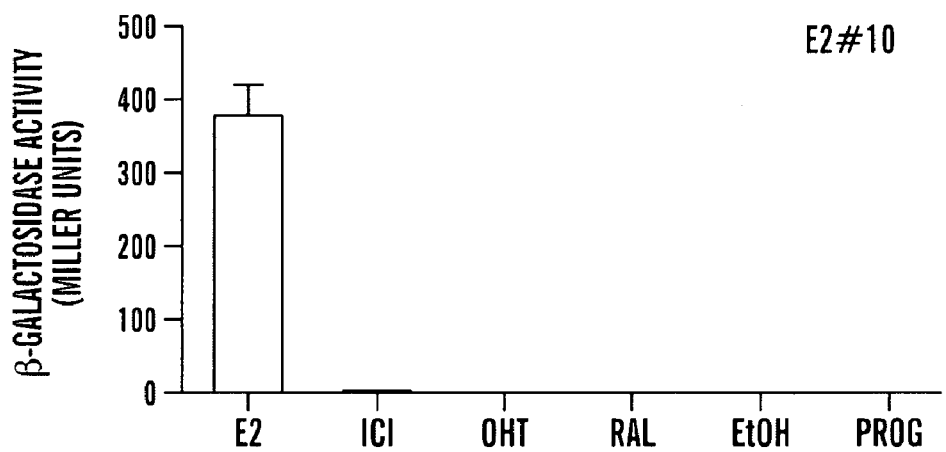
FIGS. 14A-H illustrate the in vivo binding specificity of ERα-binding monobodies, as tested using quantitative β-galactosidase assays.
Figure 14B:
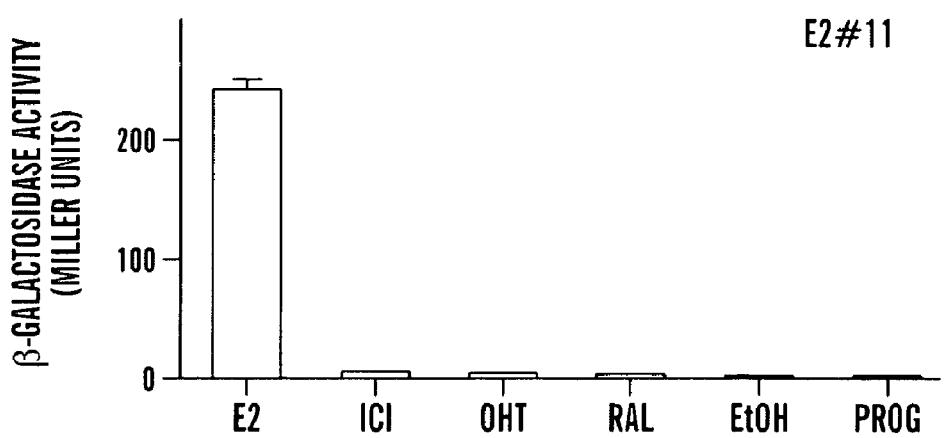
Figure 14C:
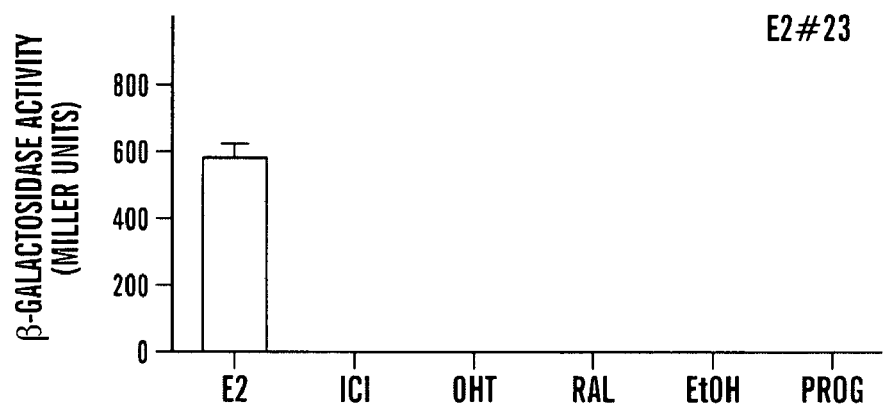
Figure 14D:
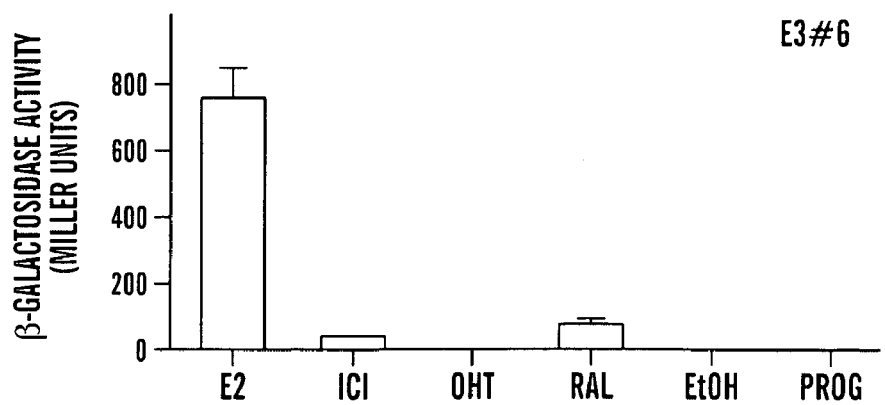
Figure 14E:
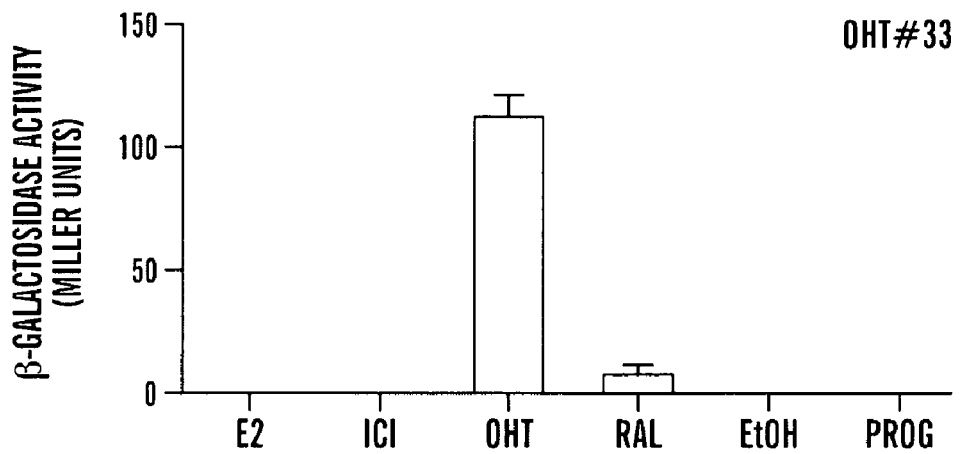
Figure 14F:
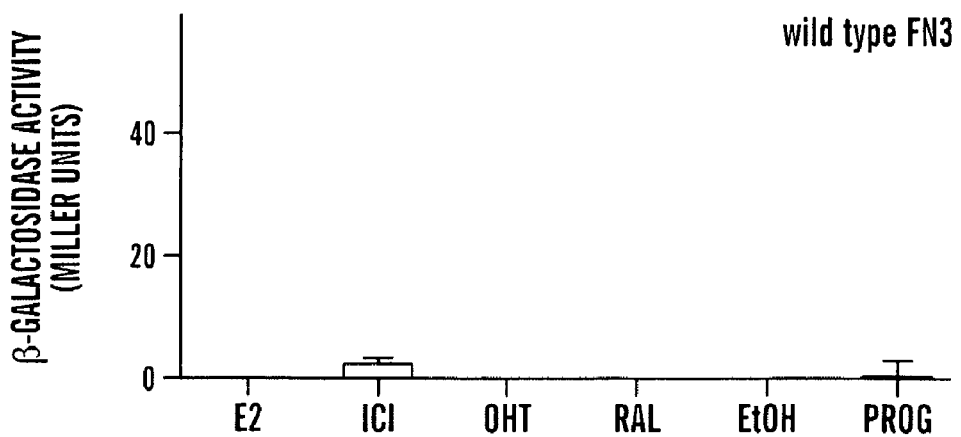
Figure 14G:
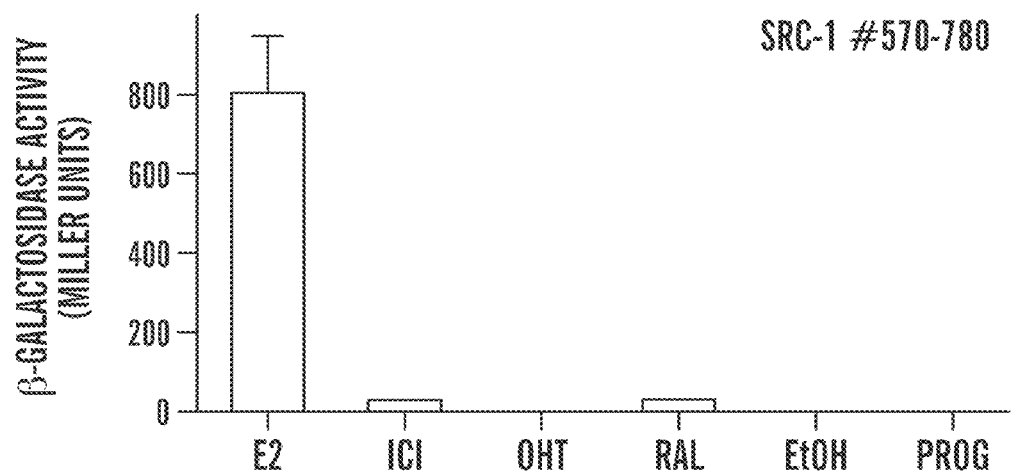
Figure 14H:
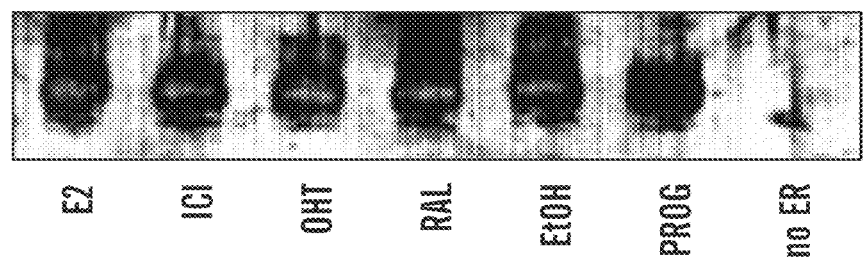

The in vivo interaction between these monobody clones and ERα-EF was tested in the presence of different ERα ligands (FIGS. 14A-G). In general, monobody clones selected for an ERα-EF/agonist (E2 and estriol) complex interacted with ERα-EF in the presence of E2, but not in the presence of OHT or other antagonists. The binding specificity of these clones is similar to that of the NR-box fragment of the coactivator, SRC-1, suggesting that these clones recognize a surface of ER-LBD that is used for coactivator binding. The clone, E3#6, showed weak but significant interaction with the ERα-EF/raloxifene complex (FIG. 14D). In an analogous manner, monobodies selected for the ERα-EF/OHT complex were specific to the same complex (FIG. 14E). In addition, the affinity of the selected monobodies to an unrelated protein (the pBait control protein; Origene) was below the detection limit of our assay.

Figure 15A:
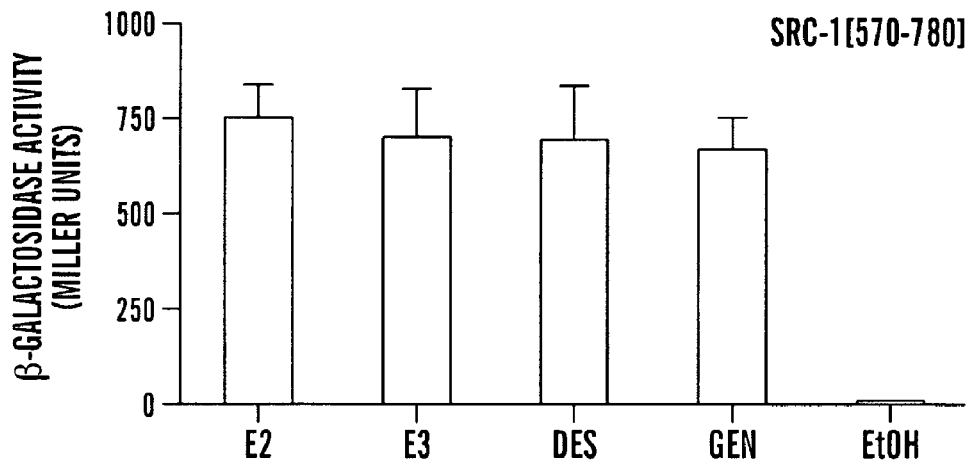
Figure 15B:
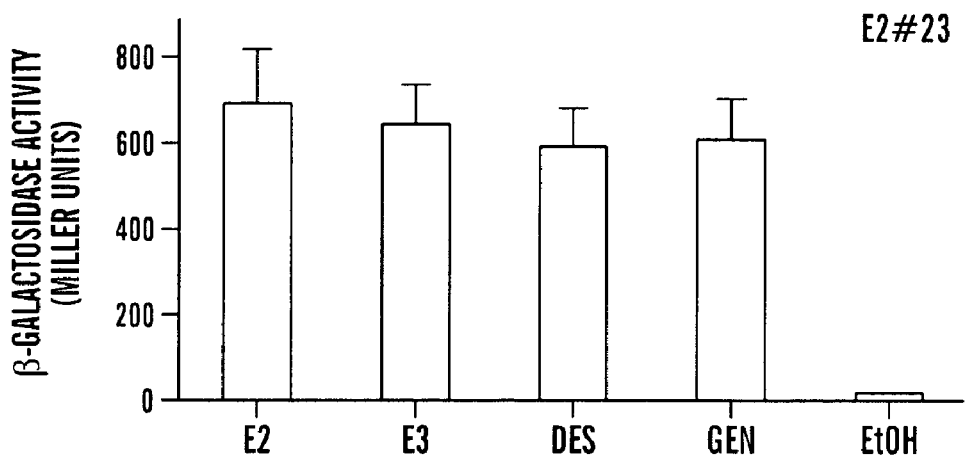
Figure 15C:
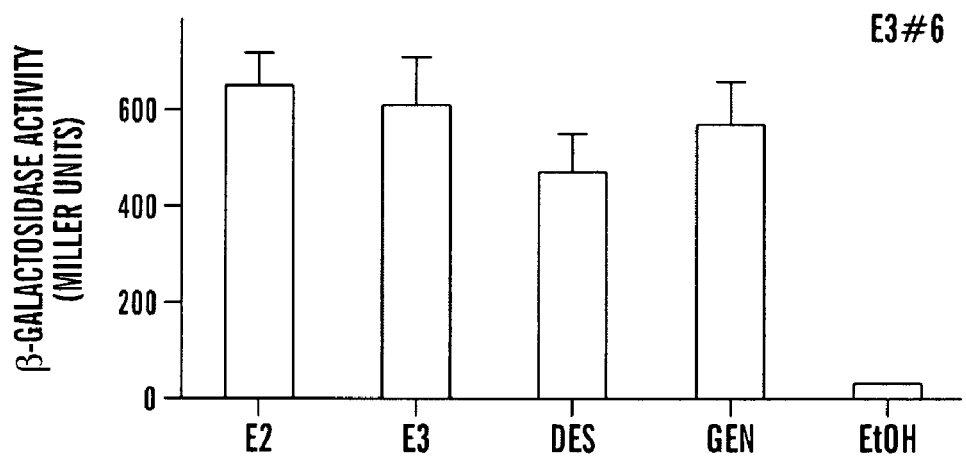
Figure 15D:
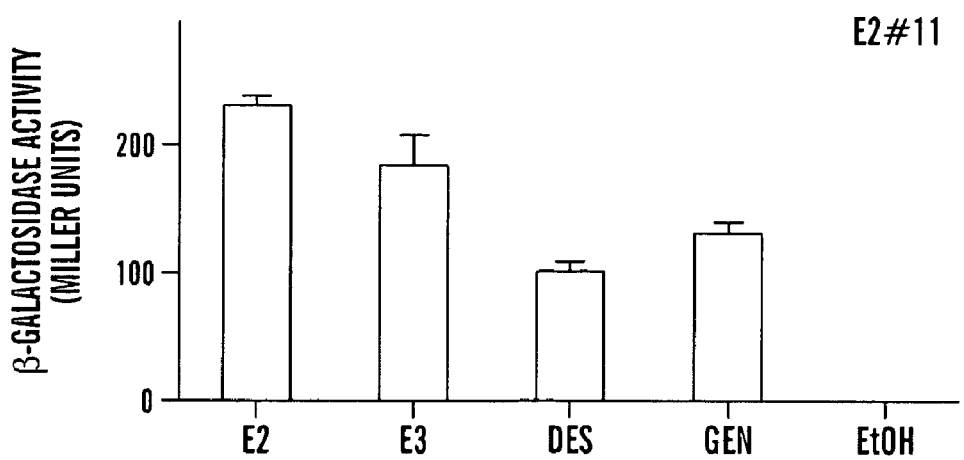

The effects of different agonists on the interactions between ERα-EF and monobodies were also tested (FIGS. 15A-D). Clone E2#11 showed different reactivity to different agonist-complexes of ERα-EF (FIG. 15D), while clone E2#23 and the NR-box fragment of coactivator SRC-1 bind equally well to these agonist complexes (FIGS. 15A-C). Taken together, these results demonstrate that one can isolate monobodies that are specific to different conformations of ERα-EF, and that one can use such monobodies to detect conformational differences of ERα-EF in the nucleus induced by various ligands, even small changes induced by different agonists.

Figure 18A:
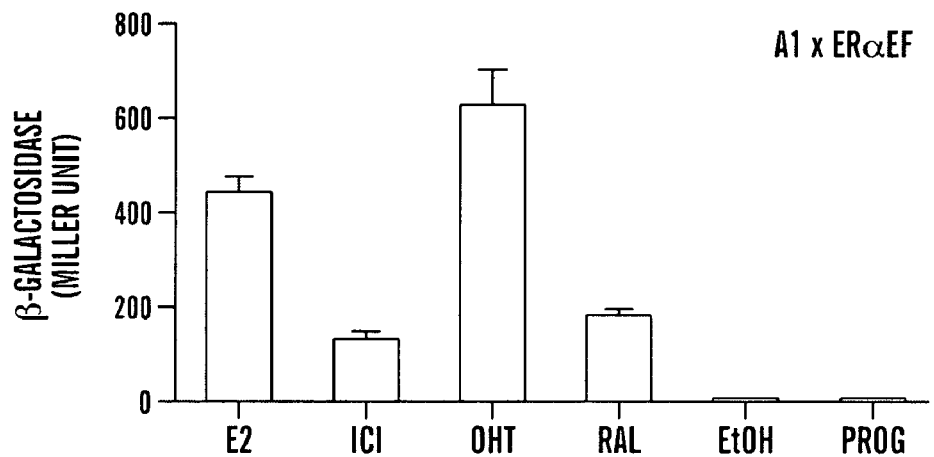
Figure 18B:
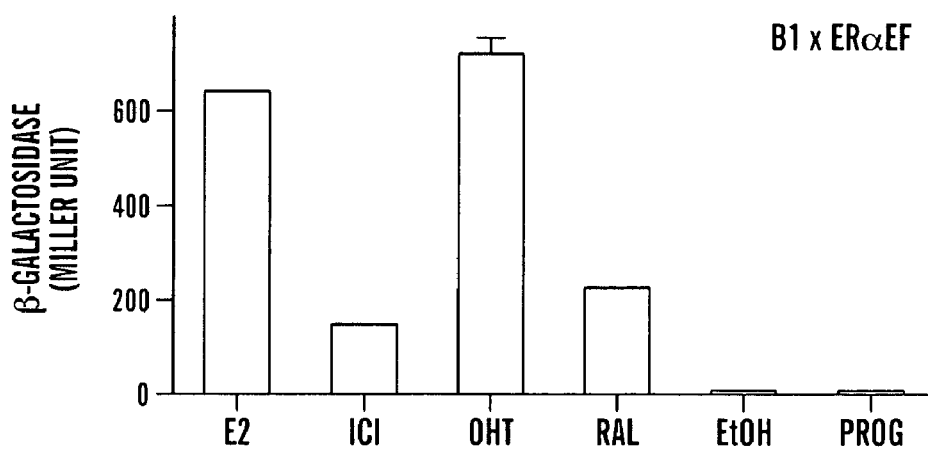
Figure 18C:
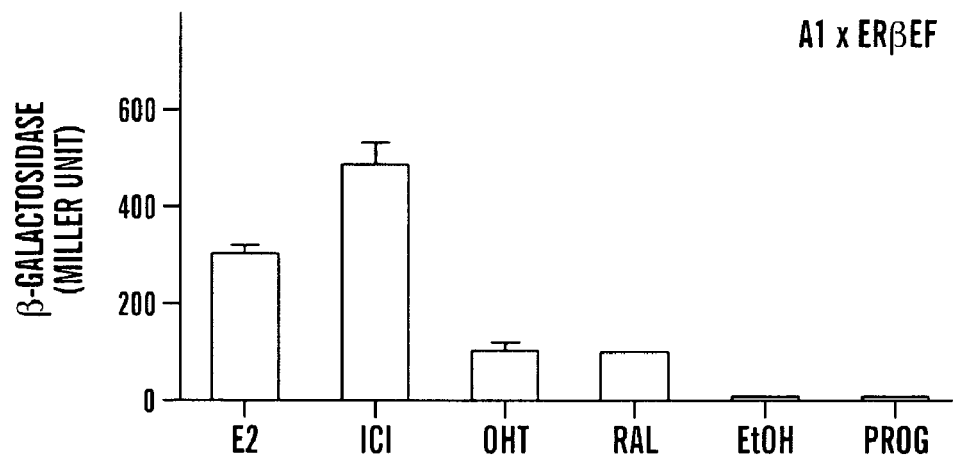
Figure 18D:
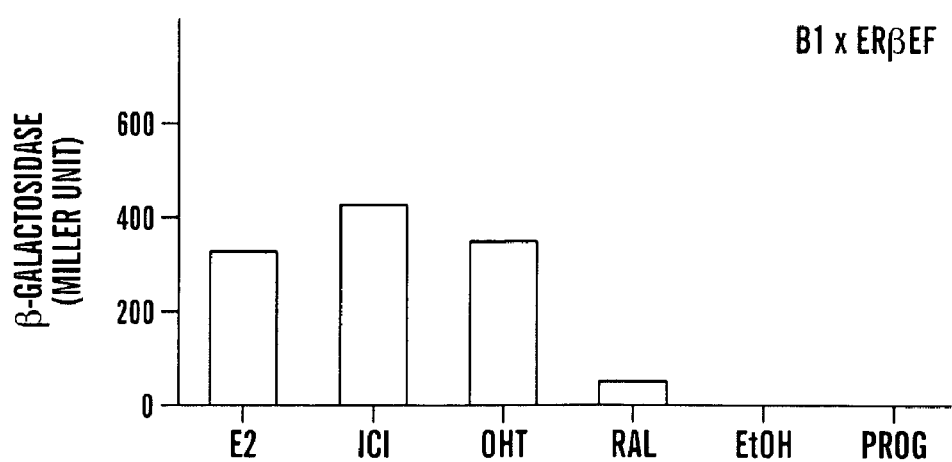

The profile (FIG. 18A-B) of in vivo interaction between ERα-EF and monobodies from the pYT45AB7N library (Table 2) were distinct from those between ERα-EF and monobodies from the other libraries (FIGS. 14A-H). The two monobodies, A1 and B1, from the pYT45AB7N library were selected in the presence of estradiol. Nevertheless, they do not contain the consensus LXXLL (SEQ ID No:20)-like sequence (Table 2). Moreover, A1 and B11 bind equally well to the estradiol- and hydroxytamoxifen-complexes of ERα-EF (FIGS. 18A-B). These results demonstrate that monobodies with distinct functions can be obtained by screening libraries in which different loop regions are diversified.

Furthermore, the interaction specificity of these two monobodies to ERα and ERβ is quite different (compare FIGS. 18A-B with 18C-D). These results suggest that these monobodies can discriminate the surface properties of ERα from those of ERβ. ERβ cDNA clone was kindly provided by Dr. M. Muyan of the University of Rochester Medical Center. A prey plasmid, pEGERβ248-530, was constructed by cloning the DNA fragment corresponding to the EF domains of ERβ

(residues 248-530) into pEG202 in the same manner as for construction of pEGERα297-554.

Example 4

Roles of the F Domain on the Conformational Dynamics of the Estrogen Receptor-α Ligand-Binding Domain The affects of the F domain (residues 551-595) on interactions of monobodies with the LBD (the E domain) of ERα was tested. The β-galactosidase activity of cells containing a LexA-ERα E domain fusion protein and a monobody-activation domain fusion protein was compared to the β-galactosidase activity of cells containing LexA-ERα-EF and the same monobody-activation domain fusion protein (FIGS. 16A-E). It was confirmed that the expression levels of ERα-E and -EF bait proteins were similar, and that the cells containing the ERα-EF fusion protein do not have breakdown products similar to the ERα-E fusion protein (FIG. 16E). In the presence of E2, the deletion of the F domain had little effect on the interactions of E2#23, E3#6 and SRC-1 with the ERα fragments (FIGS. 16A-C), suggesting that the F domain does not constitute the binding site for these proteins. In contrast, the deletion of the F domain resulted in a significant increase (more than 100-fold in β-galactosidase activity) in binding of E3#6 and SRC-1 to ERα in the absence of a bound ligand (FIGS. 16A-B). A somewhat similar effect of the F domain was observed for the binding of the clone OHT#33. OHT#33 interactions were similar with ERα-E and ERα-EF in the presence of OHT, while the interaction of this monobody with the ERα-E/raloxifene complex was significantly greater than that with the ERα-EF/raloxifene complex (FIG. 16D). In contrast to the data with monobodies that bind to ERα/agonist complexes, the deletion did not increase the interaction of OHT#33 and ERα in the absence of a ligand.

Example 5

Use of Polypeptide Monobodies as Sensors

As described above, the collection of yeast strains that respond differently to different ER-ligand complexes can potentially be used as sensors for ER ligands. As shown in FIGS. 17A-D, arrays of yeast can be grown on a solid medium, with each colony expressing a particular monobody having an affinity for ER-α in the presence of an agonist or antagonist. The array in FIG. 17A shows β-galactosidase activity in the absence of an agonist or antagonist, whereas the array in FIG. 17B shows no β-galactosidase activity in the absence of an agonist or antagonist. FIGS. 17C-D demonstrate, respectively, detectable β-galactosidase activity in the presence of E2 (agonist) and OHT (antagonist). Thus, it is possible to identify new agonist or antagonist compounds which have an affinity for the ER-α based upon their interaction with yeast expressing both a LexA-ERα E or EF domain fusion protein and a monobody-activation domain fusion protein. New agonists having E2-like binding should produce results similar to those shown in FIG. 17C, whereas new antagonist having OHT-like binding should produce results similar to those shown in FIG. 17D.

Example 6

Use of Polypeptide Monobodies to Modulate Estrogen Receptor Interactions

The interaction between ER and the natural coactivator, SRC-1, was examined in the presence of a polypeptide monobody. The yeast two-hybrid system that monitored the interaction between ERα-EF and SRC-1 was used. The monobody E2#23 was co-expressed under the control of a separate promotor. β-Galactosidase activity in the presence of E2 decreased by approximately 30% when the monobody was expressed, while co-expression of the wild-type FNfn10 did not alter the level of the marker enzyme activity. This inhibitory effect was reduced when the expression level of the SRC-1-activation domain fusion was increased. These results suggest that the monobody binds to the coactivator-binding site of ERα in a competitive manner against SRC-1. It is likely that increased expression levels of the monobodies would further augment the observed inhibition. Thus, these results suggest that it monobody-based inhibitors of nuclear receptors can be developed.

Thus, a collection of yeast two-hybrid cells containing a nuclear receptor ligand binding domain and an appropriate monobody can be used for screening of drug-like molecules (Chen et al., 1997; Nishikawa et al., 1999). By expressing the nuclear receptor in yeast, the system is not limited by the presence of a natural protein that interacts with the nuclear receptor in the presence of a particular ligand. Thus, it should be possible to develop screening systems for chemicals that induce a nuclear receptor into a conformation similar to that induced by a known nuclear receptor ligand.

Discussion of Examples 1-6

The above Examples demonstrate monobodies that are specific to a particular conformation of ERα can be obtained, and that one can probe conformational changes of ERα in living cells using such monobodies. The ability of detecting conformational changes of proteins in the native environment should bridge the gap that currently exists between high-resolution structural information obtained from in vitro techniques and functional information from cell biology studies. The use of engineered probes for conformational change, such as monobodies described here, allow discrimination of a wider variety of conformations than those that are responsible for interactions of the target protein with other natural proteins. In addition to probing ligand-induced conformational changes, the above-demonstrated approach can detect effects of mutations, e.g., the deletion of the F domain.

Figure 13B:
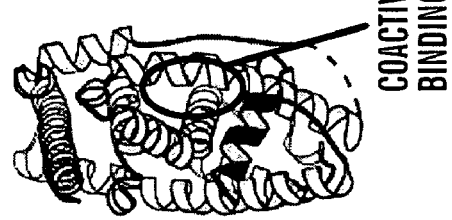

In the present study, a yeast two-hybrid system was used as the means to detect interactions of monobodies with a target in living cells. The yeast two-hybrid system detects interactions in the nucleus. This is ideally suited for the investigation of conformational changes of nuclear receptors that function in the nucleus. Clearly, this work can be extended using the mammalian two-hybrid method. However, alternative methods may be better suited for probing conformational changes of proteins that are naturally located outside the nucleus. Potential methods include the split ubiquitin system (Johnsson & Varshavsky, 1994) and dihydroforate reductase reconstitution (Pelletier et al., 1998). Indeed, Raquet et al. reported the use of the split-ubiquitin system to detect conformational differences of a protein in living cells (Raquet et al., 2001). The present invention, using conformation-specific monobodies, could readily be adapted to these systems. The conformational changes of ERα-E and ERα-EF as discriminated by the above-identified monobody collection generally agree with the conformational differences of ERα- and ERβ-E domains found in a series of crystal structures. Thus, the above results support that these crystal structures represent relevant conformations of ER in cells. However, a dramatic increase in the interactions of the monobody E3#6 and ERα was identified upon the deletion of the F domain (FIG. 14). A similar effect was observed between SRC-1 and ERα. These results may be interpreted as a dynamic conformational equilibrium, in which ERα-E, in particular, helix 12 (FIGS. 13A-B) is in equilibrium among multiple conformations and the presence of the F domain shifts this equilibrium away from the "active" conformation. A number of mutations at residues 536 and 537, which are located in the loop connecting helices 11 and 12, resulted in a constitutively active phenotype (Weis et al., 1996; White et al., 1997; Zhang et al., 1997; Eng et al., 1997), suggesting that these mutations can shift the conformational equilibrium within the LBD. A series of ERβ LBD crystal structures also suggest the dynamic nature of helix 12. In the genistein complex (Shiau et al., 1998), helix 12 is in a position similar to that found in the ERβ-antagonist structure, as opposed to the "agonist" conformation that is expected from the partial agonist activity of genistein. In the structure of ERβ bound to an antagonist, ICI164,384, the electron density for the entire helix 12 is missing, suggesting a conformational disorder (Pike et al., 2001). Furthermore, an NMR study of the LBD of peroxisome proliferator-activated receptor γ, another member of the nuclear receptor family, revealed that the apo-LBD, particularly ligand- and cofactor-binding regions, is in a dynamic conformational ensemble (Johnson et al., 2000). Since the F domain of ERα is quite large (~45 residues) and it is directly linked to helix 12, it is plausible that the F domain can affect the balance of the conformational ensemble of the E domain even if the F domain is largely unstructured. It should be noted that the observed effect of the F-domain deletion may be mediated through a change in association of ERα with other macromolecules such as heat shock proteins. These results demonstrate that our approach can reveal conformational dynamics of a target protein in living cells, and thus it can provide useful information complementary to static information obtained from X-ray crystal structure.

The above results (FIGS. 14-16) demonstrate that different agonists induce somewhat different conformations of ERα-EF, and that a subset of monobodies are capable of detecting such structural differences. It is interesting that the clone E2#11, which gave the lowest β-galactosidase activity among those tested, was most sensitive to the differences among these agonist complexes. These results suggest that monobodies with weak binding affinity may be quite useful for detecting subtle conformational differences, consistent with the presence of a dynamic conformational ensemble. They also suggest that the energetic barrier among the ERα conformations induced by these agonists may be quite low so that monobodies and coactivators that bind tightly to ERα may be able to promote the "induced fit" of the ERα conformation. Paige et al. have shown that these agonists induce distinct conformations in full-length ERα and ERβ that are detectable using in vitro binding assays of ER-binding peptides (Paige et al., 1999).

The above result also demonstrate that monobodies can be used as modulators of biological functions. Although the inhibitory activity of the first-generation monobody was modest, the binding affinity and specificity of monobodies could be improved by introducing additional mutations in adjacent loops (see FIGS. 1A-B) and performing further rounds of selection with a higher degree of stringency. Prior studies have demonstrated that the monobody scaffold can accommodate many mutations in multiple loops (Koide et al., 1998). Peptide aptamers based on a single loop and antibody fragments ("intrabodies") have been shown to be effective inhibitors of intracellular processes (Colas et al., 1996; Richardson & Marasco, 1995). Therefore, monobodies with potent inhibitory activity can also be developed.

LIST OF REFERENCES

Each of the references listed below is hereby incorporated by reference in its entirety into the specification of this application.

Anstead, G. M., Carlson, K. E. & Katzenellenbogen, J. A. (1997) *Steroids* 62, 268-303.

Aukhil, I., Joshi, P., Yan, Y. & Erickson, H. P. (1993) *J. Biol. Chem.* 268, 2542-2553.

Bangham et al. (1965) *J. Mol. Biol.* 13, 238-252.

Baron, M., Norman, G. D., & Campbell, I. D. (1991) *Trends Biochem. Sci.* 16, 13-17.

Berkner, K. L. (1988) *Biotechniques* 6, 616-627.

Bendixen, C., Gangloff, S. & Rothstein, R. (1994) *Nucl. Acids Res.* 22, 1778-1779.

Bork, P. & Doolittle, R. F. (1992) *Proc. Natl. Acad. Sci. USA* 89, 8990-8994.

Bork, P., Hom, L. & Sander, C. (1994) *J. Mol. Biol.* 242, 309-320.

Campbell, I. D. & Spitzfaden, C. (1994) *Structure* 2, 333-337.

Chen, C. W., Hurd, C., Vorojeikina, D. P., Arnold, S. F. & Notides, A. C. (1997) *Biochem. Pharmacol.* 53, 1161-1172.

Chien, C. T., Bartel, P. L., Stemglanz, R. & Fields, S. (1991) *Proc. Natl. Acad. Sci. USA* 11, 9578-9582.

Cochet, O., Kenigsberg, M., Delumeau, I., Virone-Oddos, A., Multon, M. C., Fridman, W. H., Schweighoffer, F., Teillaud, J. L. & Tocque, B. (1998) *Cancer Res* 58, 1170-1176.

Colas, P., Cohen, B., Jessen, T., Grishina, I., McCoy, J. & Brent, R. (1996) *Nature* 380, 548-550.

Colas, P. & Brent, R. (1998) *Trends Biotechnol.* 16, 355-363.

Deng, W. P. & Nickoloff, J. A. (1992) *Anal. Biochem.* 200, 81-88.

de Vos, A. M., Ultsch, M. & Kossiakoff, A. A. (1992) *Science* 255, 306-12.

Dickinson, C. D., Veerapandian, B., Dai, X. P., Hamlin, R. C., Xuong, N. H., Ruoslahti, E. & Ely, K. R. (1994) *J. Mol. Biol.* 236, 1079-1092.

Eng, F. C., Lee, H. S., Ferrara, J., Willson, T. M. & White, J. H. (1997) *Mol. Cell. Biol.* 17, 4644-4653.

Estojak, J., Brent, R. & Golemis, E. A. (1995) *Mol. Cell. Biol.* 15, 5820-5829.

Fabbrizio, E., Le Cam, L., Polanowska, J., Kaczorek, M., Lamb, N., Brent, R. & Sardet, C. (1999) *Oncogene* 18, 4357-63

Fields, S. & Song, O. (1989) *Nature* 340, 245-246.

Finley, R. L., Jr. & Brent, R. (1994) *Proc. Natl. Acad. Sci. USA* 91, 12980-12984.

Flotte, T. R., Afione, S. A., Conrad, C., McGrath, S. A., Solow, R., Oka, H., Zeitlin, P. L., Guggino, W. B., Carter, B. J., (1993) *Proc. Nat'l Acad. Sci. U.S.A* 90, 10613-10617.

Ghosh, G., Van Duyne, G., Ghosh, S. & Sigler, P. B. (1995) *Nature* 373, 303-310.

Gietz, R. D. & Sugino, A. (1988) *Gene* 74, 527-534.

Golemis, E. & Serebriiskii, I. (1997) in *Two-hybrid system/interaction trap* (CSH Laboratory Press, Cold Spring Harbor, N.Y.), pp. 69.61-40.

Gribskov, M., Devereux, J. & Burgess, R. R. (1984) *Nucl. Acids Res.* 12, 539-549.

Gyuris, J., Golemis, E., Chertkov, H. & Brent, R. (1993) *Cell* 75, 791-803.

Harpez, Y. & Chothia, C. (1994) *J. Mol. Biol.* 238, 528-539.

Heery, D. M., Kalkhoven, E., Hoare, S. & Parker, M. G. (1997) *Nature* 387, 733-736.

Johnson, B. A., Wilson, E. M., Li, Y., Moller, D. E., Smith, R. G. & Zhou, G. (2000) *J. Mol. Biol.* 298, 187-194.

Johnsson, N. & Varshavsky, A. (1994) *Proc. Natl. Acad. Sci. USA* 91, 10340-10344.

Jones, E. Y. (1993) *Curr. Opinion Struct. Biol.* 3, 846-852.

Jordan, V. C., Jeng, M. H., Jiang, S. Y., Yingling, J. & Stella, A. L. (1992) *Seminars Oncol.* 19, 299-307.

Jordan, V. C. (1998) *J. Natl. Cancer Inst.* 90, 967-971.

Kaplitt, M. G., Leone, P., Samulski, R. J., Xiao, X., Pfaff, D. W., O'Malley, K. L., During, M. J. (1994) *Nature Genet.* 8, 148-153 (1994).

Koide, A., Bailey, C. W., Huang, X. & Koide, S. (1998) *J. Mol. Biol.* 284, 1141-1151.

Koide, A., Jordan, M. R., Homer, S. R., Batori, V., Koide, S. (2001) *Biochem.* 40, 10326-10333.

Korach, K. (1994) *Science* 266, 1524-1527.

Kunkel, T. A., Roberts, J. D. & Zakour, R. A. (1987) *Methods Enzymol.* 154, 367-382.

Leahy, D. J., Hendrickson, W. A., Aukhil, I. & Erickson, H. P. (1992) *Science* 258, 987-991.

Main, A. L., Harvey, T. S., Baron, M., Boyd, J. & Campbell, I. D. (1992) *Cell* 71, 671-678.

Martzen, M. R., McCraith, S. M., Spinelli, S. L., Torres, F. M., Fields, S., Grayhack, E. J. & Phizicky, E. M. (1999) *Science* 286, 1153-1155.

Mendelsohn, A. R. & Brent, R. (1994) *Curr. Opin. Biotechnol.* 5, 482-486.

Mhashilkar, A. M., Bagley, J., Chen, S. Y., Szilvay, A. M., Helland, D. G. & Marasco, W. A. (1995) *EMBO J.* 14, 1542-51.

Minton, A. P. (2000) *Curr. Opin. Struct. Biol.* 10, 34-39.

Montano, M. M., Muller, V., Trobaugh, A. & Katzenellenbogen, B. S. (1995) *Mol. Endocrinol.* 9, 814-825.

Müller, C. W., Rey, F. A., Sodeoka, M., Verdine, G. L. & Harrison, S. C. (1995) *Nature* 373, 311-117.

Nichols, M., Rientjes, J. M., Logie, C. & Stewart, A. F. (1997) *Mol. Endocrinol.* 11, 950-961.

Nishikawa, J., Saito, K., Goto, J., Dakeyama, F., Matsuo, M. & Nishihara, T. (1999) *Toxicol Appl Pharmacol* 154, 76-83.

Norris, J. D., Paige, L. A., Christensen, D. J., Chang, C. Y., Huacani, M. R., Fan, D., Hamilton, P. T., Fowlkes, D. M. & McDonnell, D. P. (1999) *Science* 285, 744-746.

Onate, S. A., Tsai, S. Y., Tsai, M. J. & O'Malley, B. W. (1995) *Science* 270, 1354-1357.

Paige, L. A., Christensen, D. J., Gron, H., Norris, J. D., Gottlin, E. B., Padilla, K. M., Chang, C. Y., Ballas, L. M., Hamilton, P. T., McDonnell, D. P. & Fowlkes, D. M. (1999) *Proc. Natl. Acad. Sci. USA* 96, 3999-4004.

Pelletier, J. N., Campbell-Valois, F. X. & Michnick, S. W. (1998) *Proc. Natl. Acad. Sci. USA* 95, 12141-12146.

Pike, A. C., Brzozowski, A. M., Walton, J., Hubbard, R. E., Thorsell, A., Li, Y., Gustafsson, J. & Carlquist, M. (2001) *Structure* 9, 145-153.

Plaxco, K. W., Spitzfaden, C., Campbell, I. D. & Dobson, C. M. (1996) *Proc. Natl. Acad. Sci. USA* 93, 10703-10706.

Raquet, X., Eckert, J. H., Muller, S. & Johnsson, N. (2001) *J. Mol. Biol.* 305, 927-938.

Richardson, J. H. & Marasco, W. A. (1995) *Trends Biotechnol.* 13, 306-310.

Roberts, T. M. & Lauer, G. D. (1979) *Methods in Enzymology* 68, 473-482.

Rosenfeld, M. A., Siegfried, W., Yoshimura, K., Yoneyama, K., Fukayama, M., Stier, L. E., Paakko, P. K., Gilardi, P., Stratford-Perricaudet, L. D., Perricaudet, M., et al. (1991) *Science* 252, 431-434.

Sachs, D. H., Schechter, A. N., Eastlake, A. & Anfinsen, C. B. (1972) *Proc. Natl. Acad. Sci. USA* 69, 3790-3794.

Sambrook, J., Fritsch, E. F. & Maniatis, T. (1989) *Molecular Cloning: A laboratory manual*, 2nd Ed. (Cold Spring Harbor Laboratory, Cold Spring Harbor).

Sandhu, G. S., Aleff, R. A. & Kline, B. C. (1992) *BioTech* 12, 14-16.

Shiau, A. K., Barstad, D., Loria, P. M., Cheng, L., Kushner, P. J., Agard, D. A. & Greene, G. L. (1998) *Cell* 95, 927-937.

Takebe, Y., Seiki, M., Fujisawa, J., Hoy, P., Yokota, K., Arai, K., Yoshida, M. & Arai, N. (1988) *Mol. Cell. Biol.* 8, 466-472.

Tanenbaum, D. M., Wang, Y., Williams, S. P. & Sigler, P. B. (1998) *Proc. Natl. Acad. Sci. USA* 95, 5998-6003.

Uetz, P. & Hughes, R. E. (2000) *Curr. Opin. Microbiol.* 3, 303-308.

Wang, C. Y. & Huang, L. (1987) *Proc. Natl. Acad. Sci. USA* 84, 7851-7855.

Weis, K. E., Ekena, K., Thomas, J. A., Lazennec, G. & Katzenellenbogen, B. S. (1996) *Mol. Endocrinol.* 10, 1388-1398.

White, R., Sjoberg, M., Kalkhoven, E. & Parker, M. G. (1997) *EMBO J.* 16, 1427-1435.

Williams, A. F., Barclay, A. N. (1988) *Ann. Rev. Immunol.* 6, 381-405.

Zhang, Q. X., Borg, A., Wolf, D. M., Oesterreich, S. & Fuqua, S. A. (1997) *Cancer Res.* 57, 1244-1249.

U.S. Pat. No. 6,114,111 to Luo et al.
U.S. Pat. No. 6,057,155 to Wickham et al.
U.S. Pat. No. 6,033,908 to Bout et al.
U.S. Pat. No. 6,001,557 to Wilson et al.
U.S. Pat. No. 5,994,132 to Chamberlain et al.
U.S. Pat. No. 5,981,225 to Kochanek et al.
U.S. Pat. No. 5,885,808 to Spooner et al.
U.S. Pat. No. 5,885,613 to Holland et al.
U.S. Pat. No. 5,871,727 to Curiel
U.S. Pat. No. 5,849,586 to Kriegler et al.
U.S. Pat. No. 5,817,789 to Heartlein et al.
U.S. Pat. No. 5,681,811 to Ekwuribe
U.S. Pat. No. 5,653,996 to Hsu et al.
U.S. Pat. No. 5,643,599 to Lee et al.
U.S. Pat. No. 5,631,237 to Dzau et al.
U.S. Pat. No. 5,059,421 to Loughrey et al.
U.S. Pat. No. 4,237,224 to Cohen and Boyer Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A fibronectin type III (Fn3) polypeptide monobody derived from the amino acid sequence of SEQ ID NO: 2 or SEQ ID NO: 3, the polypeptide monobody comprising:
   at least two adjacent Fn3 β-strand domain sequences selected from the group of A (residues 9-14 of SEQ ID NO: 2 and SEQ ID NO: 3), B (residues 17-21 of SEQ ID NO: 2 and SEQ ID NO: 3), C (residues 31-38 of SEQ ID NO: 2 and SEQ ID NO: 3), D (residues 46-50 of SEQ ID NO: 2 and SEQ ID NO: 3), E (residues 55-59 of SEQ ID NO: 2 and SEQ ID NO: 3), F (residues 67-75 of SEQ ID NO: 2 and SEQ ID NO: 3), and G (residues 88-94 of SEQ ID NO: 2 and SEQ ID NO: 3), with an associated loop region sequence linked between each pair of adjacent β-strand domain sequences, each of the loop region sequences being selected from the group of loops AB (residues 15-16 of SEQ ID NO: 2 and SEQ ID NO: 3), BC (residues 22-30 of SEQ ID NO: 2 and SEQ ID NO: 3), CD (residues 39-45 of SEQ ID NO: 2 and SEQ ID NO: 3), DE (residues 51-54 of SEQ ID NO: 2 and SEQ ID NO: 3), EF (residues 60-66 of SEQ ID NO: 2 and SEQ ID NO: 3), and FG residues 76-87 of SEQ ID NO: 2 and SEQ ID NO: 3); and
   optionally, an N-terminal tail of at least about 2 to about 33 amino acids, a C-terminal tail of at least about 2 to about 25 amino acids, or both;
   wherein at least one loop region sequence comprises a modified amino acid sequence which varies from a corresponding loop region present in SEQ ID NO:2 or SEQ ID NO:3 by deletion of up to all but one amino acid residue, insertion of two to about 25 amino acid residues, or replacement of two to all amino acid residues, and
   wherein the polypeptide monobody exhibits estrogen receptor binding activity via interaction of the at least one loop region sequence with the estrogen receptor.

2. The polypeptide monobody according to claim 1, wherein the polypeptide monobody exhibits estrogen receptor binding activity in the presence of an estrogen receptor agonist or an extrogen receptor antagonist.

3. The polypeptide monobody according to claim 2, wherein the estrogen receptor agonist is estradiol, estriol, diethylstilbestrol, or genistein.

4. The polypeptide monobody according to claim 2, wherein the estrogen receptor antagonist is hydroxy tamoxifen, ICI182780, or raloxifene.

5. The polypeptide monobody according to claim 1, wherein said at least two Fn3 β-strand domain sequences comprises each of β-strand domain sequences A through G of SEQ ID NO: 2 or SEQ ID NO: 3, wherein the loop region sequences comprise the AB loop, BC loop, CD loop, DE loop, EF loop, and FG loop.

6. The polypeptide monobody according to claim 5, wherein the loop region sequence that comprises the modified amino acid sequence is selected from the group consisting of the AB loop region sequence, the BC loop region sequence, the DE loop region sequence, and the FG loop region sequence.

7. The polypeptide monobody according to claim 5, wherein the BC loop region sequence and the FG loop region sequence both comprise one of said modified amino acid sequences.

8. A fusion protein comprising:
   a first portion comprising a polypeptide monobody according to claim 1 and
   a second portion fused to the first portion.

9. The fusion protein according to claim 8, wherein the second portion comprises a label.

10. The fusion protein according to claim 9, wherein the label is an alkaline phosphatase tag or a $His_{(6)}$ tag.

11. The fusion protein according to claim 8, wherein the second portion comprises a transcriptional activation domain.

12. The polypeptide monobody according to claim 1, wherein the FG loop region sequence comprises the amino acid sequence selected from the group of SEQ ID NO: 20 and SEQ ID NO: 32.

13. The polypeptide monobody according to claim 1, wherein the BC loop region sequence comprises the amino acid sequence of SEQ ID NO: 23.

14. The polypeptide monobody according to claim 1, wherein the FG loop region sequence comprises the amino acid sequence of SEQ ID NO: 67.

15. The polypeptide monobody according to claim 1, wherein the AB loop region sequence comprises the amino acid sequence of SEQ ID NO: 34.

16. A fibronectin type III (Fn3) polypeptide monobody comprising the formula $\beta_A$-$L_{AB}$-$\beta_B$-$L_{BC}$-$\beta_C$-$L_{CD}$-$\beta_D$-$L_{DE}$-$\beta_E$-$L_{EF}$-$\beta_F$-$L_{FG}$-$\beta_G$, wherein:
   $\beta_A$, $\beta_B$, $\beta_C$, $\beta_D$, $\beta_E$, $\beta_F$, and $\beta_G$ are, respectively, β-strand domain sequences A through G of a tenth Fn3 domain of fibronectin; and
   $L_{AB}$, $L_{BC}$, $L_{CD}$, $L_{DE}$, $L_{EF}$, and $L_{FG}$ are, respectively, loop region sequences AB, BC, CD, DE, EF, and FG, wherein at least one loop region sequence selected from the group of AB, BC, and FG varies from a corresponding loop region present in the tenth Fn3 domain of fibronectin by deletion of up to all but one amino acid residue, insertion of two to about 25 amino acid residues, or replacement of two to all amino acid residues; and
   wherein the polypeptide monobody exhibits estrogen receptor binding activity via interaction of the at least one loop region sequence with the estrogen receptor.

17. The polypeptide monobody according to claim 1, wherein the BC loop region sequence comprises the amino acid sequence selected from the group of SEQ ID NO: 22 and SEQ ID NO: 24.

18. The polypeptide monobody according to claim 1, wherein the FG loop region sequence comprises the amino acid sequence selected from the group of SEQ ID NO:48 and SEQ ID NO:49.

19. The polypeptide monobody according to claim 1, wherein the AB loop region sequence comprises the amino acid sequence of SEQ ID NO: 35.

20. A fibronectin type III (Fn3) polypeptide monobody derived from the amino acid sequence of SEQ ID NO: 2 or SEQ ID NO: 3, the polypeptide monobody comprising:

at least two adjacent Fn3 β-strand domain sequences selected from the group of A (residues 9-14 of SEQ ID NO: 2 and SEQ ID NO: 3), B (residues 17-21 of SEQ ID NO: 2 and SEQ ID NO: 3), C (residues 31-38 of SEQ ID NO: 2 and SEQ ID NO: 3), D (residues 46-50 of SEQ ID NO: 2 and SEQ ID NO: 3), E (residues 55-59 of SEQ ID NO: 2 and SEQ ID NO: 3), F (residues 67-75 of SEQ ID NO: 2 and SEQ ID NO: 3), and G (residues 88-94 of SEQ ID NO: 2 and SEQ ID NO: 3), with an associated loop region sequence linked between each pair of adjacent β-strand domain sequences, each of the loop region sequences being selected from the group of loops AB, BC, CD, DE, EF, and FG; and optionally, an N-terminal tail of at least about 2 to about 33 amino acids, a C-terminal tail of at least about 2 to about 25 amino acids, or both;

wherein at least one loop region sequence is modified from the corresponding loop region of SEQ ID NO: 2 or SEQ ID NO:3, the at least one loop region sequence being selected from the group of (i) the BC loop region sequence comprising the amino acid sequence of SEQ ID NO: 23, (ii) the FG loop region sequence comprising the amino acid sequence of SEQ ID NO: 67, and (iii) the AB loop region sequence comprising the amino acid sequence of SEQ ID NO: 34; and wherein the polypeptide monobody exhibits estrogen receptor binding activity via interaction of the at least one loop region sequence with the estrogen receptor.

* * * * *

UNITED STATES PATENT AND TRADEMARK OFFICE
CERTIFICATE OF CORRECTION

PATENT NO. : 7,598,352 B2 Page 1 of 1
APPLICATION NO. : 10/006760
DATED : October 6, 2009
INVENTOR(S) : Shohei Koide It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1678 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 73

<210> SEQ ID NO 1
<211> LENGTH: 308
<212> TYPE: DNA
<213> ORGANISM: Homo sapiens

<400> SEQUENCE: 1

```
catatgcagg tttctgatgt tccgcgtgac ctggaagttg ttgctgcgac cccgactagc    60
ctgctgatca gctgggatgc tcctgcagtt accgtgcgtt attaccgtat cacgtacggt   120
gaaaccggtg gtaactcccc ggttcaggaa ttcactgtac ctggttccaa gtctactgct   180
accatcagcg gcctgaaacc gggtgtcgac tataccatca ctgtatacgc tgttactggc   240
cgtggtgaca gcccagcgag ctccaagcca atctcgatta actaccgtac ctagtaactc   300
gaggatcc                                                            308
```

<210> SEQ ID NO 2
<211> LENGTH: 96
<212> TYPE: PRT
<213> ORGANISM: Homo sapiens

<400> SEQUENCE: 2

```
Met Gln Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gly Arg
65                  70                  75                  80

Gly Asp Ser Pro Ala Ser Ser Lys Pro Ile Ser Ile Asn Tyr Arg Thr
                85                  90                  95
```

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence: mutant tenth fibronectin type 3 domain of human fibronectin
<220> FEATURE:
<221> NAME/KEY: UNSURE
<222> LOCATION: (9)
<223> OTHER INFORMATION: X at position 9 is either Asn or Lys

<400> SEQUENCE: 3

```
Met Gln Val Ser Asp Val Pro Arg Xaa Leu Glu Val Val Ala Ala Thr
 1               5                  10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gly Arg
65                  70                  75                  80
```

-continued

```
Gly Asp Ser Pro Ala Ser Ser Lys Pro Ile Ser Ile Asn Tyr Arg Thr
            85                  90                  95

<210> SEQ ID NO 4
<211> LENGTH: 618
<212> TYPE: DNA
<213> ORGANISM: Artificial Sequence
<220> FEATURE:
<223> OTHER INFORMATION: Description of Artificial Sequence:  B42-FNfn10
      fusion protein coding region
<220> FEATURE:
<221> NAME/KEY: unsure
<222> LOCATION: (112)..(113)
<223> OTHER INFORMATION: N at positions 112 and 113 can be A, C, T, or G
<220> FEATURE:
<221> NAME/KEY: unsure
<222> LOCATION: (115)..(116)
<223> OTHER INFORMATION: N at positions 115 and 116 can be A, C, T, or G
<220> FEATURE:
<221> NAME/KEY: unsure
<222> LOCATION: (118)..(119)
<223> OTHER INFORMATION: N at positions 118 and 119 can be A, C, T, or G
<220> FEATURE:
<221> NAME/KEY: unsure
<222> LOCATION: (121)..(122)
<223> OTHER INFORMATION: N at positions 121 and 122 can be A, C, T, or G
<220> FEATURE:
<221> NAME/KEY: unsure
<222> LOCATION: (124)..(125)
<223> OTHER INFORMATION: N at positions 124 and 125 can be A, C, T, or G
<220> FEATURE:
<221> NAME/KEY: unsure
<222> LOCATION: (268)..(269)
<223> OTHER INFORMATION: N at positions 268 and 269 can be A, C, T, or G
<220> FEATURE:
<221> NAME/KEY: unsure
<222> LOCATION: (271)..(272)
<223> OTHER INFORMATION: N at positions 271 and 272 can be A, C, T, or G
<220> FEATURE:
<221> NAME/KEY: unsure
<222> LOCATION: (274)..(275)
<223> OTHER INFORMATION: N at positions 274 and 275 can be A, C, T, or G
<220> FEATURE:
<221> NAME/KEY: unsure
<222> LOCATION: (277)..(278)
<223> OTHER INFORMATION: N at positions 277 and 278 can be A, C, T, or G
<220> FEATURE:
<221> NAME/KEY: unsure
<222> LOCATION: (280)..(281)
<223> OTHER INFORMATION: N at positions 280 and 281 can be A, C, T, or G
<220> FEATURE:
<221> NAME/KEY: unsure
<222> LOCATION: (283)..(284)
<223> OTHER INFORMATION: N at positions 283 and 284 can be A, C, T, or G
<220> FEATURE:
<221> NAME/KEY: unsure
<222> LOCATION: (286)..(287)
<223> OTHER INFORMATION: N at positions 286 and 287 can be A, C, T, or G
<220> FEATURE:
<221> NAME/KEY: unsure
<222> LOCATION: (114)
<223> OTHER INFORMATION: K at position 114 can be G or T
<220> FEATURE:
<221> NAME/KEY: unsure
<222> LOCATION: (117)
<223> OTHER INFORMATION: K at position 117 can be G or T
<220> FEATURE:
<221> NAME/KEY: unsure
<222> LOCATION: (120)
<223> OTHER INFORMATION: K at position 120 can be G or T
<220> FEATURE:
<221> NAME/KEY: unsure
<222> LOCATION: (123)
<223> OTHER INFORMATION: K at position 123 can be G or T
<220> FEATURE:
<221> NAME/KEY: unsure
<222> LOCATION: (126)
```

<223> OTHER INFORMATION: K at position 126 can be G or T
<220> FEATURE:
<221> NAME/KEY: unsure
<222> LOCATION: (270)
<223> OTHER INFORMATION: K at position 270 can be G or T
<220> FEATURE:
<221> NAME/KEY: unsure
<222> LOCATION: (273)
<223> OTHER INFORMATION: K at position 273 can be G or T
<220> FEATURE:
<221> NAME/KEY: unsure
<222> LOCATION: (276)
<223> OTHER INFORMATION: K at position 276 can be G or T
<220> FEATURE:
<221> NAME/KEY: unsure
<222> LOCATION: (279)
<223> OTHER INFORMATION: K at position 279 can be G or T
<220> FEATURE:
<221> NAME/KEY: unsure
<222> LOCATION: (282)
<223> OTHER INFORMATION: K at position 282 can be G or T
<220> FEATURE:
<221> NAME/KEY: unsure
<222> LOCATION: (285)
<223> OTHER INFORMATION: K at position 285 can be G or T
<220> FEATURE:
<221> NAME/KEY: unsure
<222> LOCATION: (288)
<223> OTHER INFORMATION: K at position 288 can be G or T

<400> SEQUENCE: 4

```
atggactaca aggacgacga tgacaagggt atgcaggttt ctgatgttcc gaccgacctg    60
gaagttgttg ctgcgacccc gactagcctg ctgatcagct gggatgctcc tnnknnknnk   120
nnknnktatt accgtatcac gtacggtgaa accggtggta actccccggt tcaggaattc   180
actgtacctg gttccaagtc tactgctacc atcagcggcc tgaaaccggg tgtcgactat   240
accatcactg tatacgctgt tactggcnnk nnknnknnkn nknnknnktc caagccaatc   300
tcgattaact accgtaccag tggtaccggt ggttccccctc aaaaaagaa gagaaaggta   360
gctggtatca ataaagatat cgaggagtgc aatgccatca ttgagcagtt tatcgactac   420
ctgcgcaccg acaggagat gccgatgaa atggcggatc aggcgattaa cgtggtgccg   480
ggcatgacgc cgaaaaccat tcttcacgcc gggccgccga tccagcctga ctggctgaaa   540
tcgaatggtt tcatgaaat tgaagcggat gttaacgata ccagcctctt gctgagtgga   600
gattaactcg aggcatgc                                                 618
```

<210> SEQ ID NO 5
<211> LENGTH: 201
<212> TYPE: PRT
<213> ORGANISM: Artificial Sequence
<220> FEATURE:
<223> OTHER INFORMATION: Description of Artificial Sequence: artificial
      B42-FNfn10 fusion protein
<220> FEATURE:
<221> NAME/KEY: UNSURE
<222> LOCATION: (38)..(42)
<223> OTHER INFORMATION: Xaa at any position can be any amino acid
<220> FEATURE:
<221> NAME/KEY: UNSURE
<222> LOCATION: (90)..(96)
<223> OTHER INFORMATION: Xaa at any position can be any amino acid

<400> SEQUENCE: 5

Met Asp Tyr Lys Asp Asp Asp Lys Gly Met Gln Val Ser Asp Val
 1               5                  10                  15

Pro Thr Asp Leu Glu Val Val Ala Ala Thr Pro Thr Ser Leu Leu Ile
            20                  25                  30

```
Ser Trp Asp Ala Pro Xaa Xaa Xaa Xaa Tyr Tyr Arg Ile Thr Tyr
        35                  40                  45

Gly Glu Thr Gly Gly Asn Ser Pro Val Gln Glu Phe Thr Val Pro Gly
 50                  55                  60

Ser Lys Ser Thr Ala Thr Ile Ser Gly Leu Lys Pro Gly Val Asp Tyr
 65                  70                  75                  80

Thr Ile Thr Val Tyr Ala Val Thr Gly Xaa Xaa Xaa Xaa Xaa Xaa
                85                  90                  95

Ser Lys Pro Ile Ser Ile Asn Tyr Arg Thr Ser Gly Thr Gly Gly Ser
        100                 105                 110

Pro Pro Lys Lys Arg Lys Val Ala Gly Ile Asn Lys Asp Ile Glu
        115                 120                 125

Glu Cys Asn Ala Ile Ile Glu Gln Phe Ile Asp Tyr Leu Arg Thr Gly
 130                 135                 140

Gln Glu Met Pro Met Glu Met Ala Asp Gln Ala Ile Asn Val Val Pro
145                 150                 155                 160

Gly Met Thr Pro Lys Thr Ile Leu His Ala Gly Pro Pro Ile Gln Pro
                165                 170                 175

Asp Trp Leu Lys Ser Asn Gly Phe His Glu Ile Glu Ala Asp Val Asn
        180                 185                 190

Asp Thr Ser Leu Leu Leu Ser Gly Asp
        195                 200

<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence:  FNfn10
      polypeptide monobody
<220> FEATURE:
<221> NAME/KEY: UNSURE
<222> LOCATION: (28)..(32)
<223> OTHER INFORMATION: Xaa at any position can be any amino acid
<220> FEATURE:
<221> NAME/KEY: UNSURE
<222> LOCATION: (80)..(86)
<223> OTHER INFORMATION: Xaa at any position can be any amino acid

<400> SEQUENCE: 6

Met Gln Val Ser Asp Val Pro Thr Asp Leu Glu Val Val Ala Ala Thr
 1               5                  10                  15

Pro Thr Ser Leu Leu Ile Ser Trp Asp Ala Pro Xaa Xaa Xaa Xaa Xaa
                20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
 50                  55                  60

Lys Pro Gly Val Asp Tyr Thr Ile Thr Val Tyr Ala Val Thr Gly Xaa
 65                  70                  75                  80

Xaa Xaa Xaa Xaa Xaa Xaa Ser Lys Pro Ile Ser Ile Asn Tyr Arg Thr
                85                  90                  95

<210> SEQ ID NO 7
<211> LENGTH: 684
<212> TYPE: DNA
<213> ORGANISM: Artificial Sequence
<220> FEATURE:
<223> OTHER INFORMATION: Description of Artificial Sequence:  B42-FNfn10
      fusion protein coding region
<220> FEATURE:
```

```
<221> NAME/KEY: unsure
<222> LOCATION: (409)..(410)
<223> OTHER INFORMATION: N at positions 409 and 410 can be A, C, T, or G
<220> FEATURE:
<221> NAME/KEY: unsure
<222> LOCATION: (412)..(413)
<223> OTHER INFORMATION: N at positions 412 and 413 can be A, C, T, or G
<220> FEATURE:
<221> NAME/KEY: unsure
<222> LOCATION: (415)..(416)
<223> OTHER INFORMATION: N at positions 415 and 416 can be A, C, T, or G
<220> FEATURE:
<221> NAME/KEY: unsure
<222> LOCATION: (418)..(419)
<223> OTHER INFORMATION: N at positions 418 and 419 can be A, C, T, or G
<220> FEATURE:
<221> NAME/KEY: unsure
<222> LOCATION: (421)..(422)
<223> OTHER INFORMATION: N at positions 421 and 422 can be A, C, T, or G
<220> FEATURE:
<221> NAME/KEY: unsure
<222> LOCATION: (424)..(425)
<223> OTHER INFORMATION: N at positions 424 and 425 can be A, C, T, or G
<220> FEATURE:
<221> NAME/KEY: unsure
<222> LOCATION: (427)..(428)
<223> OTHER INFORMATION: N at positions 427 and 428 can be A, C, T, or G
<220> FEATURE:
<221> NAME/KEY: unsure
<222> LOCATION: (411)
<223> OTHER INFORMATION: K at position 411 can be G or C
<220> FEATURE:
<221> NAME/KEY: unsure
<222> LOCATION: (414)
<223> OTHER INFORMATION: K at position 414 can be G or C
<220> FEATURE:
<221> NAME/KEY: unsure
<222> LOCATION: (417)
<223> OTHER INFORMATION: K at position 417 can be G or C
<220> FEATURE:
<221> NAME/KEY: unsure
<222> LOCATION: (420)
<223> OTHER INFORMATION: K at position 420 can be G or C
<220> FEATURE:
<221> NAME/KEY: unsure
<222> LOCATION: (423)
<223> OTHER INFORMATION: K at position 423 can be G or C
<220> FEATURE:
<221> NAME/KEY: unsure
<222> LOCATION: (426)
<223> OTHER INFORMATION: K at position 426 can be G or C
<220> FEATURE:
<221> NAME/KEY: unsure
<222> LOCATION: (428)
<223> OTHER INFORMATION: K at position 428 can be G or C

<400> SEQUENCE: 7
atgggtaagc ctatccctaa ccctctcctc ggtctcgatt ctacacaagc tatgggtgct      60
cctccaaaaa agaagagaaa ggtagctggt atcaataaag atatcgagga gtgcaatgcc     120
atcattgagc agtttatcga ctacctgcgc accggacagg agatgccgat ggaaatggcg     180
gatcaggcga ttaacgtggt gccgggcatg acgccgaaaa ccattcttca cgccgggccg     240
ccgatccagc ctgactggct gaaatcgaat ggttttcatg aaattgaagc ggatgttaac     300
gataccagcc tcttgctgag tggagatgcc tccaagcttg gtaccgagct cggatctatg     360
caggtttctg atgttccgac cgacctggaa gttgttgctg cgaccccgnn snnsnnsnns     420
nnsnnsnnsa ctagcctgct gatcagctgg gatgctcctg cagttaccgt gcgttattac     480
cgtatcacgt acggtgaaac cggtggtaac tccccggttc aggaattcac tgtacctggt     540
tccaagtcta ctgctaccat cagcggcctg aaaccgggtg tcgactatac catcactgta     600
tacgctgtta ctggccgtgg tgacagccca gcgagctcca agccaatctc gattaactac     660
```
cgtacctagt aactcgaggc atgc                                    684

<210> SEQ ID NO 8
<211> LENGTH: 222
<212> TYPE: PRT
<213> ORGANISM: Artificial Sequence
<220> FEATURE:
<223> OTHER INFORMATION: Description of Artificial Sequence: B42-FNfn10
    fusion protein
<220> FEATURE:
<221> NAME/KEY: UNSURE
<222> LOCATION: (137)..(143)
<223> OTHER INFORMATION: Xaa at any position can be any amino acid

<400> SEQUENCE: 8

Met Gly Lys Pro Ile Pro Asn Pro Leu Leu Gly Leu Asp Ser Thr Gln
 1               5                  10                  15

Ala Met Gly Ala Pro Lys Lys Lys Arg Lys Val Ala Gly Ile Asn
             20                  25                  30

Lys Asp Ile Glu Glu Cys Asn Ala Ile Ile Glu Gln Phe Ile Asp Tyr
         35                  40                  45

Leu Arg Thr Gly Gln Glu Met Pro Met Glu Met Ala Asp Gln Ala Ile
     50                  55                  60

Asn Val Val Pro Gly Met Thr Pro Lys Thr Ile Leu His Ala Gly Pro
 65                  70                  75                  80

Pro Ile Gln Pro Asp Trp Leu Lys Ser Asn Gly Phe His Glu Ile Glu
                 85                  90                  95

Ala Asp Val Asn Asp Thr Ser Leu Leu Leu Ser Gly Asp Ala Ser Lys
            100                 105                 110

Leu Gly Thr Glu Leu Gly Ser Met Gln Val Ser Asp Val Pro Thr Asp
        115                 120                 125

Leu Glu Val Val Ala Ala Thr Pro Xaa Xaa Xaa Xaa Xaa Xaa Xaa Thr
    130                 135                 140

Ser Leu Leu Ile Ser Trp Asp Ala Pro Ala Val Thr Val Arg Tyr Tyr
145                 150                 155                 160

Arg Ile Thr Tyr Gly Glu Thr Gly Gly Asn Ser Pro Val Gln Glu Phe
                165                 170                 175

Thr Val Pro Gly Ser Lys Ser Thr Ala Thr Ile Ser Gly Leu Lys Pro
            180                 185                 190

Gly Val Asp Tyr Thr Ile Thr Val Tyr Ala Val Thr Gly Arg Gly Asp
        195                 200                 205

Ser Pro Ala Ser Ser Lys Pro Ile Ser Ile Asn Tyr Arg Thr
    210                 215                 220

<210> SEQ ID NO 9
<211> LENGTH: 103
<212> TYPE: PRT
<213> ORGANISM: Artificial Sequence
<220> FEATURE:
<223> OTHER INFORMATION: Description of Artificial Sequence: FNfn10
    polypeptide monobody
<220> FEATURE:
<221> NAME/KEY: UNSURE
<222> LOCATION: (18)..(24)
<223> OTHER INFORMATION: Xaa at any position can be any amino acid

<400> SEQUENCE: 9

Met Gln Val Ser Asp Val Pro Thr Asp Leu Glu Val Val Ala Ala Thr
 1               5                  10                  15

Pro Xaa Xaa Xaa Xaa Xaa Xaa Xaa Thr Ser Leu Leu Ile Ser Trp Asp

```
                    20                  25                  30

Ala Pro Ala Val Thr Val Arg Tyr Tyr Arg Ile Thr Tyr Gly Glu Thr
            35                  40                  45

Gly Gly Asn Ser Pro Val Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Arg Gly Asp Ser Pro Ala Ser Ser Lys Pro
                85                  90                  95

Ile Ser Ile Asn Tyr Arg Thr
            100

<210> SEQ ID NO 10
<211> LENGTH: 704
<212> TYPE: DNA
<213> ORGANISM: Artificial Sequence
<220> FEATURE:
<223> OTHER INFORMATION: Description of Artificial Sequence:  B42-FNfn10
      fusion protein coding region
<220> FEATURE:
<221> NAME/KEY: unsure
<222> LOCATION: (439)..(440)
<223> OTHER INFORMATION: N at positions 439 and 440 can be A, C, T, or G
<220> FEATURE:
<221> NAME/KEY: unsure
<222> LOCATION: (442)..(443)
<223> OTHER INFORMATION: N at positions 442 and 443 can be A, C, T, or G
<220> FEATURE:
<221> NAME/KEY: unsure
<222> LOCATION: (445)..(446)
<223> OTHER INFORMATION: N at positions 445 and 446 can be A, C, T, or G
<220> FEATURE:
<221> NAME/KEY: unsure
<222> LOCATION: (448)..(449)
<223> OTHER INFORMATION: N at positions 448 and 449 can be A, C, T, or G
<220> FEATURE:
<221> NAME/KEY: unsure
<222> LOCATION: (451)..(452)
<223> OTHER INFORMATION: N at positions 451 and 452 can be A, C, T, or G
<220> FEATURE:
<221> NAME/KEY: unsure
<222> LOCATION: (595)..(596)
<223> OTHER INFORMATION: N at positions 595 and 596 can be A, C, T, or G
<220> FEATURE:
<221> NAME/KEY: unsure
<222> LOCATION: (598)..(599)
<223> OTHER INFORMATION: N at positions 598 and 599 can be A, C, T, or G
<220> FEATURE:
<221> NAME/KEY: unsure
<222> LOCATION: (601)..(602)
<223> OTHER INFORMATION: N at positions 601 and 602 can be A, C, T, or G
<220> FEATURE:
<221> NAME/KEY: unsure
<222> LOCATION: (604)..(605)
<223> OTHER INFORMATION: N at positions 604 and 605 can be A, C, T, or G
<220> FEATURE:
<221> NAME/KEY: unsure
<222> LOCATION: (607)..(608)
<223> OTHER INFORMATION: N at positions 607 and 608 can be A, C, T, or G
<220> FEATURE:
<221> NAME/KEY: unsure
<222> LOCATION: (610)..(611)
<223> OTHER INFORMATION: N at positions 610 and 611 can be A, C, T, or G
<220> FEATURE:
<221> NAME/KEY: unsure
<222> LOCATION: (613)..(614)
<223> OTHER INFORMATION: N at positions 613 and 614 can be A, C, T, or G
<220> FEATURE:
<221> NAME/KEY: unsure
<222> LOCATION: (441)
<223> OTHER INFORMATION: K at position 441 can be G or T
<220> FEATURE:
<221> NAME/KEY: unsure
```

<222> LOCATION: (444)
<223> OTHER INFORMATION: K at position 444 can be G or T
<220> FEATURE:
<221> NAME/KEY: unsure
<222> LOCATION: (447)
<223> OTHER INFORMATION: K at position 447 can be G or T
<220> FEATURE:
<221> NAME/KEY: unsure
<222> LOCATION: (450)
<223> OTHER INFORMATION: K at position 450 can be G or T
<220> FEATURE:
<221> NAME/KEY: unsure
<222> LOCATION: (453)
<223> OTHER INFORMATION: K at position 453 can be G or T
<220> FEATURE:
<221> NAME/KEY: unsure
<222> LOCATION: (597)
<223> OTHER INFORMATION: K at position 597 can be G or T
<220> FEATURE:
<221> NAME/KEY: unsure
<222> LOCATION: (600)
<223> OTHER INFORMATION: K at position 600 can be G or T
<220> FEATURE:
<221> NAME/KEY: unsure
<222> LOCATION: (603)
<223> OTHER INFORMATION: K at position 603 can be G or T
<220> FEATURE:
<221> NAME/KEY: unsure
<222> LOCATION: (606)
<223> OTHER INFORMATION: K at position 606 can be G or T
<220> FEATURE:
<221> NAME/KEY: unsure
<222> LOCATION: (609)
<223> OTHER INFORMATION: K at position 609 can be G or T
<220> FEATURE:
<221> NAME/KEY: unsure
<222> LOCATION: (612)
<223> OTHER INFORMATION: K at position 612 can be G or T
<220> FEATURE:
<221> NAME/KEY: unsure
<222> LOCATION: (615)
<223> OTHER INFORMATION: K at position 615 can be G or T

<400> SEQUENCE: 10

```
atgggtaagc ctatccctaa ccctctcctc ggtctcgatt ctacacaagc tatgggtgct      60
cctccaaaaa agaagagaaa ggtagctggt atcaataaag atatcgagga gtgcaatgcc     120
atcattgagc agtttatcga ctacctgcgc accggacagg agatgccgat ggaaatggcg     180
gatcaggcga ttaacgtggt gccgggcatg acgccgaaaa ccattcttca cgccgggccg     240
ccgatccagc ctgactggct gaaatcgaat ggttttcatg aaattgaagc ggatgttaac     300
gataccagcc tcttgctgag tggagatgcc tccaagcttg gtaccgagct cggatctatg     360
caggtttctg atgttccgac cgacctggaa gttgttgctg cgaccccgac tagcctgctg     420
atcagctggg atgctcctnn knnknnknnk nnktattacc gtatcacgta cggtgaaacc     480
ggtggtaact ccccggttca ggaattcact gtacctggtt ccaagtctac tgctaccatc     540
agcggcctga aacgggtgt cgactatacc atcactgtat acgctgttac tggcnnknnk     600
nnknnknnkn nknnktccaa gccaatctcg attaactacc gtacctagta actcgaggca     660
tgcatctaga gggccgcatc atgtaattag ttatgtcacg ctta                       704
```

<210> SEQ ID NO 11
<211> LENGTH: 215
<212> TYPE: PRT
<213> ORGANISM: Artificial Sequence
<220> FEATURE:
<223> OTHER INFORMATION: Description of Artificial Sequence: B42-FNfn10 fusion protein
<220> FEATURE:
<221> NAME/KEY: UNSURE

```
<222> LOCATION: (147)..(151)
<223> OTHER INFORMATION: Xaa at positions 147, 148, 149, 150, and 151
      can be any amino acid
<220> FEATURE:
<221> NAME/KEY: UNSURE
<222> LOCATION: (199)..(205)
<223> OTHER INFORMATION: Xaa at positions 199, 200, 201, 202, 203, 204,
      and 205 can be any amino acid

<400> SEQUENCE: 11
```

Met Gly Lys Pro Ile Pro Asn Pro Leu Leu Gly Leu Asp Ser Thr Gln
 1               5                  10                  15

Ala Met Gly Ala Pro Pro Lys Lys Lys Arg Lys Val Ala Gly Ile Asn
            20                  25                  30

Lys Asp Ile Glu Glu Cys Asn Ala Ile Ile Glu Gln Phe Ile Asp Tyr
        35                  40                  45

Leu Arg Thr Gly Gln Glu Met Pro Met Glu Met Ala Asp Gln Ala Ile
    50                  55                  60

Asn Val Val Pro Gly Met Thr Pro Lys Thr Ile Leu His Ala Gly Pro
65                  70                  75                  80

Pro Ile Gln Pro Asp Trp Leu Lys Ser Asn Gly Phe His Glu Ile Glu
                85                  90                  95

Ala Asp Val Asn Asp Thr Ser Leu Leu Leu Ser Gly Asp Ala Ser Lys
            100                 105                 110

Leu Gly Thr Glu Leu Gly Ser Met Gln Val Ser Asp Val Pro Thr Asp
        115                 120                 125

Leu Glu Val Val Ala Ala Thr Pro Thr Ser Leu Leu Ile Ser Trp Asp
    130                 135                 140

Ala Pro Xaa Xaa Xaa Xaa Xaa Tyr Tyr Arg Ile Thr Tyr Gly Glu Thr
145                 150                 155                 160

Gly Gly Asn Ser Pro Val Gln Glu Phe Thr Val Pro Gly Ser Lys Ser
                165                 170                 175

Thr Ala Thr Ile Ser Gly Leu Lys Pro Gly Val Asp Tyr Thr Ile Thr
            180                 185                 190

Val Tyr Ala Val Thr Gly Xaa Xaa Xaa Xaa Xaa Xaa Xaa Ser Lys Pro
        195                 200                 205

Ile Ser Ile Asn Tyr Arg Thr
    210                 215

```
<210> SEQ ID NO 12
<211> LENGTH: 96
<212> TYPE: PRT
<213> ORGANISM: Artificial Sequence
<220> FEATURE:
<223> OTHER INFORMATION: Description of Artificial Sequence:  FNfn10
      polypeptide monobody
<220> FEATURE:
<221> NAME/KEY: UNSURE
<222> LOCATION: (28)..(32)
<223> OTHER INFORMATION: Xaa at positions 28, 29, 30, 31, and 32 can be
      any amino acid
<220> FEATURE:
<221> NAME/KEY: UNSURE
<222> LOCATION: (80)..(85)
<223> OTHER INFORMATION: Xaa at positions 80, 81, 82, 83, 84, and 85 can
      be any amino acid

<400> SEQUENCE: 12
```

Met Gln Val Ser Asp Val Pro Thr Asp Leu Glu Val Val Ala Ala Thr
 1               5                  10                  15

Pro Thr Ser Leu Leu Ile Ser Trp Asp Ala Pro Xaa Xaa Xaa Xaa Xaa
            20                  25                  30

-continued

```
Tyr Tyr Arg Ile Thr Tyr Gly Glu Thr Gly Gly Asn Ser Pro Val Gln
         35                  40                  45

Glu Phe Thr Val Pro Gly Ser Lys Ser Thr Ala Thr Ile Ser Gly Leu
     50                  55                  60

Lys Pro Gly Val Asp Tyr Thr Ile Thr Val Tyr Ala Val Thr Gly Xaa
 65                  70                  75                  80

Xaa Xaa Xaa Xaa Xaa Xaa Ser Lys Pro Ile Ser Ile Asn Tyr Arg Thr
                 85                  90                  95

<210> SEQ ID NO 13
<211> LENGTH: 687
<212> TYPE: DNA
<213> ORGANISM: Artificial Sequence
<220> FEATURE:
<223> OTHER INFORMATION: Description of Artificial Sequence:  B42-FNfn10
      fusion protein coding region
<220> FEATURE:
<221> NAME/KEY: unsure
<222> LOCATION: (595)..(596)
<223> OTHER INFORMATION: N at positions 595 and 596 can be A, C, T, or G
<220> FEATURE:
<221> NAME/KEY: unsure
<222> LOCATION: (598)..(599)
<223> OTHER INFORMATION: N at positions 598 and 599 can be A, C, T, or G
<220> FEATURE:
<221> NAME/KEY: unsure
<222> LOCATION: (601)..(602)
<223> OTHER INFORMATION: N at positions 601 and 602 can be A, C, T, or G
<220> FEATURE:
<221> NAME/KEY: unsure
<222> LOCATION: (604)..(605)
<223> OTHER INFORMATION: N at positions 604 and 605 can be A, C, T, or G
<220> FEATURE:
<221> NAME/KEY: unsure
<222> LOCATION: (607)..(608)
<223> OTHER INFORMATION: N at positions 607 and 608 can be A, C, T, or G
<220> FEATURE:
<221> NAME/KEY: unsure
<222> LOCATION: (610)..(611)
<223> OTHER INFORMATION: N at positions 610 and 611 can be A, C, T, or G
<220> FEATURE:
<221> NAME/KEY: unsure
<222> LOCATION: (613)..(614)
<223> OTHER INFORMATION: N at positions 613 and 614 can be A, C, T, or G
<220> FEATURE:
<221> NAME/KEY: unsure
<222> LOCATION: (616)..(617)
<223> OTHER INFORMATION: N at positions 616 and 617 can be A, C, T, or G
<220> FEATURE:
<221> NAME/KEY: unsure
<222> LOCATION: (619)..(620)
<223> OTHER INFORMATION: N at positions 619 and 620 can be A, C, T, or G
<220> FEATURE:
<221> NAME/KEY: unsure
<222> LOCATION: (622)..(623)
<223> OTHER INFORMATION: N at positions 622 and 623 can be A, C, T, or G
<220> FEATURE:
<221> NAME/KEY: unsure
<222> LOCATION: (625)..(626)
<223> OTHER INFORMATION: N at positions 625 and 626 can be A, C, T, or G
<220> FEATURE:
<221> NAME/KEY: unsure
<222> LOCATION: (628)..(629)
<223> OTHER INFORMATION: N at positions 628 and 629 can be A, C, T, or G
<220> FEATURE:
<221> NAME/KEY: unsure
<222> LOCATION: (631)..(632)
<223> OTHER INFORMATION: N at positions 631 and 632 can be A, C, T, or G
<220> FEATURE:
<221> NAME/KEY: unsure
<222> LOCATION: (634)..(635)
<223> OTHER INFORMATION: N at positions can be 634 and 635 can be A, C,
      T, or G
<220> FEATURE:
```

<221> NAME/KEY: unsure
<222> LOCATION: (637)..(638)
<223> OTHER INFORMATION: N at positions 637 and 638 can be A, C, T, or G
<220> FEATURE:
<221> NAME/KEY: unsure
<222> LOCATION: (640)..(641)
<223> OTHER INFORMATION: N at positions 640 and 641 can be A, C, T, or G
<220> FEATURE:
<221> NAME/KEY: unsure
<222> LOCATION: (597)
<223> OTHER INFORMATION: K at position 597 can be G or T
<220> FEATURE:
<221> NAME/KEY: unsure
<222> LOCATION: (600)
<223> OTHER INFORMATION: K at position 600 can be G or T
<220> FEATURE:
<221> NAME/KEY: unsure
<222> LOCATION: (603)
<223> OTHER INFORMATION: K at position 603 can be G or T
<220> FEATURE:
<221> NAME/KEY: unsure
<222> LOCATION: (606)
<223> OTHER INFORMATION: K at position 606 can be G or T
<220> FEATURE:
<221> NAME/KEY: unsure
<222> LOCATION: (609)
<223> OTHER INFORMATION: K at position 609 can be G or T
<220> FEATURE:
<221> NAME/KEY: unsure
<222> LOCATION: (612)
<223> OTHER INFORMATION: K at position 612 can be G or T
<220> FEATURE:
<221> NAME/KEY: unsure
<222> LOCATION: (615)
<223> OTHER INFORMATION: K at position 615 can be G or T
<220> FEATURE:
<221> NAME/KEY: unsure
<222> LOCATION: (618)
<223> OTHER INFORMATION: K at position 618 can be G or T
<220> FEATURE:
<221> NAME/KEY: unsure
<222> LOCATION: (621)
<223> OTHER INFORMATION: K at position 621 can be G or T
<220> FEATURE:
<221> NAME/KEY: unsure
<222> LOCATION: (624)
<223> OTHER INFORMATION: K at position 624 can be G or T
<220> FEATURE:
<221> NAME/KEY: unsure
<222> LOCATION: (627)
<223> OTHER INFORMATION: K at position 627 can be G or T
<220> FEATURE:
<221> NAME/KEY: unsure
<222> LOCATION: (630)
<223> OTHER INFORMATION: K at position 630 can be G or T
<220> FEATURE:
<221> NAME/KEY: unsure
<222> LOCATION: (633)
<223> OTHER INFORMATION: K at position 633 can be G or T
<220> FEATURE:
<221> NAME/KEY: unsure
<222> LOCATION: (636)
<223> OTHER INFORMATION: K at position 636 can be G or T
<220> FEATURE:
<221> NAME/KEY: unsure
<222> LOCATION: (639)
<223> OTHER INFORMATION: K at position 639 can be G or T
<220> FEATURE:
<221> NAME/KEY: unsure
<222> LOCATION: (642)
<223> OTHER INFORMATION: K at position 642 can be G or T

<400> SEQUENCE: 13
atgggtaagc ctatccctaa ccctctcctc ggtctcgatt ctacacaagc tatgggtgct      60
cctccaaaaa agaagagaaa ggtagctggt atcaataaag atatcgagga gtgcaatgcc     120
atcattgagc agtttatcga ctacctgcgc accggacagg agatgccgat ggaaatggcg     180

-continued

```
gatcaggcga ttaacgtggt gccgggcatg acgccgaaaa ccattcttca cgccgggccg    240
ccgatccagc ctgactggct gaaatcgaat ggttttcatg aaattgaagc ggatgttaac    300
gataccagcc tcttgctgag tggagatgcc tccaagcttg gtaccgagct cggatctatg    360
cgtgtttctg atgttccgcg tgacctggaa gttgttgctg cgaccccgac tagcctgctg    420
atcagctggg atgctcctgc agttaccgtg cgttattacc gtatcactgt acggtgaaacc   480 ggtggtaact ccccggttca ggaattcact gtacctggtt ccaagtctac tgctaccatc    540
agcggcctga aaccgggtgt cgactatacc atcactgtat acgctgttac tggcnnkannk   600 nnknnknnkn nknnknnknn knnknnknnk nnknnknnkn nkaagccaat ctcgattaac    660
taccgtacct agtaactcga ggcatgc                                       687
```

<210> SEQ ID NO 14
<211> LENGTH: 223
<212> TYPE: PRT
<213> ORGANISM: Artificial Sequence
<220> FEATURE:
<223> OTHER INFORMATION: Description of Artificial Sequence: B42-FNfn10
    fusion protein
<220> FEATURE:
<221> NAME/KEY: UNSURE
<222> LOCATION: (199)..(214)
<223> OTHER INFORMATION: Xaa at positions 199, 200, 201, 202, 203, 204,
    205, 206, 207, 208, 209, 210, 211, 212, 213, and
    214 can be any amino acid <400> SEQUENCE: 14

```
Met Gly Lys Pro Ile Pro Asn Pro Leu Leu Gly Leu Asp Ser Thr Gln
  1               5                  10                  15

Ala Met Gly Ala Pro Pro Lys Lys Lys Arg Lys Val Ala Gly Ile Asn
             20                  25                  30

Lys Asp Ile Glu Glu Cys Asn Ala Ile Ile Glu Gln Phe Ile Asp Tyr
         35                  40                  45

Leu Arg Thr Gly Gln Glu Met Pro Met Glu Met Ala Asp Gln Ala Ile
     50                  55                  60

Asn Val Val Pro Gly Met Thr Pro Lys Thr Ile Leu His Ala Gly Pro
 65                  70                  75                  80

Pro Ile Gln Pro Asp Trp Leu Lys Ser Asn Gly Phe His Glu Ile Glu
                 85                  90                  95

Ala Asp Val Asn Asp Thr Ser Leu Leu Leu Ser Gly Asp Ala Ser Lys
            100                 105                 110

Leu Gly Thr Glu Leu Gly Ser Met Arg Val Ser Asp Val Pro Arg Asp
        115                 120                 125

Leu Glu Val Val Ala Ala Thr Pro Thr Ser Leu Leu Ile Ser Trp Asp
    130                 135                 140

Ala Pro Ala Val Thr Val Arg Tyr Tyr Arg Ile Thr Tyr Gly Glu Thr
145                 150                 155                 160

Gly Gly Asn Ser Pro Val Gln Glu Phe Thr Val Pro Gly Ser Lys Ser
                165                 170                 175

Thr Ala Thr Ile Ser Gly Leu Lys Pro Gly Val Asp Tyr Thr Ile Thr
            180                 185                 190

Val Tyr Ala Val Thr Gly Xaa Xaa Xaa Xaa Xaa Xaa Xaa Xaa Xaa
        195                 200                 205

Xaa Xaa Xaa Xaa Xaa Xaa Lys Pro Ile Ser Ile Asn Tyr Arg Thr
    210                 215                 220
```

<210> SEQ ID NO 15
<211> LENGTH: 104
<212> TYPE: PRT
<213> ORGANISM: Artificial Sequence
<220> FEATURE:
<223> OTHER INFORMATION: Description of Artificial Sequence: FNfn10
      polypeptide monobody
<220> FEATURE:
<221> NAME/KEY: UNSURE
<222> LOCATION: (80)..(95)
<223> OTHER INFORMATION: Xaa at positions 80, 81, 82, 83, 84, 85, 86,
      87, 88, 89, 90, 91, 92, 93, 94, and 95 can be any amino acid

<400> SEQUENCE: 15

Met Arg Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
50                  55                  60

Lys Pro Gly Val Asp Tyr Thr Ile Thr Val Tyr Ala Val Thr Gly Xaa
65                  70                  75                  80

Xaa Xaa Xaa Xaa Xaa Xaa Xaa Xaa Xaa Xaa Xaa Xaa Xaa Xaa Xaa Lys
                85                  90                  95

Pro Ile Ser Ile Asn Tyr Arg Thr
            100

<210> SEQ ID NO 16
<211> LENGTH: 663
<212> TYPE: DNA
<213> ORGANISM: Artificial Sequence
<220> FEATURE:
<223> OTHER INFORMATION: Description of Artificial Sequence: B42-FNfn10
      fusion protein coding region

<400> SEQUENCE: 16
atgggtaagc ctatccctaa ccctctcctc ggtctcgatt ctacacaagc tatgggtgct    60
cctccaaaaa agaagagaaa ggtagctggt atcaataaag atatcgagga gtgcaatgcc   120
atcattgagc agtttatcga ctacctgcgc accggacagg agatgccgat ggaaatggcg   180
gatcaggcga ttaacgtggt gccgggcatg acgccgaaaa ccattcttca cgccgggccg   240
ccgatccagc tgactggct gaaatcgaat ggttttcatg aaattgaagc ggatgttaac   300
gataccagcc tcttgctgag tggagatgcc tccaagcttg gtaccgagct cggatctatg   360
caggtttctg atgttccgac cgacctgaa gttgttgctg cgaccccgac tagcctgctg   420
atcagctggg atgctcctgc agttaccgtg cgttattacc gtatcacgta cggtgaaacc   480
ggtggtaact ccccggttca ggaattcact gtacctggtt ccaagtctac tgctaccatc   540
agcggcctga accgggtgt cgactatacc atcactgtat acgctgttac tggccgtggt   600
gacagcccag cgagctccaa gccaatctcg attaactacc gtacctagta actcgaggca   660
tgc                                                                663

<210> SEQ ID NO 17
<211> LENGTH: 215
<212> TYPE: PRT
<213> ORGANISM: Artificial Sequence
<220> FEATURE:
<223> OTHER INFORMATION: Description of Artificial Sequence: B42-FNfn10
      fusion protein

<400> SEQUENCE: 17

Met Gly Lys Pro Ile Pro Asn Pro Leu Leu Gly Leu Asp Ser Thr Gln
1               5                   10                  15

Ala Met Gly Ala Pro Pro Lys Lys Arg Lys Val Ala Gly Ile Asn
            20                  25                  30

Lys Asp Ile Glu Glu Cys Asn Ala Ile Ile Glu Gln Phe Ile Asp Tyr
        35                  40                  45

Leu Arg Thr Gly Gln Glu Met Pro Met Glu Met Ala Asp Gln Ala Ile
    50                  55                  60

Asn Val Val Pro Gly Met Thr Pro Lys Thr Ile Leu His Ala Gly Pro
65                  70                  75                  80

Pro Ile Gln Pro Asp Trp Leu Lys Ser Asn Gly Phe His Glu Ile Glu
                85                  90                  95

Ala Asp Val Asn Asp Thr Ser Leu Leu Leu Ser Gly Asp Ala Ser Lys
            100                 105                 110

Leu Gly Thr Glu Leu Gly Ser Met Gln Val Ser Asp Val Pro Thr Asp
        115                 120                 125

Leu Glu Val Val Ala Ala Thr Pro Thr Ser Leu Leu Ile Ser Trp Asp
    130                 135                 140

Ala Pro Ala Val Thr Val Arg Tyr Tyr Arg Ile Thr Tyr Gly Glu Thr
145                 150                 155                 160

Gly Gly Asn Ser Pro Val Gln Glu Phe Thr Val Pro Gly Ser Lys Ser
                165                 170                 175

Thr Ala Thr Ile Ser Gly Leu Lys Pro Gly Val Asp Tyr Thr Ile Thr
            180                 185                 190

Val Tyr Ala Val Thr Gly Arg Gly Asp Ser Pro Ala Ser Ser Lys Pro
        195                 200                 205

Ile Ser Ile Asn Tyr Arg Thr
    210                 215

<210> SEQ ID NO 18
<211> LENGTH: 1542
<212> TYPE: DNA
<213> ORGANISM: Artificial Sequence
<220> FEATURE:
<223> OTHER INFORMATION: Description of Artificial Sequence:
      lexA-ER(alpha)EF fusion protein

<400> SEQUENCE: 18
atgaaagcgt taacggccag gcaacaagag gtgtttgatc tcatccgtga tcacatcagc        60
cagacaggta tgccgccgac gcgtgcggaa atcgcgcagc gtttgggggtt ccgttcccca      120 aacgcggctg aagaacatct gaaggcgctg gcacgcaaag gcgttattga aattgtttcc      180
ggcgcatcac gcgggattcg tctgttgcag gaagaggaag aagggttgcc gctggtaggt      240
cgtgtggctg ccggtgaacc acttctggcg caacagcata ttgaaggtca ttatcaggtc      300
gatccttcct tattcaagcc gaatgctgat tcctgctgc gcgtcagcgg gatgtcgatg       360
aaagatatcg gcattatgga tggtgacttg ctggcagtgc ataaaactca ggatgtacgt      420
aacggtcagg tcgttgtcgc acgtattgat gacgaagtta ccgttaagcg cctgaaaaaa      480
cagggcaata aagtcgaact gttgccagaa aatagcgagt ttaaaccaat tgtcgtagat      540
cttcgtcagc agagcttcac cattgaaggg ctggcggttg gggttattcg caacggcgac      600
tggctggaat tcaagcttga gctcggcggc agcggtatga tcaaacgctc taagaagaac      660
agcctggcct tgtccctgac ggccgaccag atggtcagtg ccttgttgga tgctgagccc      720

```
cccatactct attccgagta tgatcctacc agacccttca gtgaagcttc gatgatgggc    780
ttactgacca acctggcaga cagggagctg gttcacatga tcaactgggc gaagagggtg    840
ccaggctttg tggatttgac cctccatgat caggtccacc ttctagaatg tgcctggcta    900
gagatcctga tgattggtct cgtctggcgc tccatggagc acccagtgaa gctactgttt    960
gctcctaact tgctcttgga caggaaccag ggaaaatgtg tagagggcat ggtggagatc   1020
ttcgacatgc tgctggctac atcatctcgg ttccgcatga tgaatctgca gggagaggag   1080
tttgtgtgcc tcaaatctat tattttgctt aattctggag tgtacacatt tctgtccagc   1140
accctgaagt ctctggaaga aaggaccat atccaccgag tcctggacaa gatcacagac    1200
actttgatcc acctgatggc caaggcaggc ctgaccctgc agcagcagca ccagcggctg   1260
gcccagctcc tcctcatcct ctcccacatc aggcacatga gtaacaaagg catggagcat   1320
ctgtacagca tgaagtgcaa gaacgtggtg cccctctatg acctgctgct ggagatgctg   1380
gacgcccacc gcctacatgc gcccactagc cgtggagggg catccgtgga ggagacggac   1440
caaagccact tggccactgc gggctctact tcatcgcatt ccttgcaaaa gtattacatc   1500
acggggaggg cagagggttt ccctgccaca gtctgactcg ag                      1542
```

<210> SEQ ID NO 19
<211> LENGTH: 511
<212> TYPE: PRT
<213> ORGANISM: Artificial Sequence
<220> FEATURE:
<223> OTHER INFORMATION: Description of Artificial Sequence:
      lexA-ER(alpha)EF fusion protein

<400> SEQUENCE: 19

```
Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
 65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Lys Leu Glu Leu
        195                 200                 205
```

-continued

```
Gly Gly Ser Gly Met Ile Lys Arg Ser Lys Asn Ser Leu Ala Leu
        210                 215                 220

Ser Leu Thr Ala Asp Gln Met Val Ser Ala Leu Leu Asp Ala Glu Pro
225                 230                 235                 240

Pro Ile Leu Tyr Ser Glu Tyr Asp Pro Thr Arg Pro Phe Ser Glu Ala
                245                 250                 255

Ser Met Met Gly Leu Leu Thr Asn Leu Ala Asp Arg Glu Leu Val His
                260                 265                 270

Met Ile Asn Trp Ala Lys Arg Val Pro Gly Phe Val Asp Leu Thr Leu
                275                 280                 285

His Asp Gln Val His Leu Leu Glu Cys Ala Trp Leu Glu Ile Leu Met
290                 295                 300

Ile Gly Leu Val Trp Arg Ser Met Glu His Pro Val Lys Leu Leu Phe
305                 310                 315                 320

Ala Pro Asn Leu Leu Leu Asp Arg Asn Gln Gly Lys Cys Val Glu Gly
                325                 330                 335

Met Val Glu Ile Phe Asp Met Leu Leu Ala Thr Ser Ser Arg Phe Arg
                340                 345                 350

Met Met Asn Leu Gln Gly Glu Glu Phe Val Cys Leu Lys Ser Ile Ile
                355                 360                 365

Leu Leu Asn Ser Gly Val Tyr Thr Phe Leu Ser Ser Thr Leu Lys Ser
370                 375                 380

Leu Glu Glu Lys Asp His Ile His Arg Val Leu Asp Lys Ile Thr Asp
385                 390                 395                 400

Thr Leu Ile His Leu Met Ala Lys Ala Gly Leu Thr Leu Gln Gln Gln
                405                 410                 415

His Gln Arg Leu Ala Gln Leu Leu Leu Ile Leu Ser His Ile Arg His
                420                 425                 430

Met Ser Asn Lys Gly Met Glu His Leu Tyr Ser Met Lys Cys Lys Asn
                435                 440                 445

Val Val Pro Leu Tyr Asp Leu Leu Leu Glu Met Leu Asp Ala His Arg
450                 455                 460

Leu His Ala Pro Thr Ser Arg Gly Gly Ala Ser Val Glu Glu Thr Asp
465                 470                 475                 480

Gln Ser His Leu Ala Thr Ala Gly Ser Thr Ser Ser His Ser Leu Gln
                485                 490                 495

Lys Tyr Tyr Ile Thr Gly Glu Ala Glu Gly Phe Pro Ala Thr Val
                500                 505                 510

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: protein
<220> FEATURE:
<221> NAME/KEY: UNSURE
<222> LOCATION: (2)..(3)
<223> OTHER INFORMATION: X at any position can be any amino acid

<400> SEQUENCE: 20

Leu Xaa Xaa Leu Leu
 1               5

<210> SEQ ID NO 21
<211> LENGTH: 4
<212> TYPE: PRT
<213> ORGANISM: Artificial Sequence
```

```
<220> FEATURE:
<223> OTHER INFORMATION: Description of Artificial Sequence:
      endoplasmic reticulum localization signal

<400> SEQUENCE: 21

Lys Asp Glu Leu
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:  BC loop
      sequence for polypeptide monobody in pFNB42B5F7
      library

<400> SEQUENCE: 22

Trp Tyr Gln Gly Arg
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:  BC loop
      sequence for polypeptide monobody in pFNB42B5F7
      library

<400> SEQUENCE: 23

Pro Arg Thr Lys Gln
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:  BC loop
      sequence for polypeptide monobody in pFNB42B5F7
      library

<400> SEQUENCE: 24

Val Arg Arg Pro Pro
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 25

Gly Ile Leu Glu Met Leu Gln
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library
```

-continued

```
<400> SEQUENCE: 26

Arg Leu Arg Ala Gln Leu Val
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 27

Pro Val Arg Val Leu Leu Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 28

Arg Leu Arg Asp Leu Leu Gln
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 29

Gly Leu Val Ser Leu Leu Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 30

Arg Lys Val Val Trp Thr Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pFNB42B5F7
      library

<400> SEQUENCE: 31

Thr Ala Ala Ile Met Val Lys
1               5
```

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: UNSURE
<222> LOCATION: (2)..(3)
<223> OTHER INFORMATION: X at any position can be an amino acid

<400> SEQUENCE: 32

Leu Xaa Xaa Met Leu
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: sequence
      within helix 12 of estrogen receptor-alpha and
      estrogen receptor-beta

<400> SEQUENCE: 33

Leu Leu Glu Met Leu
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: AB loop
      sequence for polypeptide monobody in pYT45AB7N
      library

<400> SEQUENCE: 34

Trp Thr Trp Val Leu Arg Glu
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: AB loop
      sequence for polypeptide monobody in pYT45AB7N
      library

<400> SEQUENCE: 35

Trp Val Leu Ile Thr Arg Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: FG loop
      sequence for polypeptide monobody in pYT45B3F7
      library

<400> SEQUENCE: 36

Leu Arg Leu Met Leu Ala Gly
 1               5

```
<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 37

Ala Leu Val Glu Met Leu Arg
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 38

Arg Leu Leu Trp Asn Ser Leu
  1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 39

Arg Val Leu Met Thr Leu Leu
  1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 40

Gly Leu Arg Arg Leu Leu Arg
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 41

Gly Leu Arg Gln Met Leu Gly
  1               5

<210> SEQ ID NO 42
<211> LENGTH: 7
<212> TYPE: PRT
```

```
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 42

Arg Val Leu His Ser Leu Leu
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 43

Arg Val Arg Asp Leu Leu Met
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 44

Arg Val Met Asp Met Leu Leu
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 45

Gly Ile Ala Glu Leu Leu Arg
 1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 46

Arg Ile Leu Leu Asn Met Leu Thr
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
```

-continued

```
      library

<400> SEQUENCE: 47

Gly Gly Trp Leu Trp Cys Val Thr
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 48

Thr Trp Val Val Arg Arg Val
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 49

Thr Trp Val Arg Pro Asn Gln
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 50

Arg Arg Val Pro Ile Trp Cys
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 51

Arg Arg Val Tyr Asp Phe Leu
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 52
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT45B3F7
      library

<400> SEQUENCE: 53

Gly Leu Arg Met Leu Leu Arg
  1               5

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 54

Ser Arg Arg Leu Val Glu His Leu Ala Gly Val Glu Val Gln Ala Leu
  1               5                  10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 55

Leu Val Ala Arg Met Leu Asp Trp Ser Asp Gly Glu Glu Ala Ser Pro
  1               5                  10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 56

Gln Gly Lys Gly Arg Arg Arg Gly Leu Val Leu Tyr Leu Leu Gly Ser
  1               5                  10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 57

Arg Leu Arg Glu Leu Leu Ala Glu Ala Ala Gln Ala Ser Asp Gly Glu
  1               5                  10                  15
```

Leu Arg Gln Met Leu Ala Asp (preceding, SEQ 52 continued)

```
<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 58

Leu Leu Leu Arg Val Gly Cys Gly Cys Arg Leu Val Gly Ser Val Leu
 1               5                  10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 59

Arg Leu Ser Ile Val Pro Cys Pro Ala Trp Ala Arg Leu Thr Val Leu
 1               5                  10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 60

Leu Leu Val Gly Leu Leu Leu Arg Gly Ala Arg Ser Gly Ser Thr
 1               5                  10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 61

Leu Ile Tyr Gly Leu Leu Ser Gln Pro Glu Glu Arg Asp Glu Trp Arg
 1               5                  10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 62

Arg Ser Asp Gly Val Leu Leu Arg Leu Leu Ala Gly Gln Arg Asn Ala
 1               5                  10                  15

<210> SEQ ID NO 63
<211> LENGTH: 16
<212> TYPE: PRT
<213> ORGANISM: Artificial Sequence
```

```
<220> FEATURE:
<223> OTHER INFORMATION: Description of Artificial Sequence:  FG loop
      sequence for polypeptide monobody in pYT47F16
      library

<400> SEQUENCE: 63

Trp Phe Asp His Glu Arg His Gly Met Leu Trp Gln Leu Leu Leu Arg
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 64

Arg Leu Trp Cys Leu Leu Gln Arg Lys Gly Arg Asn Pro Ile Asp Met
 1               5                  10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 65

Arg Val Phe Phe Gly Ile Gly Cys Arg Gly Gly Thr Gly Gly Gly Asn
 1               5                  10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 66

Arg Val Arg Phe Arg Cys Gly Gly Arg Asp Ala Ala Ser Gly Asp Gln
 1               5                  10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 67

Leu Val Arg Phe Arg Val Val Asn Ser Ser Leu Cys Met Trp Ala Arg
 1               5                  10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library
```

```
<400> SEQUENCE: 68

Leu Val Arg Leu Gly Val Ala Gly His Met Asp Ala Gly Ala Gly Arg
 1               5                  10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 69

Pro Ala Asp Gly Ser Glu Val Leu Arg Leu Val Lys Ile His Tyr Val
 1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 70

Arg Leu Glu Tyr Gly Asp Val Ile Gly Ala Val Trp Trp Gly Arg Val
 1               5                  10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 71

Gln Gly Ala Ala Val Arg Thr Leu Val Ala Gly Gly Gly Val Ala Ser
 1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library

<400> SEQUENCE: 72

Leu Glu Val Arg Val Ala Ala Gly Cys Ile Ala Gly Gly Gly Arg Arg
 1               5                  10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence:  FG loop
      sequence for polypeptide monobody in pYT47F16
      library
```

-continued

```
<400> SEQUENCE: 73

Arg Leu Trp Arg Met Leu Ser Gly Glu Pro Ala Arg Val Asp His Glu
1               5                   10                  15
```